(12) United States Patent
Degnan et al.

(10) Patent No.: US 7,772,244 B2
(45) Date of Patent: Aug. 10, 2010

(54) THERAPEUTIC AGENTS FOR THE TREATMENT OF MIGRAINE

(75) Inventors: Andrew P. Degnan, New Haven, CT (US); Xiaojun Han, Cheshire, CT (US); Gene M. Dubowchik, Middlefield, CT (US); John E. Macor, Guilford, CT (US); Stephen E. Mercer, Middletown, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1455 days.

(21) Appl. No.: 11/091,429

(22) Filed: Mar. 28, 2005

(65) Prior Publication Data

US 2005/0215576 A1 Sep. 29, 2005

Related U.S. Application Data

(60) Provisional application No. 60/557,408, filed on Mar. 29, 2004.

(51) Int. Cl.
 *A61K 31/517* (2006.01)
 *A61K 31/47* (2006.01)
 *C07D 215/227* (2006.01)
 *C07D 239/80* (2006.01)

(52) U.S. Cl. .................. 514/266.22; 514/312; 544/286; 546/157

(58) Field of Classification Search ............ 514/266.22, 514/312; 546/157; 544/286
See application file for complete search history.

(56) References Cited

U.S. PATENT DOCUMENTS

| | | | |
|---|---|---|---|
| 6,313,097 B1 | 11/2001 | Eberlein et al. | |
| 6,344,449 B1 | 2/2002 | Rudolf et al. | |
| 6,521,609 B1 | 2/2003 | Doods et al. | |
| 6,552,043 B1 | 4/2003 | Patchett et al. | |
| 6,982,263 B2 * | 1/2006 | Hickey et al. | 514/235.2 |
| 7,384,930 B2 * | 6/2008 | Chaturvedula et al. | 514/212.06 |
| 7,384,931 B2 * | 6/2008 | Chaturvedula et al. | 514/212.06 |
| 7,449,586 B2 * | 11/2008 | Chaturvedula et al. | 548/362.5 |
| 2001/0036946 A1 | 11/2001 | Rudolf et al. | |
| 2003/0139417 A1 | 7/2003 | Eberlein et al. | |
| 2003/0181462 A1 | 9/2003 | Doods et al. | |
| 2003/0191068 A1 | 10/2003 | Trunk et al. | |
| 2003/0212057 A1 | 11/2003 | Rudolf et al. | |
| 2003/0236282 A1 | 12/2003 | Hurnaus et al. | |
| 2004/0014679 A1 | 1/2004 | Trunk et al. | |
| 2004/0063735 A1* | 4/2004 | Chaturvedula et al. | 514/266.22 |
| 2004/0076587 A1 | 4/2004 | Kruss et al. | |
| 2004/0132716 A1 | 7/2004 | Rudolf et al. | |
| 2004/0192729 A1 | 9/2004 | Rudolf et al. | |
| 2004/0204397 A1 | 10/2004 | Chaturvedula et al. | |
| 2004/0214819 A1 | 10/2004 | Rudolf et al. | |
| 2004/0229861 A1 | 11/2004 | Burgey et al. | |
| 2004/0248816 A1 | 12/2004 | Doods et al. | |
| 2005/0032783 A1 | 2/2005 | Doods et al. | |
| 2005/0065094 A1 | 3/2005 | Davidai | |
| 2005/0153959 A1* | 7/2005 | Luo et al. | 514/227.5 |
| 2005/0215546 A1 | 9/2005 | Hurnaus et al. | |
| 2005/0215576 A1 | 9/2005 | Degnan et al. | |
| 2005/0227968 A1 | 10/2005 | Lustenberger et al. | |
| 2005/0233980 A1 | 10/2005 | Doods et al. | |
| 2005/0234054 A1 | 10/2005 | Mueller et al. | |
| 2005/0234067 A1 | 10/2005 | Mueller et al. | |
| 2005/0250763 A1 | 11/2005 | Mueller et al. | |
| 2005/0256098 A1 | 11/2005 | Burgey et al. | |
| 2005/0256099 A1 | 11/2005 | Mueller et al. | |
| 2005/0272955 A1 | 12/2005 | Zimmer et al. | |
| 2006/0094707 A1 | 5/2006 | Chaturvedula et al. | |

FOREIGN PATENT DOCUMENTS

| | | |
|---|---|---|
| CA | 2 387 613 | 5/2001 |
| CA | 2503455 | 4/2005 |
| WO | WO 97/09046 | 3/1997 |
| WO | WO 98/09630 | 3/1998 |
| WO | WO 98/11128 | 3/1998 |
| WO | WO 98/56779 | 12/1998 |
| WO | WO 99/52875 | 10/1999 |
| WO | WO 00/18764 | 4/2000 |
| WO | WO 00/55154 | 9/2000 |

(Continued)

OTHER PUBLICATIONS

U.S. Appl. No. 11/417,326, filed May 3, 2006, Chaturvedula, et al.

(Continued)

*Primary Examiner*—James O Wilson
*Assistant Examiner*—Tamthom N Truong
(74) *Attorney, Agent, or Firm*—Shah R. Makujina; James Epperson

(57) ABSTRACT

The present invention relates to compounds of Formula (I)

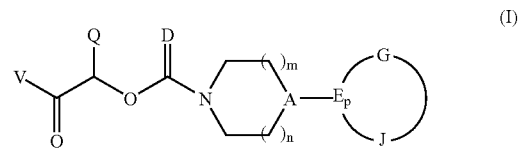

as antagonists of calcitonin gene-related peptide receptors ("CGRP-receptor"), pharmaceutical compositions comprising them, methods for identifying them, methods of treatment using them and their use in therapy for treatment of neurogenic vasodilation, neurogenic inflammation, migraine and other headaches, thermal injury, circulatory shock, flushing associated with menopause, airway inflammatory diseases, such as asthma and chronic obstructive pulmonary disease (COPD), and other conditions the treatment of which can be effected by the antagonism of CGRP-receptors.

14 Claims, No Drawings

FOREIGN PATENT DOCUMENTS

| WO | WO 01/25228 | 4/2001 |
|---|---|---|
| WO | WO 01/32648 | 5/2001 |
| WO | WO 01/32649 | 5/2001 |
| WO | WO 01/49676 | 7/2001 |
| WO | WO 02/10140 | 2/2002 |
| WO | 1 227 090 A1 | 7/2002 |
| WO | WO 03/027252 | 4/2003 |
| WO | WO 03/070753 | 8/2003 |
| WO | WO 03/076432 | 9/2003 |
| WO | WO 03/104236 | 12/2003 |
| WO | WO 2004/037810 | 5/2004 |
| WO | WO 2004/082602 A2 | 9/2004 |
| WO | WO 2004/082605 A2 | 9/2004 |
| WO | WO 2004/082678 A1 | 9/2004 |
| WO | WO 2004/083187 A1 | 9/2004 |
| WO | WO 2004/087649 A2 | 10/2004 |
| WO | WO 2004/091514 A2 | 10/2004 |
| WO | WO 2004/092166 A2 | 10/2004 |
| WO | WO 2004/092166 A2 | 10/2004 |
| WO | WO 2004/092168 A1 | 10/2004 |
| WO | WO 2004/092168 A1 | 10/2004 |
| WO | WO 2005/000807 | 1/2005 |
| WO | WO 2005/009962 | 2/2005 |
| WO | WO 2005/013894 | 2/2005 |
| WO | WO 2005/056550 | 6/2005 |
| WO | WO2005/065779 | 7/2005 |
| WO | WO 2005/072308 | 8/2005 |
| WO | WO2005/084672 | 9/2005 |
| WO | WO 2005/092880 | 10/2005 |
| WO | WO 2005/095383 | 10/2005 |
| WO | WO 2005/100343 | 10/2005 |
| WO | WO 2005/100352 | 10/2005 |
| WO | WO/2005/100360 | 10/2005 |
| WO | WO 2005/102322 | 11/2005 |
| WO | WO 2005/103037 | 11/2005 |
| WO | WO 2005/121078 | 12/2005 |
| WO | WO2006/052378 | 5/2006 |
| WO | WO 2006/060678 | 6/2006 |

OTHER PUBLICATIONS

U.S. Appl. No. 11/247,697, filed Oct. 11, 2005, Chaturvedula, et al.
U.S. Appl. No. 11/291,670, filed Dec. 1, 2005, Chaturvadula, et al.
Carlström, A.-S. and Frejd, T., Palladium-Catalyzed Synthesis of Didehydroamino Acid Derivatives, *Synthesis*, 1989, 6, 414-418.
Carlström, A.-S. and Frejd, T., "Palladium-Catalyzed Bis-coupling of Dihaloaromatics with 2-Amidoacrylates", *J. Org. Chem.*, 1991, 56, 1289-1293.
Dygos, J.H., et al., "A Convenient Asymmetric Synthesis of the Unnatural Amino Acid 2,6-Dimethyl-L-tyrosine", *Synthesis*, 1992, 741-743.
Rudolf, K., et al., "Development of Human Calcitonin Gene-Related Peptide (CGRP) Receptor Antagonists. 1. Potent and Selective Small Molecule CGRP Antagonists. 1-[$N^2$-[3,5-Dibromo-$N$-[[4-(3,4-dihydro-2(1$H$)-oxoquinazolin-3-yl)-1-piperidinyl]carbonyl]-D-tyrosyl]L-lysyl]-4-(4-pyridinyl)piperazine: The First CGRP Antagonist for Clinical Trials in Acute Migraine", *J. Med. Chem.* 2005, 48, 5921-5931.
Xin, Z., et al., "Potent, Selective Inhibitors of Protein Tyrosine Phosphatase IB", *Bioorg. & Med. Chem. Lett.*, 2003, 13, 1887-1890.
Olesen, J. et al., "Calcitonin Gene-Related Peptide Receptor Antagonist BIBN 4096 BS for the Acute Treatment of Migraine", *New England J. of Medicine*, 2004, 350 (11): 1104-1110.
Pasternak, et al., "Potent, orally bioavailable somatostatin agonists: good absorption achieved by urea backbone cyclization", *Bioorganic & Medicinal Chemistry* Letters, Oxford GB, vol. 9, No. 3, Feb. 8, 1999, 491-496.
U.S. Appl. No. 11/004,706, filed Dec. 3, 2004, Luo, et al.
U.S. Appl. No. 60/624,655, filed Nov. 3, 2004, Chaturvedula and Mercer.
U.S. Appl. No. 60/633,159, filed Dec. 3, 2004, Chaturvedula et al.
U.S. Appl. No. 60/678,099, filed May 5, 2005, Chaturvedula and Mercer.
Ashina, M., et al., "Evidence for increased plasma levels of calcitonin gene-related peptide in migraine outside of attacks", *Pain*, 2000, 86(1-2):133-138.
Brain, S.D. et al., "CGRP receptors: a headache to sudy, but will antagonists prove therapeutic in migraine?", *TiPS*, 2002, 23(2): 51-53.
Chu, D.Q. et al.,, "The calcitonin gene-related peptide (CGRP) antagonist CGRP8-37 blocks vasodilatation in inflamed rat skin: involvement of adrenomedullin in addition to CGRP", *Neuroscience Lett.*, 2001, 310: 169-172.
De Vries, P. et al., "Pharmacological aspects of experimental headache models in relation to acute antimigraine therapy", *Eur. J. of Pharmacol.*, 1990, 375: 61-74.
Doods, H. et al., "Pharmacological profile of BIBN4096BS, the first selective small molecule CGRP antagonist", *Br. J. of Pharmacol.*, 2000, 129: 420-423.
Edvinsson, L., "Calcitonin Gene-Related Peptide (CGRP) and the Pathophysiology of Headache", *CNS Drugs*, 2001,15(10): 745-753.
Escott, K.J., "Trigeminal ganglion stimulation increases facial skin blood flow in the rat: a major role for calcitonic gene-related peptide", *Brain Research*, 1995, 669: 93-99.
Escott, K.J, and Brain, S.D., "Effect of a calcitonin gene-related peptide antagonist (CGRP8-37) on skin vasodilation and oedema induced by stimulation of the rat saphenous nerve", *Br J Pharmacol.*, 1993, 110: 772-6.
Evans, B.N. et al., "CGRP-RCP, a Novel Protein Required for Signal Transduction at Calcitonin Gene-related Peptide and Adrenomedullin Receptors", *J. Biol. Chem.* 2000, 275(4): 31438-31443.
Gallai, V. et al. "Vasoactive peptide levels in the plasma of young migraine patients with and without aura assessed byoth interictally and ictally", *Cephalalgia*, 1995,15(5): 384-390.
Goadsby, P.J. et al., "Vasoactive peptide release in the extracerebral circulation of humans during migrain headache", *Annals of Neurology*, 1990, 28(2):183-187.
Grant, A.D. et al., "Evidence of a role for $NK_1$ and CGRP receptors in mediating neurogenic vasodilation in the mouse ear", *Brit. J. Pharmacol.* 2002, 135: 356-362.
Hall, J.M. et al., "Interaction of human adrenomedullin $_{13-52}$ with calcitonin gene-related peptide receptors in the microvasculature of the rat and hamster", *Br. J. of Pharmacol.*, 1995, 114: 592-597.
Hall, J.M. and Brain, S.D., "Interaction of amylin with calcitonin gene-related peptide receptors in the microvasculature of the hamster cheek pouch in vivo", 1999, 126: 280-284.
Juaneda, C. et al. "The molecular pharmacology of CGRP and related peptide receptor subtypes", *TiPS*, 2000, 21: 432-438.
Lassen, L.H. et al. "CGRP may play a causative role in migraine", *Cephalalgia*, 2002 22(1) 54-61.
Mallee, J.J. et al. "Receptor Activity-modifying Protein 1 Determines the Species Selectivity of Non-peptide CGRP Receptor Antagonist", *J., Biol. Chem.*, 2002, 277(16): 14294-14298.
McLatchie, L.M. et al., "RAMPs regulate the transport and ligand specificity of the calcitonin-receptor-like receptor", *Nature*, 1998, 393: 333-339.
Poyner, D.R. et al., "Pharmacological characterization of a receptor for calcitonin gene-related peptide on rat, L6 myocytes", *Brit. J. of Pharm.*, 1992, 105: 441-447.
Rosenfeld, M. G., et al., "Production of a novel neuropeptide encoded by the calcitonin gene via tissue-specific RNA Processing", *Nature*, 1983, 304:129-135.
Shen, Y.-T. et al., "Functional Role of α-Calcitonin Gene-Related Peptide in the Regulation of the Cardiovascular System", *J. Pharm. Exp. Ther.*, 2001, 298(2): 551-558.

Van Valen, F. et al., "Calcitonin gene-related peptide (CGRP) receptors are linked to cyclic adenosine monophosphate production in SK-N-MC human neuroblastoma cells", *Neuroscience Letters,* 1990, 119: 195-198.

Williamson, D.J. and Hargreaves, R.J., "Neurogenic Inflammation in the Context of Migraine", *Microsc. Res. Tech.,* 2001, 53: 167-178.

Williamson, D.J., et al., "Intravital microscope studies on the side effects of neurokinin agonists and calcitonin gene-related peptide on dural vessel diameter in the anaesthetized rat", *Cephalalgia,* 1997, 17(4): 518-524.

Williamson, D.J., et al., "Sumatriptan inhibits neurogenic vasodilation of dural blood vessels in the anaesthetized rat-intraval microscope studies", *Cephalalgia,* 1997, 17(4):525-531.

\* cited by examiner

THERAPEUTIC AGENTS FOR THE TREATMENT OF MIGRAINE

CROSS-REFERENCE TO RELATED APPLICATIONS

This is a non-provisional application which claims the benefit of U.S. Provisional Application No. 60/557,408 filed Mar. 29, 2004.

FIELD OF THE INVENTION

The present invention relates to novel small molecule antagonists of calcitonin gene-related peptide receptors ("CGRP-receptor"), pharmaceutical compositions comprising them, methods for identifying them, methods of treatment using them and their use in therapy for treatment of neurogenic vasodilation, neurogenic inflammation, migraine, cluster headache and other headaches, thermal injury, circulatory shock, flushing associated with menopause, airway inflammatory diseases, such as asthma and chronic obstructive pulmonary disease (COPD), and other conditions the treatment of which can be effected by the antagonism of CGRP-receptors.

BACKGROUND OF THE INVENTION

Calcitonin gene-related peptide (CGRP) is a naturally occurring 37-amino-acid peptide first identified in 1982 (Amara, S. G. et al, *Science* 1982, 298, 240-244). Two forms of the peptide are expressed (αCGRP and βCGRP) which differ by one and three amino acids in rats and humans, respectively. The peptide is widely distributed in both the peripheral (PNS) and central nervous system (CNS), principally localized in sensory afferent and central neurons, and displays a number of biological effects, including vasodilation.

When released from the cell, CGRP binds to specific cell surface G protein-coupled receptors and exerts its biological action predominantly by activation of intracellular adenylate cyclase (Poyner, D. R. et al, *Br J Pharmacol* 1992, 105, 441-7; Van Valen, F. et al, *Neurosci Lett* 1990, 119, 195-8.). Two classes of CGRP receptors, $CGRP_1$ and $CGRP_2$, have been proposed based on the antagonist properties of the peptide fragment CGRP(8-37) and the ability of linear analogues of CGRP to activate $CGRP_2$ receptors (Juaneda, C. et al. *TiPS* 2000, 21, 432-438). However, there is lack of molecular evidence for the $CGRP_2$ receptor (Brain, S. D. et al, *TiPS* 2002, 23, 51-53). The $CGRP_1$ receptor has three components: (i) a 7 transmembrane calcitonin receptor-like receptor (CRLR); (ii) the single transmembrane receptor activity modifying protein type one (RAMP1); and (iii) the intracellular receptor component protein (RCP) (Evans B. N. et al., *J Biol. Chem.* 2000, 275, 31438-43). RAMP1 is required for transport of CRLR to the plasma membrane and for ligand binding to the CGRP-receptor (McLatchie, L. M. et al, *Nature* 1998, 393, 333-339). RCP is required for signal transduction (Evans B. N. et al., *J Biol. Chem.* 2000, 275, 31438-43). There are known species-specific differences in binding of small molecule antagonists to the CGRP-receptor with typically greater affinity seen for antagonism of the human receptor than for other species (Brain, S. D. et al, *TiPS* 2002, 23, 51-53). The amino acid sequence of RAMP 1 determines the species selectivity, in particular, the amino acid residue Trp74 is responsible for the phenotype of the human receptor (Mallee et al. *J Biol Chem* 2002, 277, 14294-8).

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. *CNS Drugs* 2001; 15(10): 745-53; Williamson, D. J. *Microsc. Res. Tech.* 2001, 53, 167-178.; Grant, A. D. Brit. J. Pharmacol. 2002, 135, 356-362.). Serum levels of CGRP are elevated during migraine (Goadsby P J, et al. *Ann Neurol* 1990; 28: 183-7) and treatment with anti-migraine drugs returns CGRP levels to normal coincident with alleviation of headache (Gallai V. et al. *Cephalalgia* 1995; 15: 384-90). Migraineurs exhibit elevated basal CGRP levels compared to controls (Ashina M, et al., Pain. 2000; 86(1-2):133-8.2000). Intravenous CGRP infusion produces lasting headache in migraineurs (Lassen L H, et al. *Cephalalgia.* 2002 February; 22(1):54-61). Preclinical studies in dog and rat report that systemic CGRP blockade with the peptide antagonist CGRP(8-37) does not alter resting systemic hemodynamics nor regional blood flow (Shen, Y-T. et al, *J Pharmacol Exp Ther* 2001, 298, 551-8). Thus, CGRP-receptor antagonists may present a novel treatment for migraine that avoids the cardiovascular liabilities of active vasoconstriction associated with non-selective 5-HT1B/1D agonists, 'triptans' (e.g., sumatriptan).

There are various in vivo migraine models known in the literature (see De Vries, P. et al, *Eur J Pharmacol* 1999, 375, 61-74). Some electrically stimulate the trigeminal ganglion and measure dilation of the intracranial vessels which they innervate (e.g., Williamson et al. *Cephalalgia* 1997 17:518-24). Since facial arteries are also innervated by the trigeminal nerve, other models study changes in facial blood flow induced by electrical trigeminal activation (e.g., Escott et al. *Brain Res* 1995 669:93). Alternatively, other peripheral nerves (e.g., saphenous) and vascular beds (e.g., abdominal blood flow) are also studied (e.g., Escott et al. *Br J Pharmacol* 1993 110, 772-6;). All models have been shown to be blocked by pretreatment with the peptide antagonist CGPR(8-37) a peptide fragment that is absent the $1^{st}$ seven residues, or by a small molecule CGRP-receptor antagonist. In some instances, exogenous CGRP has been used as a stimulus. However, these models are all invasive terminal procedures, and none have shown the clinically important abortive effect of reversing an established increase in artery dilation or increased blood flow using post-treatment of a CGRP-receptor antagonist. Williamson et al. Cephalalgia 1997 17:518-24, and Williamson et al. Cephalalgia. 1997 17:525-31: used inter alia i.v. CGRP as a stimulus to increase intracranial dural artery diameter in sodium pentobarb anesthetized rats employing a terminal 'intravital' procedure that involved drilling to thin the skull and the creation of a closed cranial window to visualize dural arteries. The effect was blocked by pretreatment with i.v. CGRP(8-37). Escott et al. Brain Res 1995 669:93; inter alia drilled into the rat skull and used brain electrodes to electrically stimulate the trigeminal ganglion and measured laser Doppler facial blood flow in a terminal procedure in sodium pentobarb anesthetized rats involving neuromuscular blockade, tracheal intubation and artificial ventilation. The effect was blocked by pretreatment with CGRP(8-37). Escott et al. *Br J Pharmacol* 1993 110, 772-6; inter alia used intradermal (i.d.) CGRP as the stimulus to increase blood flow in rat abdominal skin of sodium pentobarb anesthetized animals outfitted with cannulated jugular veins for anesthetic and drug delivery. The effect was blocked by pretreatment with i.v. CGRP(8-37). Chu et al. *Neurosci*

Lett 2001 310, 169-72 used inter alia i.d. CGRP as the stimulus in rats and measured laser Doppler changes in blood flow in the skin of the back in a terminal method using sodium pentobarb anesthetized and tracheal cannulated animals; and showed pretreatment blockade by continuous release of CGRP(8-37) from subcutaneously (s.c.) implanted osmotic pumps. Hall et al *Br J Pharmacol* 1995 114, 592-7 and Hall et al *Br J Pharmacol* 1999 126, 280-4 inter alia used topical CGRP to increase hamster cheek pouch arteriole diameter, and i.d. CGRP to increase blood flow in rat dorsal skin of sodium pentobarb anesthetized animals outfitted with cannulated jugular veins for anesthetic and drug delivery. The effect was blocked by pretreatment with i.v. CGRP(8-37). Doods et al. Br J. Pharmacol. 2000 February; 129(3):420-3 inter alia drilled into the skull of the marmoset (new world monkey) and used brain electrodes to produce electrical stimulation of the trigeminal ganglion and measured facial blood flow in an invasive terminal procedure involving neuromuscular blockade and artificial ventilation of sodium pentobarbital anesthetized primates. Increase in flow was blocked by pre-treatment of a small molecule CGRP antagonist. See also WO 03/272252 Isolated DNA Molecules Encoding Humanized Calcitonin Gene-Related Peptide Receptor, Related Non-Human Transgenic Animals and Assay Methods. Thus the method of the present invention procedure being inter alia a non-invasive survival model in primates measuring exogenous CGRP-induced changes in facial blood flow and demonstrating pre- and post-treatment effects of peptide and small molecule CGRP antagonists in spontaneously breathing isoflurane anesthetized marmosets who recover from the procedure offers significant advantages.

A number of non-peptidic, small molecule CGRP-receptor antagonists have been recently reported. WO 97/09046 and equivalents disclose inter alia quinine and quinidine related compounds which are ligands, in particular antagonists, of CGRP-receptor. WO 98/09630 and WO 98/56779 and equivalents disclose inter alia variously substituted, nitrobenzamide compounds as CGRP-receptor antagonists. WO 01/32649, WO 01/49676, and WO 01/32648 and equivalents disclose inter alia a series of 4-oxobutanamides and related cyclopropane derivatives as CGRP-receptor antagonists. WO 00/18764, WO 98/11128 and WO 00/55154 and equivalents disclose inter alia benzimidazolinyl piperidines as antagonists to CGRP-receptor. Unrelated to CGRP, a series of somatostatin antagonists have been disclosed in WO 99/52875 and WO 01/25228 and equivalents. See also U.S. Pat. No. 6,344,449, U.S. Pat. No. 6,313,097, U.S. Pat. No. 6,521,609, U.S. Pat. No. 6,552,043, U.S. 20030181462, U.S. 20030191068 and WO 03/076432 and related applications. Thus, novel CGRP-receptor antagonists effective for the treatment of neurogenic inflammation, migraine and other disorders would be greatly advantageous.

SUMMARY OF THE INVENTION

Thus according to a first embodiment of the first aspect of the present invention are provided compounds of Formula (I)

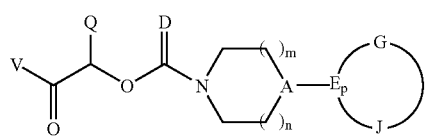

and pharmaceutically acceptable salts and solvates thereof wherein

V is —N($R^1$)($R^2$) or $OR^4$;

$R^4$ is H, $C_{1-6}$alkyl, $C_{1-4}$haloalkyl or ($C_{1-4}$alkylene)$_{0-1}R^{4'}$ $R^{4'}$ is $C_{3-7}$cycloalkyl, phenyl, adamantyl, quinuclidyl, azabicyclo[2.2.1]heptyl, azetidinyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino or dioxolanyl; and $R^{4'}$ is optionally substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-3}$alkylamino, $C_{1-3}$dialkylamino, ($C_{1-3}$alkyl)$_{0-2}$ureido, phenyl and benzyl; and $R^{4'}$ optionally contains 1 or 2 carbonyls wherein the carbon atom of said carbonyl is a member of the ring structure of $R^{4'}$;

$R^1$ and $R^2$ are each independently $L^1$, wherein $L^1$ is selected from the group consisting of H, $C_{1-6}$alkyl, $C_{2-6}$alkenyl, $C_{2-6}$alkynyl, —$C_{1-6}$alkylene-amino($C_{1-3}$alkyl)$_2$, $C_{3-7}$cycloalkyl, phenyl, azetidinyl, adamantyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino and dioxolanyl; and $R^1$ and $R^2$ are each optionally and independently substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-3}$alkylamino, $C_{1-3}$dialkylamino, ($C_{1-3}$alkyl)$_{0-2}$ureido, phenyl and benzyl;

$R^1$ and $R^2$ optionally and independently contain 1 or 2 carbonyls wherein the carbon atom of said carbonyl is a member of the heterocycles comprising $R^1$ and $R^2$;

wherein $L^1$ is optionally and independently interrupted from the nitrogen to which it is attached by $L^2$, wherein $L^2$ is independently $C_{1-3}$alkylene or $C_{1-3}$alkylidene; or $R^1$ and $R^2$ together with the nitrogen to which they are attached form X, wherein X is azetidinyl, pyrrolyl, pyrrolinyl, pyrrolidinyl, imidazolinyl, imidazolidinyl, pyrazolinyl, pyrazolidinyl, azepinyl, diazepinyl, piperazinyl, piperidinyl, morpholino or thiomorpholino;

wherein X is optionally substituted with Y, wherein Y is dioxolanyl, $C_{1-9}$alkyl, $C_{2-9}$alkenyl, $C_{2-9}$alkynyl, $C_{1-4}$alkylamino, $C_{1-4}$dialkylamino, $C_{1-4}$alkoxy, $C_{3-7}$cycloalkyl, phenyl, azetidinyl, furanyl, thienyl, pyrrolyl, pyrrolinyl, pyrrolidinyl, pyrrolidinonyl, imidazolyl, imidazolinyl, imidazolidinyl, imidazolidinonyl, pyrazolyl, pyrazolinyl, pyrazolidinyl, azepinyl, diazepinyl, pyridyl, pyrimidinyl, dihydrobenzimidazolonyl, piperazinyl, piperidinyl, morpholino, benzothiazolyl, benzisothiazolyl or thiomorpholino; and wherein X and Y are optionally interrupted with Z, wherein Z is —NHC(O)O—, —NHC(O)NH—, NC(O)$NH_2$, —NH—, —C$_{1-3}$alkylene-, —C$_{1-3}$alkylene-, —C$_{1-3}$alkenylene-NHC(O)O—C$_{1-3}$alkylene-; and optionally and independently substituted with 1 or 2 of the same or different substituents selected from the group consisting of halo, C$_{1-4}$alkyl, amino, C$_{1-3}$alkylamino, —C$_{1-6}$alkylene-amino (C$_{1-3}$alkyl)$_2$, (C$_{1-3}$alkyl)$_{0-2}$ureido, phenyl and benzyl;

X and Y optionally and independently contain 1 or 2 carbonyls wherein the carbon atom of said carbonyl is a member of the heterocycles comprising X and Y;

provided that if X is substituted with Y, and
 if X and Y are not interrupted with Z, then
 X and Y optionally share one carbon atom and together form a spirocyclic moiety;

Q is Q' or Q";
 wherein
 Q' is (S$^y$)$_s$R$^3$; and
 Q" is NH(S$^y$)$_s$R$^3$, NHC(O)(S$^y$)$_s$R$^3$, NHC(O)O(S$^y$)$_s$R$^3$, NHC(O)NH(S$^y$)$_s$R$^3$, O(S$^y$)$_s$R$^3$, (S$^y$)$_n$NHR$^3$, (S$^y$)$_s$NHC(O)R$^3$, (S$^y$)$_s$NHC(O)OR$^{3'}$, (S$^y$)$_s$NHC(O)NHR$^3$ or (S$^y$)$_s$OR$^3$;
 wherein S$^y$ is C$_{1-3}$alkylene or C$_{1-3}$alkylidene and s is 0 or 1;

R$^3$ is R$^{3a}$ or R$^{3b}$
 wherein
 R$^{3a}$ is
 (i) a heterocycle having two fused rings with 5 to 7 members in each of said rings, said heterocycle containing one to five of the same or different heteroatoms selected from the group consisting of O, N and S and said heterocycle optionally containing 1 or 2 carbonyls wherein the carbon atom of said carbonyl is a member of said fused rings;
 (ii) a 4 to 6 membered heterocycle containing one to three of the same or different heteroatoms selected from the group consisting of O, N and S, optionally containing 1 to 2 carbonyls, wherein the carbon atom of said carbonyl is a member of said 4 to 6 membered heterocycle;
 (iii) C$_{3-7}$cycloalkyl;
 (iv) carbazolyl, fluorenyl, phenyl, —O-phenyl, —O—C$_{1-4}$alkylene-phenyl, or napthyl; or
 (v) C$_{1-8}$alkyl, C$_{2-7}$alkenyl, —C(O)R$^3$, CHC(O)O—R$^3$, CH(CH$_3$)C(O)O—R$^{3'}$, —C(O)O—R$^{3'}$ or C$_{2-7}$alkynyl; and
 wherein R$^3$, is optionally substituted with 1 to 3 of the same or different substituents selected from the group consisting of benzyl, phenyl, —O-phenyl, —O—C$_{1-3}$alkylenephenyl, —C$_{1-3}$alkylene-OC(O)-phenyl, cyano, amino, nitro, halo, C$_{1-6}$alkyl, C$_{1-3}$mono-bi-trihaloalkyl, C$_{1-3}$mono-bi-tri-haloalkyloxy, (C$_{1-3}$alkyl)$_{1-2}$amine,
 —OR$^{3'}$, —C(O)R$^{3'}$, —C(O)O—R$^{3'}$, —O—C(O)R$^{3'}$, —N(R$^{3'}$)—C(O)N(R$^{3'}$)$_2$, —N(R$^{3'}$)C(O)(R$^{3'}$)$_2$, —N(R$^{3'}$)C(O)N(R$^{3'}$)$_2$, —N(R$^{3'}$)C(O)OR$^{3'}$, —O—C(O)N(R$^{3'}$)$_2$, —N(R$^{3'}$)SO$_2$R$^{3'}$, —SO$_2$N(R$^{3'}$)$_2$ and —SO$_2$R$^{3'}$;
 R$^{3'}$ is H or —C$_{1-6}$alkyl;
 provided that if R$^{3a}$ is, —C(O)R$^3$, CHC(O)O—R$^{3'}$, CH(CH$_3$)C(O)O—R$^{3'}$ or —C(O)O—R$^{3'}$, then said —C(O)R$^{3'}$, CHC(O)O—R$^{3'}$, CH(CH$_3$)C(O)O—R$^{3'}$ or —C(O)O—R$^{3'}$ are unsubstituted;
 R$^{3b}$ is R$^{3a}$ but is not phenyl, 1-naphthyl, 2-naphthyl, 1,2,3,4-tetrahydro-1-naphthyl, 1H-indol-3-yl, 1-methyl-1H-indol-3-yl, 1-formyl-1H-indol-3-yl, 1-(1,1-dimethylethoxycarbonyl)-1H-indol-3-yl, 4-imidazolyl, 1-methyl-4-imidazolyl, 2-thienyl, 3-thienyl, thiazolyl, 1H-indazol-3-yl, 1-methyl-1H-indazol-3-yl, benzo[b]fur-3-yl, benzo[b]thien-3-yl, pyridinyl, quinolinyl or isoquinolinyl; optionally substituted in the carbon skeleton with mono-, di- or trisubstituted by fluorine, chlorine or bromine atoms or by branched or unbranched alkyl groups, C$_{3-8}$-cycloalkyl groups, phenylalkyl groups, alkenyl, alkoxy, phenyl, phenylalkoxy, trifluoromethyl, alkoxycarbonylalkyl, carboxyalkyl, alkoxycarbonyl, carboxy, dialkylaminoalkyl, dialkylaminoalkoxy, hydroxy, nitro, amino, acetylamino, propionylamino, benzoyl, benzoylamino, benzoylmethylamino, methylsulphonyloxy, aminocarbonyl, alkylaminocarbonyl, dialkylaminocarbonyl, alkanoyl, cyano, tetrazolyl, phenyl, pyridinyl, thiazolyl, furyl, trifluoromethoxy, trifluoromethylthio, trifluoromethylsulphinyl- or trifluoromethylsulphonyl groups;
 wherein said substituents may be the same or different and the above-mentioned benzoyl, benzoylamino- and benzoylmethylamino groups may in turn additionally be substituted in the phenyl moiety by a fluorine, chlorine or bromine atom, or by an alkyl, trifluoromethyl, amino or acetylamino group;

D is O, NCN or NSO$_2$C$_{1-3}$alkyl;
A is C, N, CH or COH;
m and n are independently 0, 1 or 2;
 provided that
 if m and n are 0, then A is not N;
 if m is 2, then n is not 2; or
 if n is 2, then m is not 2;
E is N, CH or C;
p is 0 or 1;
 if p is 1, then G, J and E together form A$^x$ or A$^y$;
 A$^x$ is a fused heterocycle having two fused rings with 5 to 7 members in each of said rings, said heterocycle containing one to four of the same or different heteroatoms selected from the group consisting of O, N and S; and
 optionally containing 1 or 2 carbonyls wherein the carbon atom of said carbonyl is a member of said fused heterocycle;
 A$^y$ is a 4 to 6 membered heterocycle containing one to three heteroatoms selected from the group consisting of O, N and S; and
 optionally containing 1 to 2 carbonyls, wherein the carbon atom of said carbonyl is a member of said 4 to 6 membered heterocycle;
 wherein A$^x$ and A$^y$ are optionally substituted with C$_{1-4}$alkyl, C$_{1-4}$alkoxy, C$_{1-4}$haloalkyl, cyano, C$_{3-7}$cycloalkyl, phenyl, halophenyl, halo, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl or morpholino; or
 if p is 0 such that G and J are each attached to A, then A is C, and G, J and A together form a spirocyclic ring system with said rings of said system containing A and wherein G, J and A together are GJA' or GJA";
 wherein
 GJA' is A$^x$ or A$^y$; and
 GJA" is A$^x$ or A$^y$;
 provided that
 A$^x$ is not a 1,3-diaza-fused heterocycle; and
 A$^y$ is not a 1,3-diaza-heterocycle;

and further provided that
   if Q is Q", then $R^3$ is $R^{3a}$; and
   if Q is Q', then
      $R^3$ is $R^{3b}$; or
      $R^3$ is $R^{3a}$, p is 0 and G, J and A together form GJA".

According to another embodiment of the first aspect of the present invention are provided compounds according to the first embodiment of the first aspect of the present invention wherein Q is Q' and $R^3$ is $R^{3b}$.

According to another embodiment of the first aspect of the present invention are provided compounds according to the first embodiment of the first aspect of the present invention wherein Q is Q', $R^3$ is $R^{3a}$ and p is 0 such that G, J and A together form GJA".

According to another embodiment of the first aspect of the present invention are provided compounds according to the first embodiment of the first aspect of the present invention wherein Q is Q' and Q' is $(S^y)_s R^3$ and s is 0.

According to another embodiment of the first aspect of the present invention are provided compounds according to the first embodiment of the first aspect of the present invention wherein Q is Q' and Q' is $(S^y)_s R^3$, $S^y$ is $C_{1-3}$ alkylene and s is 1.

According to another embodiment of the first aspect of the present invention are provided compounds according to the first embodiment of the first aspect of the present invention wherein Q is Q' and Q' is $(S^y)_s R^3$, $S^y$ is methylene and s is 1.

According to another embodiment of the first aspect of the present invention are provided compounds according to the first embodiment of the first aspect of the present invention wherein Q is Q' and Q' is $(S^y)_s R^3$, $S^y$ is $C_{1-3}$ alkylidene and s is 1.

According to another embodiment of the first aspect of the present invention are provided compounds according to the first embodiment of the first aspect of the present invention wherein Q is Q'.

According to another embodiment of the first aspect of the present invention are provided compounds according to the first embodiment of the first aspect of the present invention wherein Q is Q', Q' is $(S^y)_s R^3$, and s is 0.

According to another embodiment of the first aspect of the present invention are provided compounds according to the first embodiment of the first aspect of the present invention wherein Q is Q', Q' is $(S^y)_s R^3$, $S^y$ is $C_{1-3}$ alkylene and s is 1.

According to another embodiment of the first aspect of the present invention are provided compounds according to the first embodiment of the first aspect of the present invention wherein Q is Q', Q' is $(S^y)_s R^3$, $S^y$ is $C_{1-3}$ alkylidene and s is 1.

According to another embodiment of the first aspect of the present invention are provided compounds according to the first embodiment of the first aspect of the present invention wherein Q is Q".

According to another embodiment of the first aspect of the present invention are provided compounds according to the first embodiment of the first aspect of the present invention wherein Q is Q" and Q" is $NH(S^y)_s R^3$.

According to another embodiment of the first aspect of the present invention are provided compounds according to the first embodiment of the first aspect of the present invention wherein Q is Q" and Q" is $NH(S^y)_s R^3$ and s is 0.

According to another embodiment of the first aspect of the present invention are provided compounds according to the first embodiment of the first aspect of the present invention wherein Q is Q" and Q" is $NH(S^y)_s R^3$, $S^y$ is $C_{1-3}$ alkylene and s is 1.

According to another embodiment of the first aspect of the present invention are provided compounds according to the first embodiment of the first aspect of the present invention wherein Q is Q" and Q" is $NH(S^y)_s R^3$, $S^y$ is $C_{1-3}$ alkylidene and s is 1.

According to another embodiment of the first aspect of the present invention are provided compounds according to the first embodiment of the first aspect of the present invention wherein Q is Q" and Q" is $NHC(O)(S^y)_s R^3$.

According to another embodiment of the first aspect of the present invention are provided compounds according to the first embodiment of the first aspect of the present invention wherein Q is Q" and Q" is $NHC(O)(S^y)_s R^3$ and s is 0.

According to another embodiment of the first aspect of the present invention are provided compounds according to the first embodiment of the first aspect of the present invention wherein Q is Q" and Q" is $NHC(O)(S^y)_s R^3$, $S^y$ is $C_{1-3}$ alkylene and s is 1.

According to another embodiment of the first aspect of the present invention are provided compounds according to the first embodiment of the first aspect of the present invention wherein Q is Q" and Q" is $NHC(O)(S^y)_s R^3$, $S^y$ is $C_{1-3}$ alkylidene and s is 1.

According to another embodiment of the first aspect of the present invention are provided compounds according to the first embodiment of the first aspect of the present invention wherein Q is Q" and Q" is $NHC(O)O(S^y)_s R^3$.

According to another embodiment of the first aspect of the present invention are provided compounds according to the first embodiment of the first aspect of the present invention wherein Q is Q" and Q" is $NHC(O)O(S^y)_s R^3$ and s is 0.

According to another embodiment of the first aspect of the present invention are provided compounds according to the first embodiment of the first aspect of the present invention wherein Q is Q" and Q" is $NHC(O)O(S^y)_s R^3$, $S^y$ is $C_{1-3}$ alkylene and s is 1.

According to another embodiment of the first aspect of the present invention are provided compounds according to the first embodiment of the first aspect of the present invention wherein Q is Q" and Q" is $NHC(O)O(S^y)_s R^3$, $S^y$ is $C_{1-3}$ alkylidene and s is 1.

According to another embodiment of the first aspect of the present invention are provided compounds according to the first embodiment of the first aspect of the present invention wherein Q is Q" and Q" is $NHC(O)NH(S)_s R^3$.

According to another embodiment of the first aspect of the present invention are provided compounds according to the first embodiment of the first aspect of the present invention wherein Q is Q" and Q" is $NHC(O)NH(S^y)_s R^3$ and s is 0.

According to another embodiment of the first aspect of the present invention are provided compounds according to the first embodiment of the first aspect of the present invention wherein Q is Q" and Q" is $NHC(O)NH(S^y)_s R^3$, $S^y$ is $C_{1-3}$ alkylene and s is 1.

According to another embodiment of the first aspect of the present invention are provided compounds according to the first embodiment of the first aspect of the present invention wherein Q is Q" and Q" is $NHC(O)NH(S^y)_s R^3$, $S^y$ is $C_{1-3}$ alkylidene and s is 1.

According to another embodiment of the first aspect of the present invention are provided compounds according to the first embodiment of the first aspect of the present invention wherein V is $OR^4$.

According to another embodiment of the first aspect of the present invention are provided compounds according to the first embodiment of the first aspect of the present invention wherein V is $OR^4$ and $R^4$ is $C_{1-6}$ alkyl.

According to another embodiment of the first aspect of the present invention are provided compounds according to the first embodiment of the first aspect of the present invention wherein V is —N($R^1$)($R^2$).

According to another embodiment of the first aspect of the present invention are provided compounds according to the first embodiment of the first aspect of the present invention wherein V is —N($R^1$)($R^2$) or $OR^4$;

$R^4$ is H, $C_{1-6}$alkyl, $C_{1-4}$haloalkyl, ($C_{1-4}$alkylene)$_{0-1}R^{4'}$ $R^{4'}$ is $C_{3-7}$cycloalkyl, phenyl, adamantyl, quinuclidyl, azabicyclo[2.2.1]heptyl, azetidinyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino or dioxolanyl; and $R^{4'}$ is optionally substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-3}$alkylamino, $C_{1-3}$dialkylamino, ($C_{1-3}$alkyl)$_{0-2}$ureido, phenyl and benzyl;

$R^{4'}$ optionally contains 1 or 2 carbonyls wherein the carbon atom of said carbonyl is a member of the ring structure of $R^{4'}$;

$R^1$ and $R^2$ are each independently $L^1$, wherein $L^1$ is selected from the group consisting of H, $C_{1-6}$alkyl, —$C_{1-6}$alkylene-amino($C_{1-3}$alkyl)$_2$, $C_{3-7}$cycloalkyl, phenyl, adamantyl, azetidinyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino and dioxolanyl; and $R^1$ and $R^2$ are each optionally and independently substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-3}$alkylamino, $C_{1-3}$dialkylamino, ($C_{1-3}$alkyl)$_{0-2}$ureido, phenyl and benzyl;

$R^1$ and $R^2$ optionally and independently contain 1 or 2 carbonyls wherein the carbon atom of said carbonyl is a member of the heterocycles comprising $R^1$ and $R^2$;

wherein $L^1$ is optionally interrupted from the nitrogen to which it is attached by $L^2$, wherein $L^2$ is $C_{1-3}$alkylene; or $R^1$ and $R^2$ together with the nitrogen to which they are attached form X, wherein X is azetidinyl, pyrrolinyl, pyrrolidinyl, imidazolinyl, imidazolidinyl, pyrazolinyl, pyrazolidinyl, azepinyl, diazepinyl, piperazinyl, piperidinyl, morpholino or thiomorpholino;

wherein X is optionally substituted with Y, wherein Y is dioxolanyl, $C_{1-4}$alkyl, $C_{1-4}$alkylamino, $C_{1-4}$dialkylamino, $C_{1-4}$alkoxy, $C_{3-7}$cycloalkyl, phenyl, azetidinyl, pyrrolyl, pyrrolinyl, pyrrolidinyl, pyrrolidinonyl, imidazolyl, imidazolinyl, imidazolidinyl, imidazolidinonyl, pyrazolyl, pyrazolinyl, pyrazolidinyl, azepinyl, diazepinyl, pyridyl, pyrimidinyl, dihydrobenzimidazolonyl, piperazinyl, piperidinyl, morpholino, benzothiazolyl, benzisothiazolyl or thiomorpholino;

and wherein X and Y are optionally interrupted with Z, wherein Z is —NHC(O)O—, —NHC(O)NH—, NC(O)$NH_2$, —NH—, —$C_{1-3}$alkylene-, —$C_{1-3}$alkylene-NHC(O)O—$C_{1-3}$alkylene-; and optionally and independently substituted with 1 or 2 of the same or different substituents selected from the group consisting of halo, $C_{1-4}$alkyl, amino, $C_{1-3}$alkylamino, —$C_{1-6}$alkylene-amino($C_{1-3}$alkyl)$_2$, ($C_{1-3}$alkyl)$_{0-2}$ureido, phenyl and benzyl;

X and Y optionally and independently contain 1 or 2 carbonyls wherein the carbon atom of said carbonyl is a member of the heterocycles comprising X and Y;

provided that if X is substituted with Y, and if X and Y are not interrupted with Z, then X and Y optionally share one carbon atom and together form a spirocyclic moiety.

According to another embodiment of the first aspect of the present invention are provided compounds according to the first embodiment of the first aspect of the present invention wherein $R^4$ is H, $C_{1-6}$alkyl, $C_{1-4}$haloalkyl or ($C_{1-4}$alkylene)$_{0-1}$$R^{4'}$; $R^{4'}$ is $C_{3-7}$cycloalkyl, phenyl, adamantyl, quinuclidyl, azabicyclo[2.2.1]heptyl, azetidinyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino or dioxolanyl; and $R^{4'}$ is optionally substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-3}$alkylamino, $C_{1-3}$dialkylamino, ($C_{1-3}$alkyl)$_{0-2}$ureido, phenyl and benzyl.

According to another embodiment of the first aspect of the present invention are provided compounds according to the first embodiment of the first aspect of the present invention wherein $R^4$ is H, $C_{1-6}$alkyl, $C_{1-4}$haloalkyl or ($C_{1-4}$alkylene)$_{0-1}$$R^{4'}$; $R^{4'}$ is $C_{3-7}$cycloalkyl, phenyl, adamantyl, quinuclidyl, azabicyclo[2.2.1]heptyl, azetidinyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino or dioxolanyl.

According to another embodiment of the first aspect of the present invention are provided compounds according to the first embodiment of the first aspect of the present invention wherein $R^4$ is H, $C_{1-6}$alkyl or ($C_{1-4}$alkylene)$_{0-1}$$R^{4'}$; $R^{4'}$ is $C_{3-7}$cycloalkyl.

According to another embodiment of the first aspect of the present invention are provided compounds according to the first embodiment of the first aspect of the present invention wherein V is —N($R^1$)($R^2$) and $R^1$ and $R^2$ are each independently $L^1$, wherein $L^1$ is selected from the group consisting of H, $C_{1-6}$alkyl, —$C_{1-6}$alkylene-amino($C_{1-3}$alkyl)$_2$, $C_{3-7}$cycloalkyl, phenyl, azetidinyl, adamantyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino and dioxolanyl; or
$R^1$ and $R^2$ together with the nitrogen to which they are attached form X,
wherein X is azetidinyl, pyrrolinyl, pyrrolidinyl, imidazolinyl, imidazolidinyl, pyrazolinyl, pyrazolidinyl, azepinyl, diazepinyl, piperazinyl, piperidinyl, morpholino or 0thiomorpholino;
wherein X is substituted with Y, wherein Y is dioxolanyl, $C_{1-4}$alkyl, $C_{1-4}$alkoxy, $C_{3-7}$cycloalkyl, phenyl, azetidinyl, pyrrolyl, pyrrolinyl, pyrrolidinyl, pyrrolidinonyl, imidazolyl, imidazolinyl, imidazolidinyl, imidazolidinonyl, pyrazolyl, pyrazolinyl, pyrazolidinyl, azepinyl, diazepinyl, pyridyl, pyrimidinyl, dihydrobenzimidazolonyl, piperazinyl, piperidinyl, morpholino, benzothiazolyl, benzisothiazolyl or thiomorpholino;
and wherein X and Y optionally share one carbon atom and together form a spirocyclic moiety.

According to another embodiment of the first aspect of the present invention are provided compounds according to the first embodiment of the first aspect of the present invention wherein V is —$N(R^1)(R^2)$ and
$R^1$ and $R^2$ are each independently $L^1$, wherein $L^1$ is selected from the group consisting of H, $C_{1-6}$alkyl, or
$R^1$ and $R^2$ together with the nitrogen to which they are attached form X,
wherein X is piperidinyl or morpholino;
wherein X is substituted with Y, wherein Y is dioxolanyl, $C_{1-4}$alkyl or piperidinyl;
and wherein X and Y optionally share one carbon atom and together form a spirocyclic moiety.

According to another embodiment of the first aspect of the present invention are provided compounds according to the first embodiment of the first aspect of the present invention wherein V is —$N(R^1)(R^2)$ and wherein $R^1$ and $R^2$ are each independently $L^1$, wherein $L^1$ is selected from the group consisting of H, $C_{1-6}$alkyl.

According to another embodiment of the first aspect of the present invention are provided compounds according to the first embodiment of the first aspect of the present invention wherein V is —$N(R^1)(R^2)$ and wherein
$R^1$ and $R^2$ together with the nitrogen to which they are attached form X,
wherein X is piperidinyl, piperazinyl or morpholino;
wherein X is substituted with Y, wherein Y is dioxolanyl, phenyl, pyridyl, piperazinyl, piperidinyl or $C_{1-4}$alkyl;
and wherein X and Y optionally share one carbon atom and together form a spirocyclic moiety.

According to another embodiment of the first aspect of the present invention are provided compounds according to the first embodiment of the first aspect of the present invention wherein V is —$N(R^1)(R^2)$ and wherein
$R^1$ and $R^2$ together with the nitrogen to which they are attached form X,
wherein X is piperidinyl;
wherein X is substituted with Y, wherein Y is piperidinyl.

According to another embodiment of the first aspect of the present invention are provided compounds according to the first embodiment of the first aspect of the present invention wherein V is —$N(R^1)(R^2)$ and wherein
$R^1$ and $R^2$ together with the nitrogen to which they are attached form X,
wherein X is morpholino;
wherein X is substituted with Y, wherein Y is $C_{1-4}$alkyl.

According to another embodiment of the first aspect of the present invention are provided compounds according to the first embodiment of the first aspect of the present invention wherein V is —$N(R^1)(R^2)$ and wherein
$R^1$ and $R^2$ together with the nitrogen to which they are attached form X,
wherein X is piperidinyl;
wherein X is substituted with Y, wherein Y is $C_{1-4}$alkyl.

According to another embodiment of the first aspect of the present invention are provided compounds according to the first embodiment of the first aspect of the present invention wherein V is —$N(R^1)(R^2)$ and wherein
$R^1$ and $R^2$ together with the nitrogen to which they are attached form X,
wherein X is piperidinyl;
wherein X is substituted with Y, wherein Y is dioxolanyl;
and wherein X and Y share one carbon atom and together form a spirocyclic moiety.

According to another embodiment of the first aspect of the present invention are provided compounds according to the first embodiment of the first aspect of the present invention wherein X and Y are not interrupted with Z.

According to another embodiment of the first aspect of the present invention are provided compounds according to the first embodiment of the first aspect of the present invention wherein X and Y are not interrupted with Z; and X and Y share one carbon atom and together form a spirocyclic moiety.

According to another embodiment of the first aspect of the present invention are provided compounds according to the first embodiment of the first aspect of the present invention wherein $R^3$ is $R^{3a}$.

According to another embodiment of the first aspect of the present invention are provided compounds according to the first embodiment of the first aspect of the present invention wherein $R^3$ is $R^{3b}$.

According to another embodiment of the first aspect of the present invention are provided compounds according to the first embodiment of the first aspect of the present invention wherein $R^{3a}$ is a heterocycle having two fused rings with 5 to 7 members in each of said rings, said heterocycle containing one to five of the same or different heteroatoms selected from the group consisting of O, N and S.

According to another embodiment of the first aspect of the present invention are provided compounds according to the first embodiment of the first aspect of the present invention wherein $R^{3a}$ is a heterocycle having two fused rings with 5 to 7 members in each of said rings, said heterocycle containing one to five of the same or different heteroatoms selected from the group consisting of O, N and S and said heterocycle optionally containing 1 or 2 carbonyls wherein the carbon atom of said carbonyl is a member of said fused rings.

According to another embodiment of the first aspect of the present invention are provided compounds according to the first embodiment of the first aspect of the present invention wherein $R^{3a}$ is a heterocycle having two fused rings with 5 to 7 members in each of said rings, said heterocycle containing one to five of the same or different heteroatoms selected from the group consisting of O, N and S and said heterocycle optionally containing 1 or 2 carbonyls wherein the carbon atom of said carbonyl is a member of said fused rings; wherein $R^{3a}$ is optionally substituted with 1 to 3 of the same or different substituents selected from the group consisting of benzyl, phenyl, —O-phenyl, —O—$C_{1-3}$alkylphenyl, —$C_{1-}$ ₃alkylene-OC(O)-phenyl, cyano, amino, nitro, halo, $C_{1-3}$mono-bi-tri-haloalkyl, $C_{1-3}$mono-bi-tri-haloalkyloxy, $C_{1-6}$alkoxy, $(C_{1-3}alkyl)_{1-2}$amine, —OR³', —C(O)R³, —C(O)O—R³', —O—C(O)R³', —N(R³')₂, —C(O)N(R³')₂, —N(R³')C(O)(R³')₂, —N(R³')C(O)N(R³')₂, —N(R³')C(O)OR³', —O—C(O)N(R³')₂, —N(R³')SO₂R³, —SO₂N(R³')₂ and —SO₂R³'; R³' is H or —C₁₋₆alkyl.

According to another embodiment of the first aspect of the present invention are provided compounds according to the first embodiment of the first aspect of the present invention wherein $R^{3a}$ is a 4 to 6 membered heterocycle containing one to three of the same or different heteroatoms selected from the group consisting of O, N and S.

According to another embodiment of the first aspect of the present invention are provided compounds according to the first embodiment of the first aspect of the present invention wherein $R^{3a}$ is a 4 to 6 membered heterocycle containing one to three of the same or different heteroatoms selected from the group consisting of O, N and S, optionally containing 1 to 2 carbonyls, wherein the carbon atom of said carbonyl is a member of said 4 to 6 membered heterocycle.

According to another embodiment of the first aspect of the present invention are provided compounds according to the first embodiment of the first aspect of the present invention wherein $R^{3a}$ is a 4 to 6 membered heterocycle containing one to three of the same or different heteroatoms selected from the group consisting of O, N and S, optionally containing 1 to 2 carbonyls, wherein the carbon atom of said carbonyl is a member of said 4 to 6 membered heterocycle; wherein $R^{3a}$ is optionally substituted with 1 to 3 of the same or different substituents selected from the group consisting of benzyl, phenyl, —O-phenyl, —O—$C_{1-3}$alkylphenyl, —$C_{1-3}$alkylene-OC(O)-phenyl, cyano, amino, nitro, halo, $C_{1-3}$mono-bi-tri-haloalkyl, $C_{1-3}$mono-bi-tri-haloalkyloxy, $C_{1-6}$alkoxy, $(C_{1-3}$ alkyl$)_{1-2}$amine, —OR³', —C(O)R³', —C(O)O—R³', —O—C(O)R³, —N(R³')₂, —C(O)N(R³')₂, —N(R³')C(O)(R³')₂, —N(R³')C(O)N(R³')₂, —N(R³')C(O)OR³', —O—C(O)N(R³')₂, —N(R³')SO₂R³, —SO₂N(R³')₂ and —SO₂R³'; R³' is H or —C₁₋₆alkyl.

According to another embodiment of the first aspect of the present invention are provided compounds according to the first embodiment of the first aspect of the present invention wherein $R^{3a}$ is $C_{3-7}$cycloalkyl.

According to another embodiment of the first aspect of the present invention are provided compounds according to the first embodiment of the first aspect of the present invention wherein $R^{3a}$ is $C_{3-7}$cycloalkyl; wherein $R^{3a}$ is optionally substituted with 1 to 3 of the same or different substituents selected from the group consisting of benzyl, phenyl, —O-phenyl, —O—$C_{1-3}$alkylphenyl, —$C_{1-3}$alkylene-OC(O)-phenyl, cyano, amino, nitro, halo, $C_{1-3}$mono-bi-tri-haloalkyl, $C_{1-3}$mono-bi-tri-haloalkyloxy, $C_{1-6}$alkoxy, $(C_{1-3}alkyl)_{1-2}$amine, —OR³', —C(O)R³', —C(O)O—R³', —O—C(O)R³', —N(R³')₂, —C(O)N(R³')₂, —N(R³')C(O)(R³')₂, —N(R³')C(O)N(R³')₂, —N(R³')C(O)OR³', —O—C(O)N(R³')₂, —N(R³')SO₂R³, —SO₂N(R³')₂ and —SO₂R³'; R³' is H or —C₁₋₆alkyl.

According to another embodiment of the first aspect of the present invention are provided compounds according to the first embodiment of the first aspect of the present invention wherein $R^{3a}$ is carbazolyl, fluorenyl, phenyl, —O-phenyl, —O—$C_{1-4}$alklylene-phenyl, or napthyl.

According to another embodiment of the first aspect of the present invention are provided compounds according to the first embodiment of the first aspect of the present invention wherein $R^{3a}$ is carbazolyl, fluorenyl, phenyl, —O-phenyl, —O—$C_{1-4}$alklylene-phenyl, or napthyl; wherein $R^{3a}$ is optionally substituted with 1 to 3 of the same or different substituents selected from the group consisting of benzyl, phenyl, —O-phenyl, —O—$C_{1-3}$alkylphenyl, —$C_{1-3}$alkylene-OC(O)-phenyl, cyano, amino, nitro, halo, $C_{1-3}$mono-bi-tri-haloalkyl, $C_{1-3}$mono-bi-tri-haloalkyloxy, $C_{1-6}$alkoxy, $(C_{1-3}$ alkyl$)_{1-2}$amine, —OR³', —C(O)R³, —C(O)O—R³', —O—C(O)R³', —N(R³')₂, —C(O)N(R³')₂, —N(R³')C(O)(R³')₂, —N(R³')C(O)N(R³')₂, —N(R³')C(O)OR³', —O—C(O)N(R³')₂, —N(R³')SO₂R³, —SO₂N(R³')₂ and —SO₂R³'; R³' is H or —C₁₋₆alkyl.

According to another embodiment of the first aspect of the present invention are provided compounds according to the first embodiment of the first aspect of the present invention wherein $R^{3a}$ is $C_{1-8}$alkyl, $C_{2-7}$alkenyl, —C(O)R³, —C(O)O—R³' or $C_{2-7}$alkynyl.

According to another embodiment of the first aspect of the present invention are provided compounds according to the first embodiment of the first aspect of the present invention wherein $R^{3a}$ is $C_{1-8}$alkyl, $C_{2-7}$alkenyl, —C(O)R³', —C(O)O—R³' or $C_{2-7}$alkynyl; wherein $R^{3a}$ is optionally substituted with 1 to 3 of the same or different substituents selected from the group consisting of benzyl, phenyl, —O-phenyl, —O—$C_{1-3}$alkylphenyl, —$C_{1-3}$alkylene-OC(O)-phenyl, cyano, amino, nitro, halo, $C_{1-3}$mono-bi-tri-haloalkyl, $C_{1-3}$mono-bi-tri-haloalkyloxy, $C_{1-6}$alkoxy, $(C_{1-3}alkyl)_{1-2}$amine, —OR³', —C(O)R³', —C(O)O—R³', —O—C(O)R³, —N(R³')₂, —C(O)N(R³')₂, —N(R³')C(O)(R³')₂, —N(R³')C(O)N(R³')₂, —N(R³')C(O)OR³', —O—C(O)N(R³')₂, —N(R³')SO₂R³, —SO₂N(R³')₂ and —SO₂R³'; R³' is H or —C₁₋₆alkyl; provided that if $R^{3a}$ is —C(O)R³, CHC(O)O—R³', CH(CH₃)C(O)O—R³' or —C(O)O—R³', then said —C(O)R³', CHC(O)O—R³', CH(CH₃)C(O)O—R³' or —C(O)O—R³' are unsubstituted.

According to another embodiment of the first aspect of the present invention are provided compounds according to the first embodiment of the first aspect of the present invention wherein R³ is R³' and $R^{3a}$ is phenyl, hydroxyphenyl, azetidinyl, napthyl, $C_{1-6}$alkyl, $C_{2-6}$alkenyl, $C_{2-6}$alkynl, dihydroquinolinonyl, hydroquinolinonyl, quinolinyl, dihydroisoquinolinonyl, hydroisoquinolinonyl, isoquinolinyl, dihydroquinazolinonyl, hydroquinazolinonyl, quinazolinyl, dihydroquinoxalinonyl, hydroquinoxalinonyl, quinoxalinyl, benzimidazolyl, indazolyl, dihydrobenzimidazolonyl, hydrobenzimidazolonyl, benzimidazolinyl, dihydro-benzthiazolonyl, hydrobenzthiazolonyl, benzthiazolyl, dihydrobenzoxazolyl, benzotriazolyl, dihydrobenzothiophenonyl, hydrobenzothiophenonyl, benzothienyl, dihydrobenzofuranonyl, hydrobenzofuranonyl, benzofuranyl, benzdioxolanyl, dihydroindolonyl, hydroindolonyl, indolyl, indolizinyl, isoindolyl, indolinyl, indazolyl, pyrazolyl, pyrazolinyl, pyrazolidinyl, furanyl, thienyl, pyrrolyl, pyrrolinyl, pyrrolidinyl, imidazolyl, imidazolinyl, imidazolidinyl, pyridyl, purinyl, carbazolyl, pyrimidinyl, piperidinyl, triazolopyrimidinyl, tetrahydropyrazolopyridinyl, piperazinyl or morpholino; optionally substituted as provided in the first embodiment of the first aspect.

According to another embodiment of the first aspect of the present invention are provided compounds according to the first embodiment of the first aspect of the present invention wherein R³ is $R^{3a}$ and $R^{3a}$ is phenyl, napthyl, indazolyl, benzimidazolinyl, dihydrobenzoxazolyl, benzotriazolyl, benzothienyl, benzdioxolanyl, dihydroindolonyl, indolyl, furanyl, thienyl, pyridyl, purinyl, carbazolyl, piperidinyl, triazolopyrimidinyl, tetrahydropyrazolopyridinyl; optionally substituted as provided in the first embodiment of the first aspect.

According to another embodiment of the first aspect of the present invention are provided compounds according to the first embodiment of the first aspect of the present invention wherein $R^3$ is $R^{3a}$ and $R^{3a}$ is dihydro-benzthiazolonyl, hydrobenzthiazolonyl, benzthiazolyl, dihydrobenzothiophenonyl, hydrobenzothiophenonyl, benzothienyl, dihydrobenzofuranonyl, hydrobenzofuranonyl, benzofuranyl, dihydroindolonyl, hydroindolonyl, indolyl, indolizinyl, isoindolyl, indolinyl or indazolyl; optionally substituted as provided in the first embodiment of the first aspect.

According to another embodiment of the first aspect of the present invention are provided compounds according to the first embodiment of the first aspect of the present invention wherein $R^3$ is $R^{3a}$ and $R^{3a}$ is dihydrobenzoxazolyl, benzotriazolyl, indolyl, halonitrophenyl, halopyrimidine, halopurinyl, $C_{1-3}$alkyl-nitroaminopyrimidine, triazolopyrimidinyl, pyridyl, indazolyl, phenyl or benzdioxolanyl; optionally substituted as provided in the first embodiment of the first aspect.

According to another embodiment of the first aspect of the present invention are provided compounds according to the first embodiment of the first aspect of the present invention wherein $R^3$ is $R^{3a}$ and $R^{3a}$ is naphthyl, phenyl-O-phenyl, or thienyl; optionally substituted as provided in the first embodiment of the first aspect.

According to another embodiment of the first aspect of the present invention are provided compounds according to the first embodiment of the first aspect of the present invention wherein $R^3$ is $R^{3b}$.

According to another embodiment of the first aspect of the present invention are provided compounds according to the first embodiment of the first aspect of the present invention wherein $R^3$ is $R^{3b}$ and $R^{3b}$ is

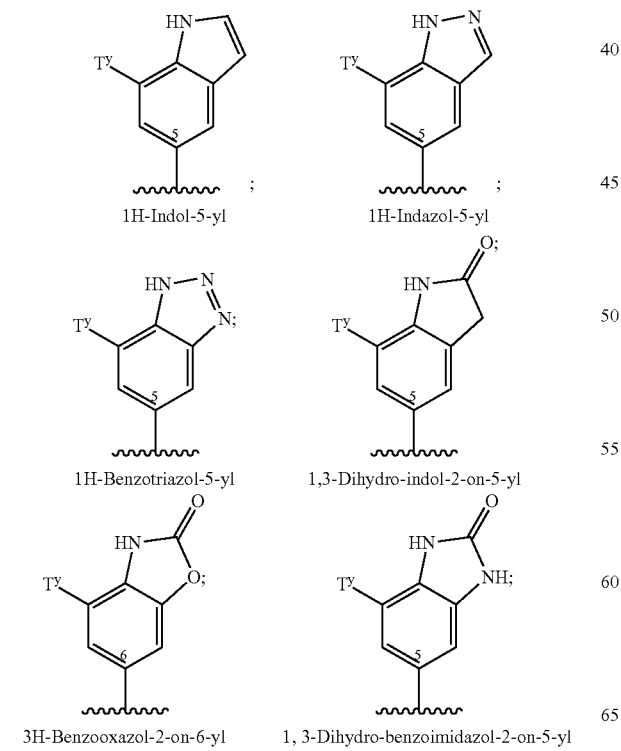

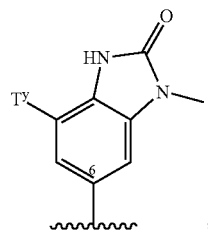

1-Methyl-1, 3-dihydro-benzoimidazol-2-on-6-yl

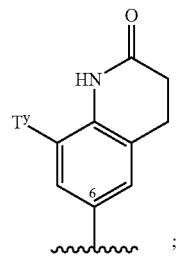

3, 4-Dihydro-1H-quinolin-2-on-6-yl

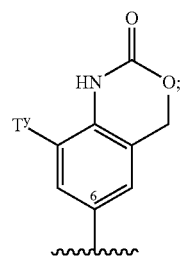

1, 4-Dihydro-benzo[d][1, 3]oxazin-2-on-6-yl

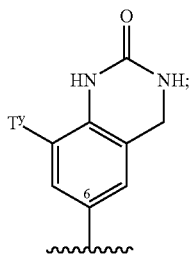

3, 4-Dihydro-1H-quinazolin-2-on-6-yl

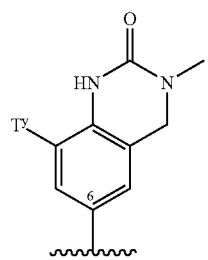

; or

3-Methyl-3, 4-dihydro-1H-quinazolin-2-on-6-yl

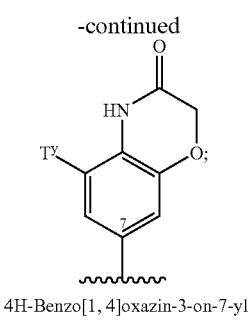

4H-Benzo[1,4]oxazin-3-on-7-yl wherein $T^y$ is H, $C_{1-4}$alkyl, F, Cl, Br or nitrile.

According to another embodiment of the first aspect of the present invention are provided compounds according to the first embodiment of the first aspect of the present invention wherein $R^3$ is $R^{3b}$ and $R^{3b}$ is azetidinyl, $C_{1-6}$alkyl, $C_{2-6}$alkenyl, $C_{2-6}$alkynl, dihydroquinolinonyl, hydroquinolinonyl, dihydroisoquinolinonyl, hydroisoquinolinonyl, dihydroquinazolinonyl, hydroquinazolinonyl, quinazolinyl, dihydroquinoxalinonyl, hydroquinoxalinonyl, quinoxalinyl, benzimidazolyl, 1H-indazol-5-yl, dihydrobenzimidazolonyl, hydrobenzimidazolonyl, benzimidazolinyl, dihydro-benzthiazolonyl, hydrobenzthiazolonyl, benzthiazolyl, dihydrobenzothiophenonyl, hydrobenzothiophenonyl, dihydrobenzofuranonyl, hydrobenzofuranonyl, benzdioxolanyl, dihydrobenzoxazolyl, benzotriazolyl, dihydroindolonyl, hydroindolonyl, indolizinyl, isoindolyl, indolinyl, pyrazolyl, pyrazolinyl, pyrazolidinyl, furanyl, pyrrolyl, pyrrolinyl, pyrrolidinyl, imidazolinyl, imidazolidinyl, purinyl, carbazolyl, pyrimidinyl, piperidinyl, piperazinyl or morpholino; optionally substituted as provided in the first embodiment of the first aspect.

According to another embodiment of the first aspect of the present invention are provided compounds according to the first embodiment of the first aspect of the present invention wherein $R^3$ is $R^{3b}$ and $R^{3b}$ is dihydrobenzimidazolonyl, hydrobenzimidazolonyl, benzimidazolinyl, dihydro-benzthiazolonyl, hydrobenzthiazolonyl, benzthiazolyl, dihydrobenzothiophenonyl, hydrobenzothiophenonyl, dihydrobenzofuranonyl, hydrobenzofuranonyl, 1H-indazol-5-yl, benzdioxolanyl, dihydrobenzoxazolyl, benzotriazolyl, dihydroindolonyl, hydroindolonyl, indolizinyl, isoindolyl, indolinyl, pyrazolyl, pyrazolinyl, pyrazolidinyl, furanyl, pyrrolyl, pyrrolinyl, pyrrolidinyl, imidazolinyl, imidazolidinyl, purinyl, carbazolyl, pyrimidinyl, piperidinyl, piperazinyl or morpholino; optionally substituted as provided in the first embodiment of the first aspect.

According to another embodiment of the first aspect of the present invention are provided compounds according to the first embodiment of the first aspect of the present invention wherein $R^3$ is $R^{3b}$ and $R^{3b}$ is azetidinyl, $C_{1-6}$alkyl, $C_{2-6}$alkenyl, $C_{2-6}$alkynl, dihydroquinolinonyl, hydroquinolinonyl, dihydroisoquinolinonyl, hydroisoquinolinonyl, dihydroquinazolinonyl, hydroquinazolinonyl, quinazolinyl, dihydroquinoxalinonyl, hydroquinoxalinonyl, quinoxalinyl, benzimidazolyl, 1H-indazol-5-yl, dihydrobenzimidazolonyl, hydrobenzimidazolonyl, benzimidazolinyl, dihydro-benzthiazolonyl, hydrobenzthiazolonyl, benzthiazolyl, dihydrobenzothiophenonyl, hydrobenzothiophenonyl, dihydrobenzofuranonyl, hydrobenzofuranonyl, benzdioxolanyl, dihydrobenzoxazolyl, benzotriazolyl, purinyl, carbazolyl, pyrimidinyl, piperidinyl, piperazinyl or morpholino; optionally substituted as provided in the first embodiment of the first aspect.

According to another embodiment of the first aspect of the present invention are provided compounds according to the first embodiment of the first aspect of the present invention wherein $R^3$ is $R^{3b}$ and $R^{3b}$ is azetidinyl, $C_{1-6}$alkyl, $C_{2-6}$alkenyl, $C_{2-6}$alkynl, dihydroquinolinonyl, hydroquinolinonyl, dihydroisoquinolinonyl, hydroisoquinolinonyl, dihydroquinazolinonyl, hydroquinazolinonyl, quinazolinyl, dihydroquinoxalinonyl, hydroquinoxalinonyl, quinoxalinyl, benzimidazolyl, benzdioxolanyl, dihydrobenzoxazolyl, benzotriazolyl, dihydroindolonyl, hydroindolonyl, 1H-indazol-5-yl, indolizinyl, isoindolyl, indolinyl, pyrazolyl, pyrazolinyl, pyrazolidinyl, furanyl, pyrrolyl, pyrrolinyl, pyrrolidinyl, imidazolinyl, imidazolidinyl, purinyl, carbazolyl, pyrimidinyl, piperidinyl, piperazinyl or morpholino; optionally substituted as provided in the first embodiment of the first aspect.

According to another embodiment of the first aspect of the present invention are provided compounds according to the first embodiment of the first aspect of the present invention wherein $R^3$ is $R^{3b}$ and $R^{3b}$ is benzdioxolanyl, dihydrobenzoxazolyl, benzotriazolyl, purinyl, carbazolyl; optionally substituted as provided in the first embodiment of the first aspect.

According to another embodiment of the first aspect of the present invention are provided compounds according to the first embodiment of the first aspect of the present invention wherein $R^3$ is $R^{3b}$ and $R^{3b}$ is dihydrobenzoxazolyl, benzotriazolyl, indolyl, halonitrophenyl, halopyrimidinyl, halopurinyl, $C_{1-3}$alkylnitroaminopyrimidinyl, triazolopyrimidinyl, pyridyl, 1H-indazol-5-yl, phenyl or benzdioxolanyl.

According to another embodiment of the first aspect of the present invention are provided compounds according to the first embodiment of the first aspect of the present invention wherein Q is Q' and wherein said compounds have an absolute configuration of R.

According to another embodiment of the first aspect of the present invention are provided compounds according to the first embodiment of the first aspect of the present invention wherein Q is Q' and wherein said compounds have an absolute configuration of S.

According to another embodiment of the first aspect of the present invention are provided compounds according to the first embodiment of the first aspect of the present invention wherein Q is Q" and wherein said compounds have an absolute configuration of R.

According to another embodiment of the first aspect of the present invention are provided compounds according to the first embodiment of the first aspect of the present invention wherein Q is Q" and wherein said compounds have an absolute configuration of S.

According to another embodiment of the first aspect of the present invention are provided compounds according to the first embodiment of the first aspect of the present invention wherein m and n are each 1.

According to another embodiment of the first aspect of the present invention are provided compounds according to the first embodiment of the first aspect of the present invention wherein D is 0.

According to another embodiment of the first aspect of the present invention are provided compounds according to the first embodiment of the first aspect of the present invention wherein A is C.

According to another embodiment of the first aspect of the present invention are provided compounds according to the first embodiment of the first aspect of the present invention wherein A is CH.

According to another embodiment of the first aspect of the present invention are provided compounds according to the first embodiment of the first aspect of the present invention wherein A is N.

According to another embodiment of the first aspect of the present invention are provided compounds according to the first embodiment of the first aspect of the present invention wherein E is N.

According to another embodiment of the first aspect of the present invention are provided compounds according to the first embodiment of the first aspect of the present invention wherein E is CH.

According to another embodiment of the first aspect of the present invention are provided compounds according to the first embodiment of the first aspect of the present invention wherein E is C.

According to another embodiment of the first aspect of the present invention are provided compounds according to the first embodiment of the first aspect of the present invention wherein said compounds exhibit as described herein a CGRP Binding $IC_{50}$ of less than 10 nM.

According to another embodiment of the first aspect of the present invention are provided compounds according to the first embodiment of the first aspect of the present invention wherein said compounds exhibit as described herein a CGRP Binding $IC_{50}$ of less than 100 nM.

According to another embodiment of the first aspect of the present invention are provided compounds according to the first embodiment of the first aspect of the present invention wherein said compounds exhibit as described herein a CGRP Binding $IC_{50}$ of less than 1000 nM.

According to another embodiment of the first aspect of the present invention are provided compounds according to the first embodiment of the first aspect of the present invention wherein p is 1; and G, J and E together form $A^x$ or $A^y$.

According to another embodiment of the first aspect of the present invention are provided compounds according to the first embodiment of the first aspect of the present invention wherein p is 1; and G, J and E together form $A^x$.

According to another embodiment of the first aspect of the present invention are provided compounds according to the first embodiment of the first aspect of the present invention wherein p is 1; and G, J and E together form $A^y$.

According to another embodiment of the first aspect of the present invention are provided compounds according to the first embodiment of the first aspect of the present invention wherein $A^x$ is a fused heterocycle having two fused rings with 5 to 7 members in each of said rings, said heterocycle containing one to four of the same or different heteroatoms selected from the group consisting of O, N and S; and optionally containing 1 or 2 carbonyls wherein the carbon atom of said carbonyl is a member of said fused heterocycle.

According to another embodiment of the first aspect of the present invention are provided compounds according to the first embodiment of the first aspect of the present invention wherein $A^x$ is a fused heterocycle having two fused rings with 5 to 7 members in each of said rings, said heterocycle containing one to four of the same or different heteroatoms selected from the group consisting of O, N and S.

According to another embodiment of the first aspect of the present invention are provided compounds according to the first embodiment of the first aspect of the present invention wherein $A^x$ is a fused heterocycle having two fused rings with 5 to 7 members in each of said rings, said heterocycle containing one to four of the same or different heteroatoms selected from the group consisting of O, N and S and wherein $A^x$ is substituted with phenyl.

According to another embodiment of the first aspect of the present invention are provided compounds according to the first embodiment of the first aspect of the present invention wherein $A^x$ is a fused heterocycle described herein.

According to another embodiment of the first aspect of the present invention are provided compounds according to the first embodiment of the first aspect of the present invention wherein $A^y$ is a 4 to 6 membered heterocycle containing one to three heteroatoms selected from the group consisting of O, N and S; and optionally containing 1 to 2 carbonyls, wherein the carbon atom of said carbonyl is a member of said 4 to 6 membered heterocycle.

According to another embodiment of the first aspect of the present invention are provided compounds according to the first embodiment of the first aspect of the present invention wherein $A^y$ is a 4 to 6 membered heterocycle containing one to three heteroatoms selected from the group consisting of O, N and S.

According to another embodiment of the first aspect of the present invention are provided compounds according to the first embodiment of the first aspect of the present invention wherein $A^y$ is a 4 to 6 membered heterocycle containing one to three heteroatoms selected from the group consisting of O, N and S; and optionally containing 1 to 2 carbonyls, wherein the carbon atom of said carbonyl is a member of said 4 to 6 membered heterocycle; and wherein $A^y$ is substituted with phenyl.

According to another embodiment of the first aspect of the present invention are provided compounds according to the first embodiment of the first aspect of the present invention wherein $A^y$ is a 4 to 6 membered heterocycle described herein.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are GJA' or GJA".

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are GJA'.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are GJA".

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are GJA' and GJA' is $A^x$.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are GJA' and GJA' is $A^y$.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are GJA" and GJA" is $A^x$.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are GJA" and GJA" is $A^y$.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are form a heterocycle selected from the group consisting of imidazolinonyl, imidazolidinonyl, dihydroquinolinonyl, dihydroisoquinolinonyl, dihydroquinazolinonyl, dihydroquinoxalinonyl, dihydrobenzoxazinyl, hydrobenzoxazinyl, dihydrobenzoxazinonyl, dihydrobenzimidazolonyl, dihydrobenzimidazolyl, dihydro-benzthiazolonyl, dihydrobenzthiazolyl, dihydrobenzothiophenonyl, dihydrobenzofuranonyl, dihydroindolonyl, indolinyl, pyrazolinyl, pyrazolidinyl, pyrrolinyl, pyrrolidinyl, imidazolinyl, imidazolidinyl, piperidinyl, piperazinyl and morpholino; wherein said heterocycle is optionally substituted with $C_{1-4}$alkyl, $C_{1-4}$alkoxy, $C_{1-4}$haloalkyl, cyano, $C_{3-7}$cycloalkyl, phenyl, halophenyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl or morpholino.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are form a heterocycle selected from the group consisting of imidazolinonyl, imidazolidinonyl, dihydroquinolinonyl, dihydroisoquinolinonyl, dihydroquinazolinonyl, dihydroquinoxalinonyl, dihydrobenzoxazinyl, hydrobenzoxazinyl, dihydrobenzoxazinonyl, dihydrobenzimidazolonyl, dihydrobenzimidazolyl, dihydro-benzthiazolonyl, dihydrobenzthiazolyl, dihydrobenzothiophenonyl, dihydrobenzofuranonyl, dihydroindolonyl, indolinyl, pyrazolinyl, pyrazolidinyl, pyrrolinyl, pyrrolidinyl, imidazolinyl, imidazolidinyl, piperidinyl, piperazinyl and morpholino; wherein said heterocycle is optionally substituted with $C_{1-4}$alkyl, $C_{1-4}$alkoxy, $C_{1-4}$haloalkyl, cyano, $C_{3-7}$cycloalkyl, phenyl, halophenyl, furanyl, pyrazolyl, pyrazolinyl, pyrazolidinyl, pyridyl, pyrimidinyl, piperidinyl, piperazinyl or morpholino.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are form a heterocycle selected from the group consisting of imidazolinonyl, imidazolidinonyl, dihydroquinolinonyl, dihydroisoquinolinonyl, dihydroquinazolinonyl, dihydrobenzofuranonyl, dihydroindolonyl, indolinyl, pyrazolinyl, pyrazolidinyl, pyrrolinyl, pyrrolidinyl, imidazolinyl, imidazolidinyl, piperidinyl, piperazinyl and morpholino; wherein said heterocycle is optionally substituted with $C_{1-4}$alkyl, $C_{1-4}$alkoxy, $C_{1-4}$haloalkyl, cyano, $C_{3-7}$cycloalkyl, phenyl, halophenyl, piperazinyl or morpholino.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are form a heterocycle selected from the group consisting of imidazolinonyl, imidazolidinonyl, dihydroquinolinonyl, dihydroisoquinolinonyl, dihydroquinazolinonyl, dihydroquinoxalinonyl, dihydrobenzoxazinyl, hydrobenzoxazinyl, dihydrobenzoxazinonyl, dihydrobenzimidazolonyl, dihydrobenzimidazolyl, dihydro-benzthiazolonyl, dihydrobenzthiazolyl, dihydrobenzothiophenonyl, dihydrobenzofuranonyl, dihydroindolonyl, indolinyl, pyrazolinyl, pyrazolidinyl, pyrrolinyl, pyrrolidinyl, imidazolinyl, imidazolidinyl, piperidinyl, piperazinyl and morpholino.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are form a heterocycle selected from the group consisting of imidazolinonyl, imidazolidinonyl, dihydroquinolinonyl, dihydroisoquinolinonyl, dihydroquinazolinonyl, dihydroquinoxalinonyl, dihydrobenzoxazinyl, hydrobenzoxazinyl and dihydrobenzoxazinonyl.

According to another embodiment of the first aspect of the present invention are provided compounds according to the first embodiment of the first aspect of the present invention wherein p is 0 such that G and J are each attached to A, then G, J and A together form a spirocyclic ring system with said rings of said system containing A and wherein G, J and A together are form a heterocycle selected from the group consisting of imidazolinonyl, imidazolidinonyl, dihydroquinolinonyl, dihydroisoquinolinonyl, dihydroquinazolinonyl, dihydroquinoxalinonyl and dihydrobenzoxazinyl.

According to various embodiments of a second aspect of the present invention are provided pharmaceutical compositions comprising compounds of Formula (I) as defined herein.

According to various embodiments of a third aspect of the present invention are provided methods of treating inflammation (particularly neurogenic inflammation), headache (particularly migraine), pain, thermal injury, circulatory shock, diabetes, Reynaud's syndrome, peripheral arterial insufficiency, subarachnoid/cranial hemorrhage, tumor growth, flushing associated with menopause and other conditions the treatment of which can be effected by the antagonism of the CGRP receptor by the administration of pharmaceutical compositions comprising compounds of Formula (I) as defined herein.

According to various embodiments of a fourth aspect of the present invention are uses of the compounds of the present invention selected from the group consisting of (a) immune regulation in gut mucosa (b) protective effect against cardiac anaphylactic injury (c) stimulating or preventing interleukin-1b(IL-1b)-stimulation of bone resorption (d) modulating expression of NK1 receptors in spinal neurons and (e) airway inflammatory diseases and chronic obstructive pulmonary disease including asthma. See (a) Calcitonin Receptor-Like Receptor Is Expressed on Gastrointestinal Immune Cells. Hagner, Stefanie; Knauer, Jens; Haberberger, Rainer; Goeke, Burkhard; Voigt, Karlheinz; McGregor, Gerard Patrick. Institute of Physiology, Philipps University, Marburg, Germany. Digestion (2002), 66(4), 197-203; (b) Protective effects of calcitonin gene-related peptide-mediated evodiamine on guinea-pig cardiac anaphylaxis. Rang, Wei-Qing; Du, Yan-Hua; Hu, Chang-Ping; Ye, Feng; Tan, Gui-Shan; Deng, Han-Wu; Li, Yuan-Jian. School of Pharmaceutical Sciences, Department of Pharmacology, Central South University, Xiang-Ya Road 88, Changsha, Hunan, Naunyn-Schmiedeberg's Archives of Pharmacology (2003), 367(3), 306-311; (c) The experimental study on the effect calcitonin gene-related peptide on bone resorption mediated by interleukin-1. Lian, Kai; Du, Jingyuan; Rao, Zhenyu; Luo, Huaican. Department of Orthopedics, Xiehe Hospital, Tongji Medical College, Huazhong University of Science and Technology, Wuhan, Peop. Rep. China. Journal of Tongji Medical University (2001), 21(4), 304-307, (d) Calcitonin gene-related Peptide regulates expression of neurokininl receptors by rat spinal neurons. Seybold V S, McCarson K E, Mermelstein P G, Groth R D, Abrahams L G. J. Neurosci. 2003 23 (5): 1816-1824. Department of Neuroscience, University of Minnesota, Minneapolis, Minn. 55455, and Department of Pharmacology, Toxicology, and Therapeutics, University of Kansas Medical Center, Kansas City, Kansas 66160 (e) Attenuation of antigen-induced airway hyperresponsiveness in CGRP-deficient mice. Aoki-Nagase, Tomoko; Nagase, Takahide; Oh-Hashi, Yoshio; Shindo, Takayuki; Kurihara, Yukiko; Yamaguchi, Yasuhiro; Yamamoto, Hiroshi; Tomita, Tetsuji; Ohga, Eijiro; Nagai, Ryozo; Kurihara, Hiroki; Ouchi, Yasuyoshi. Department of Geriatric Medicine, Graduate School of Medicine, University of Tokyo, Tokyo, Japan. American Journal of Physiology (2002), 283(5,Pt. 1), L963-L970; (f) Calcitonin gene-related peptide as inflammatory mediator. Springer, Jochen; Geppetti, Pierangelo; Fischer, Axel; Groneberg, David A. Charite Campus-Virchow, Department of Pediatric Pneumology and Immunology, Division of Allergy Research, Humboldt-University Berlin, Berlin, Germany. Pulmonary Pharmacology & Therapeutics (2003), 16(3), 121-130; and (g) Pharmacological targets for the inhibition of neurogenic inflammation. Helyes, Zsuzsanna; Pinter, Erika; Nemeth, Jozsef; Szolcsanyi, Janos. Department of Pharmacology and Pharmacotherapy, Faculty of Medicine, University of Pecs, Pecs, Hung. Current Medicinal Chemistry: Anti-Inflammatory & Anti-Allergy Agents (2003), 2(2), 191-218 all incorporated by reference herein.

According to various embodiments of a fifth aspect of the present invention are provided combinations of the compounds of the present invention with one or more agents selected from the group consisting of COX-2 inhibitors, NSAIDS, aspirin, acetaminophen, triptans, ergotamine and caffeine for the treatment of migraine.

Other embodiments of the present invention may comprise a suitable combination of two or more of the embodiments and/or aspects disclosed herein.

Yet other embodiments of the present invention may comprise a suitable subset of an embodiment and/or aspect disclosed herein or combinations thereof.

Still yet other embodiments and aspects of the invention will be apparent according to the description provided below.

DETAILED DESCRIPTION OF THE INVENTION

The description of the invention herein should be construed in congruity with the laws and principals of chemical bonding. For example, it may be necessary to remove a hydrogen atom in order accommodate a substituent at any given location.

As used herein, "heterocyclic" or "heterocycle" includes cyclic moieties containing one or more heteroatoms, (e.g., O, N or S) said heterocycles include those that are aromatic and those that are not, i.e., "alicyclic", unless otherwise specified.

As used herein, the term "fused bicyclic system" when describing for example a 5.6-fused bicyclic system containing 1 to 4 nitrogen atoms includes aromatic and alicyclic systems, e.g. indolizine, indole, isoindole, 3H-indole, indoline, indazole or benzimidazole.

If a substituent is named generically, then any and all species of that genus comprise that aspect of the invention. For example, a substituent generically named as "pyrrolonyl" (the radical of "pyrrolone", a pyrrole having a carbonyl) includes pyrrol-2-onyls wherein the carbonyl is adjacent to the nitrogen and pyrrol-3-onyls wherein the carbonyl and nitrogen have an intervening methylene.

Similarly, the present invention comprises that a substituent may be attached at any and all suitable points of attachment on said substituent unless otherwise specified.

However, it is also understood that the compounds encompassed by the present invention are those that are chemically stable, i.e., heteroalicyclic substituents of the present invention should not be attached in such a way that a heteroatom in said heteroalicyclic substituent is alpha to a point of attachment wherein said point of attachment is also a heteroatom.

An embodiment or aspect which depends from another embodiment or aspect, will describe only the variables having values or provisos that differ from the embodiment or aspect from which it depends. If for example a dependent embodiment only addresses $R^2$, then the variables and provisos not related to $R^2$ should reflect that of the embodiment from which it depends.

If a variable is quantified with a value of zero, then a bond attaching said variable should no longer be represented.

As used herein, "alkylene" means a divalent alkane, i.e., an alkane having two hydrogen atoms removed from said alkane (said hydrogen removed from two different carbon atoms when said alkane contains more than one carbon atom), e.g., —CH$_2$CH$_2$CH$_2$—.

As used herein, "alkylidene" means an alkane having two hydrogen atoms removed from one carbon atom in said alkane, e.g.,

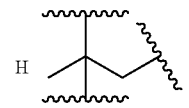

It should be understood that the alternating double bond designations in the six-membered ring of the 5,6-membered fused structure represented in Formula (I) are relative and represent the delocalized π orbital electrons of said ring.

As used herein, "aryl" or "ar-" includes phenyl or napthyl.

As used herein, "heterocyclic" or "heterocyclo" includes both heteroaryl and heteroalicyclic.

As used herein, "halo" or "halogen" includes fluoro, chloro, bromo and iodo and further means one or more of the same or different halogens may be substituted on a respective moiety.

Unless specified otherwise, acyclic hydrocarbons such as alkyl, alkoxy, alkenyl and alkynyl may be branched or straight chained.

It is to be understood that the present invention may include any and all possible stereoisomers, geometric isomers, diastereoisomers, enantiomers, anomers and optical isomers, unless a particular description specifies otherwise.

As used herein, "Trp74", means that the 74$^{th}$ residue in RAMP1 is tryptophan (Mallee et al. *J. Biol Chem* 2002, 277, 14294-8) incorporated by reference herein.

As used herein "anti-migraine compound" includes any compound, peptide or peptide fragment (modified or unmodified) capable of reversing or attenuating CGRP-receptor mediated vasodilation, (e.g., CGRP-receptor antagonists).

As used herein "test compound" includes any compound, peptide or peptide fragment (modified or unmodified) being tested to determine if it is capable of reversing or attenuating CGRP-receptor mediated vasodilation, (e.g., putative CGRP-receptor antagonists).

As used herein, "CGRP-receptor agonist" includes any compound, peptide or peptide fragment (modified or unmodified) capable of inducing CGRP-receptor mediated vasodilation particularly by example αCGRP or βCGRP; other members of the calcitonin family, e.g., adrenomedullin; N-terminal CGRP fragments, e.g., CGRP(1-12) CGRP(1-15) and CGRP(1-22); C-terminal amide (NH2) versions of CGRP e.g., CGRP(1-8+NH2), CGRP(1-13+NH2) or CGRP (1-14+NH2); and non-naturally occurring CGRP analogues e.g., [Ala$^1$ ψ(CH2NH)Cys$^2$]hCGRP which contains a pseudopeptide bond between Ala$^1$ and Cys$^2$. See Maggi C A, Rovero P, Giuliani S, Evangelista S, Regoli D, Meli A. Biological activity of N-terminal fragments of calcitonin gene-related peptide. Eur J. Pharmacol. 1990 Apr. 10; 179(1-2): 217-9; Qing X, Wimalawansa S J, Keith I M. Specific N-terminal CGRP fragments mitigate chronic hypoxic pulmonary hypertension in rats. Regul Pept. 2003 Jan. 31; 110 (2):93-9; and Dennis T, Fournier A, St Pierre S, Quirion R. Structure-activity profile of calcitonin gene-related peptide in peripheral and brain tissues. Evidence for receptor multiplicity. J Pharmacol Exp Ther. 1989 November; 251(2):718-25 incorporated by reference herein.

The compounds of this invention may exist in the form of pharmaceutically acceptable salts. Such salts may include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds of this invention contain an acidic group, the acidic group may exist in the form of alkali metal salts such as, for example, a potassium salt and a sodium salt; alkaline earth metal salts such as, for example, a magnesium salt and a calcium salt; and salts with organic bases such as a triethylammonium salt and an arginine salt. In the case of a sublingual formulation a saccharin salt or maleate salt may be of particular benefit. The compounds of the present invention may be hydrated or non-hydrated.

The compounds of this invention can be administered in such oral dosage forms as tablets, capsules (each of which includes sustained release or timed release formulations), pills, powders, granules, elixirs, tinctures, suspensions, syrups and emulsions. The compounds of this invention may also be administered intravenously, intraperitoneally, subcutaneously, or intramuscularly, all using dosage forms well known to those skilled in the pharmaceutical arts. The compounds can be administered alone, but generally will be administered with a pharmaceutical carrier selected upon the basis of the chosen route of administration and standard pharmaceutical practice. Compounds of this invention can also be administered in intranasal form by topical use of suitable intranasal vehicles, or by transdermal routes, using transdermal skin patches. When compounds of this invention are administered transdermally the dosage will be continuous throughout the dosage regimen.

While dosing from 0.01 mg/kg to 30 mg/kg is envisaged for compounds of the present invention, the dosage and dosage regimen and scheduling of a compounds of the present invention must in each case be carefully adjusted, utilizing sound professional judgment and considering the age, weight and condition of the recipient, the route of administration and the nature and extent of the disease condition. In accordance with good clinical practice, it is preferred to administer the instant compounds at a concentration level which will produce effective beneficial effects without causing any harmful or untoward side effects.

Synthesis

Compounds of the present invention may be synthesized according to the general schemas provided below. Variables provided in the schema below are defined in accordance with the description of compounds of the above Formula unless otherwise specified. The compounds of the present invention may be prepared according to Scheme 1 or Scheme 2. It may also be possible to use variations of said schemes to prepare the compounds of the present inventions, said variations known to those of ordinary skill in the art.

Scheme 1. Synthesis of Formula I Compounds

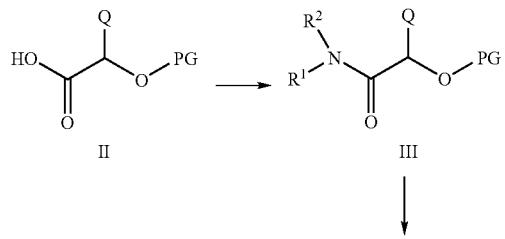

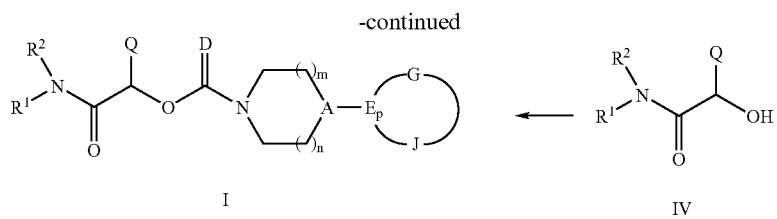

The synthesis described in Scheme 1 begins with a compound of Formula II, which is an α-hydroxycarboxylic acid with an appropriate hydroxyl protected terminus. Common hydroxy protecting groups (PG) include substituted benzyl group and trialkylsilyl group and their addition and removal are well known in the field. The carboxylic acid moiety of a Formula II compound is coupled with an amine of formula $HNR^1R^2$ using standard peptide coupling reagents to form an amide of Formula III. The hydroxy protecting group is removed resulting in a Formula IV compound. This compound is then coupled with an amine of Formula VIII (see below) in a carbamate forming reaction, generating a Formula I compound. Carbamate formation is conveniently carried using phosgene, disuccinimidyl carbonate, carbonyl diimidazole or other equivalents.

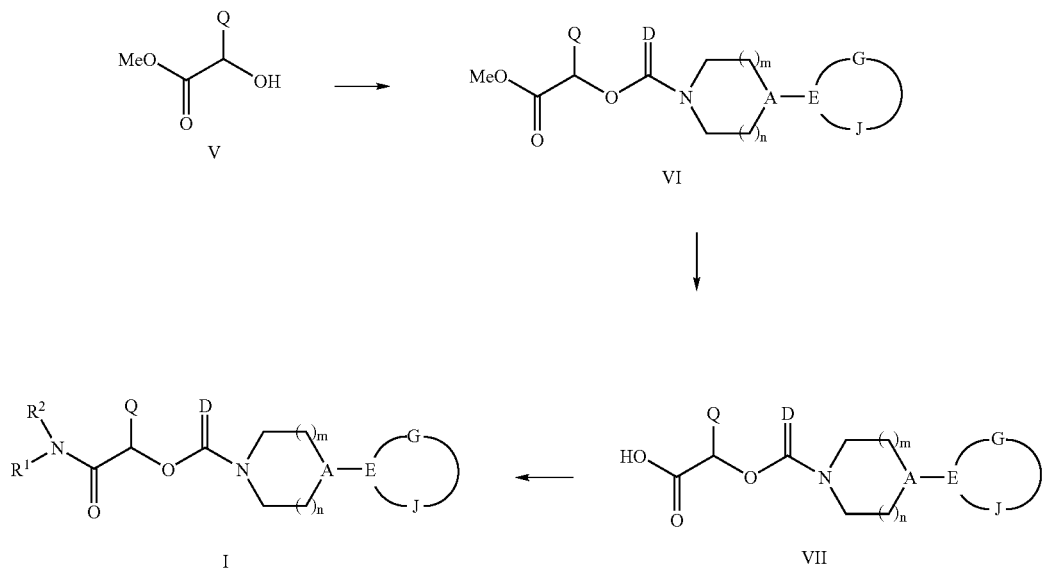

Scheme 2. Synthesis of Formula I Compounds

The synthesis described by Scheme 2 begins with a compound of Formula V, which is an α-hydroxycarboxylic acid with a protected carboxylate terminus. The protection is generally a methyl ester, but other protecting groups such as ethyl, t-butyl, and benzyl esters may also be used. The Formula V compound is coupled with an amine of Formula VIII (see below) in a carbamate forming reaction, as described above, to generate a Formula VI compound. The Formula VI compound is converted to a free acid compound of Formula VII which is then coupled with an amine of Formula $HNR^1R^2$ to generate a Formula I compound.

Scheme 3. Synthesis of Formula I Compounds

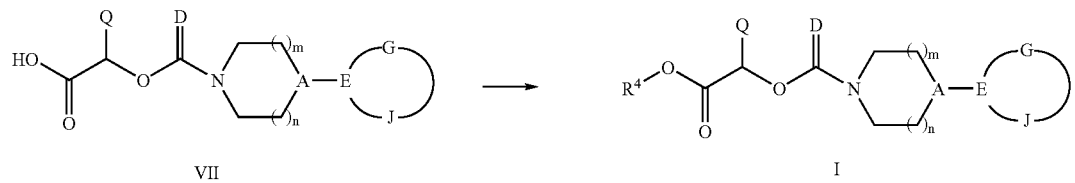

The synthesis described by Scheme 3 begins with a compound of Formula VII from Scheme 2. The Formula VII compound is coupled with an alcohol, $R^4$—OH. Such ester-forming reactions are well known in the art and can be carried out, for example, with carbodiimide coupling agents such as N,N-dicyclohexylcarbodiimide. In addition, it is often advantageous, especially for esters of secondary and tertiary alcohols, to include additives that accelerate acylations such as 4-dimethylaminopyridne.

Preparation of $HNR^1R^2$ and Formula VIII Amines

Formula VIII and $HNR^1R^2$ amines are commercially available, made by literature methods or described herein.

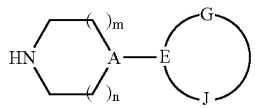
(VIII)

Preparation of Formula II and Formula V α-hydroxycarboxylic Acid (II)

(V)

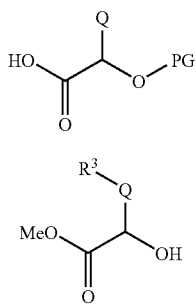

Formula II α-hydroxycarboxylic acid and Formula V α-hydroxycarboxylic acid ester may be made by methods known to one of ordinary skill in the art or made as described in Scheme 4.

Scheme 4. Synthesis of Formula II and Formula V Compounds

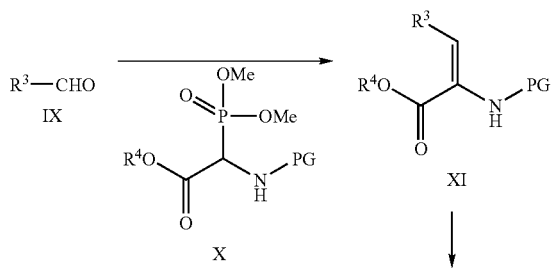

-continued

The synthesis of compounds of Formula II and Formula V are described in Scheme 4. A compound of Formula X is deprotonated with a base such as diazabicycloundecene or tetramethylguanidine or other organic or inorganic bases well known in the art. An aldehyde of Formula IX is reacted with a glycine phosphonate of Formula X in a Wadsworth-Emmons coupling reaction affording 10 an olefin of Formula XI. The compound of Formula XI is converted to a a-ketoester of Formula XII by removal of the amino protecting group (PG) followed by hydrolysis using water either by itself or in conjunction with an acid such as hydrochloric acid, trifluoroacetic acid, or other organic or inorganic acids. The a-ketoester of Formula XII can be reduced to give a compound of Formula V by an appropriate reducing agent such as sodium borohydride, sodium cyanoborohydride, hydrogen in the presence of an appropriate catalyst such as palladium on carbon, or other reducing agents well known in the art. The hydroxyl of a compound of Formula V can be protected to give an appropriate hydroxylprotected terminus of Formula XIII. Common hydroxylprotecting groups (PG) include methoxymethyl ether, benzyloxymethylether, substituted benzyl groups and trialkylsilyl group and their addition and removal are well known in the field. A compound of Formula XIII can be converted to a compound of formula II by treatment with lithium chloride, lithium hydroxide, sodium hydroxide, or other organic or inorganic bases using water or other suitable solvents using methodology well known in the art.

Compounds of Formula II and Formula V can also be prepared as described below in Scheme 5.

Scheme 5. Synthesis of Formula II and Formula V Compounds

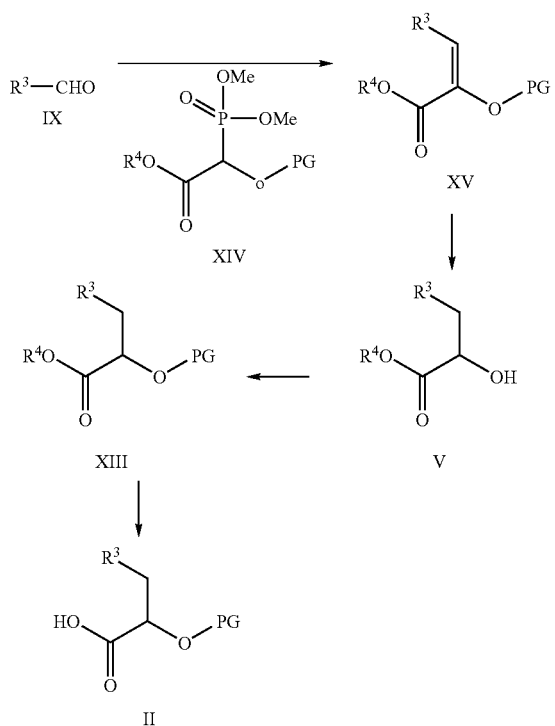

A compound of Formula XIV is deprotonated with a base such as diazabicycloundecene or tetramethylguanidine or other organic or inorganic bases well known in the art. An aldehyde of Formula IX is reacted with the lactate phosphonate of Formula X in a Wadsworth-Emmons coupling reaction affording an olefin of Formula XV. The compound of Formula XV is reduced to a lactate ester of Formula V by hydrogenation of the double bond. Reduction can either result in a racemic compound using, for example, hydrogenation over palladised charcoal, or a chiral compound using a chiral catalyst such as (−)-1,2-bis-((2R,5R)-2,5-diethylphospholano)benzene(cyclooctadiene)rhodium(I) tetrafluoroborate. The hydroxyl of a compound of Formula V can be protected to give an appropriate hydroxylprotected terminus of Formula XIII. Common hydroxylprotecting groups (PG) include methoxymethyl ether, benzyloxymethylether, substituted benzyl groups and trialkylsilyl group and their addition and removal are well known in the field. A compound of Formula XIII can be converted to a compound of formula II by treatment with lithium chloride, lithium hydroxide, sodium hydroxide, or other organic or inorganic bases using water or other suitable solvents using methodology well known in the art.

Compounds of Formula XI where R³ is an aromatic ring, can also be prepared as shown in Scheme 6.

Scheme 6. Synthesis of Formula XVII Compounds

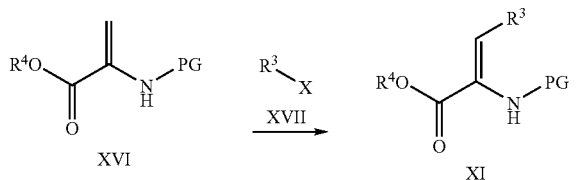

Scheme 6 starts with an N-protected aminoacrylate of Formula XVI that can be coupled to a compound of Formula XVII comprising an aromatic ring to which is attached a leaving group (X) such as iodine or bromine in the presence of a transition metal catalyst such as palladium (II) acetate in a non-reactive solvent with or without heating.

The syntheses of α-hyrdoxy carboxylic acids of Formula II and α-hyrdoxy carboxylic acid esters is well precedented in the literature and their syntheses should be known to anyone of ordinary skill in the art.

INTERMEDIATES AND EXAMPLES

General. $^1$H-NMR and $^{13}$C-NMR spectra were run on a Bruker 500 or 300 MHz instrument and chemical shifts were reported in ppm (δ) with reference to tetramethylsilane (δ=0.0). All evaporations were carried out under reduced pressure. Unless otherwise stated, LC/MS analyses were carried out on a Shimadzu instrument using a YMC C 18 column (3×50 mm) employing a 2 min linear gradient of 0% to 100% solvent B in A in a 3 min run. For LC/MS and for Shimadzu Preparative HPLC system, Solvent A-was: 10% methanol/90% water/0.1% trifluoroacetic acid, and solvent B was 90% methanol/10% water/0.1% trifluoroacetic acid with a UV detector set at 220 nm.

1-Benzyl-2',3'-dihydro-2'-oxospiro-[piperidine-4,4'(1'H)-quinazoline

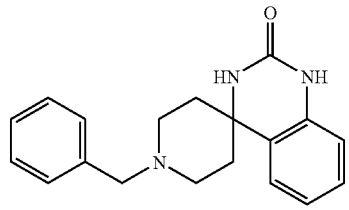

Polyphosphoric acid (113 g) was heated to 100-110° C. and stirred while 1-benzyl-piperidin-4-one (9.27 ml, 50 mmol) was added. Immediately afterwards, phenyl urea (9.55 g, 70. mmol) was added in portions small enough to avoid excessive foaming. The mixture was heated at 150-160° C. overnight. Water (200 mL) was then added slowly to the mixture which had been allowed to cool to 100-110° C. (at lower temperatures the mixture becomes too viscous to stir). The resulting solution was neutralized with ION NaOH to ca. pH 8, and then extracted wth chloroform. The organic phase was dried over magnesium sulfate and then concentrated to give the crude product which was purified by flash column chromatography on silica gel (6:4 ethyl acetate/hexanes) to give the desired product (9.0 g, 58%). Mass spec.: 308.25 (MH)⁺.

2',3'-dihydro-2'-oxospiro-[piperidine-4,4'(1'H)-quinazoline

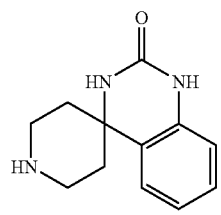

To a solution of 1-benzyl-2',3'-dihydro-2'-oxospiro-[piperidine-4,4'(1'H)-quinazoline (1.00 g) in degassed methanol (50 ml) and 6N hydrochloric acid (2.0 ml) was added 10% palladized charcoal (150 mg). The mixture was shaken on a Parr apparatus under an atmosphere of hydrogen at 60 psi overnight. LC/MS showed incomplete reaction. More 10% palladized charcoal (200 mg) was added, and the mixture was shaken for 2 more days. At that point, all starting material was consumed. The mixture was filtered and the filtrate concentrated to give 531 mg of the desired compound (64%). Mass spec.: 218.12 (MH)+.

4-Amino-4-cyano-piperidine-1-carboxylic acid tert-butyl ester

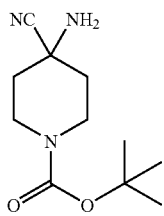

To a well stirred solution of 4-oxo-piperidine-1-carboxylic acid tert-butyl ester (9.0 g, 45.3 mmol) in methanol was added ammonium chloride (2.66 g, 49.8 mmol) at room temperature and stirred for 1 h. Sodium cyanide (2.44 g, 49.8 mmol) was added and stirring was continued for additional 16 h. The reaction mixture was quenched with 5% aqueous sodium hydrogencarbonate (50 mL), diluted with water, and the methanol removed by rotary evaporation. The cyanoamine was extracted with methylene chloride (3×100 mL), dried over sodium sulfate, and the solvents evaporated to give the desired compound as an oil in 91% yield. $^1$H-NMR (300 MHz, CDCl$_3$): δ 3.95-3.90 (m, 1H), 3.80-3.71 (m, 1H), 3.42-3.06 (m, 2H), 2.04-1.94 (m, 1H), 1.71-1.50 (m, 3H). Mass spec.: 226 (MH)+.

2-Phenyl-1,3,8-triaza-spiro[4.5]dec-1-en-4-one, hydrochloride

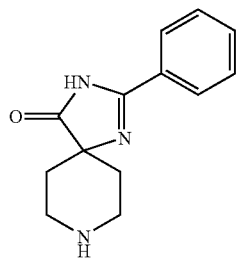

To a solution of 4-amino-4-cyano-piperidine-1-carboxylic acid tert-butyl ester (1.0 g, 4.44 mmol) in methylene chloride (30 mL) was added triethylamine (1.24 mL, 8.88 mol), followed by benzoyl chloride (936 mg, 6.66 mmol). After 30 min, 4-(dimethylamino)pyridine (40 mg, 0.33 mmol) was added and stirring continued for additional 12 h. The reaction mixture was then quenched with 1M sodium hydroxide (10 mL), diluted with ethyl acetate (100 mL), and separated. The organic layer was washed sequentially with 1M sodium hydroxide (40 mL), aqueous sodium hydrogencarbonate (50 mL), and brine (50 mL) then dried over sodium sulfate. The desired product, 4-benzoylamino-4-cyano-piperidine-1-carboxylic acid tert-butyl ester was obtained in 90% yield through crystallization using 30% ethyl acetate in hexane as a solvent.

To a solution of 4-benzoylamino-4-cyano-piperidine-1-carboxylic acid tert-butyl ester (1.3 g, 4 mmol) in ethanol (10 mL) was added 6M sodium hydroxide (1.5 mL) followed by 30% hydrogen peroxide. The reaction mixture was then refluxed for 3 h. The reaction mixture was then diluted with water (30 mL), and the ethanol removed. The residue was diluted with ethyl acetate (100 mL). The organic phase was washed with brine (30 mL) and dried over sodium sulfate. The desired product, 4-oxo-2-phenyl-1,3,8-triaza-spiro[4.5]dec-1-ene-8-carboxylic acid tert-butyl ester was obtained in 80% yield through crystallization from 30% ethyl acetate in hexane. The tert-butyl ester was then dissolved in methylene chloride (5 mL) and a saturated solution of hydrogen chloride in dioxane (25 mL) was added. After 2 h, the solvent was removed to give 2-phenyl-1,3,8-triaza-spiro[4.5]dec-1-en-4-one, hydrochloride as white powder in 95% yield. $^1$H-NMR (500 MHz, CD$_3$OD): δ 8.23-8.21 (m, 2H), 7.96-7.92 (m, 1H), 7.79-7.76 (m, 2H), 3.68-3.64 (m, 3H), 3.31-3.30 (m, 1H), 2.47-2.44 (m, 4H). Mass spec.: 230 (MH)+.

5-Formyl-indazole-1-carboxylic acid tert-butyl ester

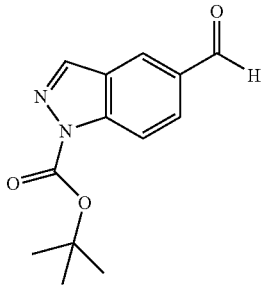

A methylene chloride (2 mL) solution of di-tert-butyldicarbonate (388 mg, 1.78 mmol) was added dropwise at room temperature to a solution of 1H-indazole-5-carbaldehyde (273 mg, 1.87 mmol), 4-dimethylaminopyridine (114 mg, 0.94 mmol), and triethylamine (0.26 mL, 1.87 mmol) in methylene chloride (10 mL). The resulting bright yellow solution was stirred at room temperature for 16 h. Solvents were removed in vacuo and the residue was subjected to flash chromatography with silica gel (25 g) and ethyl acetate/hexanes (1:1) containing 1% triethylamine as eluent to afford the title compound as a brownish yellow liquid (414 mg, 90%). $^1$H-NMR (CDCl$_3$, 500 MHz) δ 10.08 (s, 1H), 8.38 (s, 1H), 8.34 (s, 1H), 8.25 (d, J=8.5 Hz, 1H), 8.04 (d, J=8.8 Hz, 1H), 1.71 (s, 9H). $^{13}$CNMR (CDCl$_3$, 125 MHz) δ 191.8, 149.0, 142.5, 140.6, 133.0, 128.3, 126.4, 125.8, 115.3, 85.7, 27.8.

5-(2-Benzyloxycarbonylamino-2-methoxycarbonyl-vinyl)-indazole-1-carboxylic acid tert-butyl ester

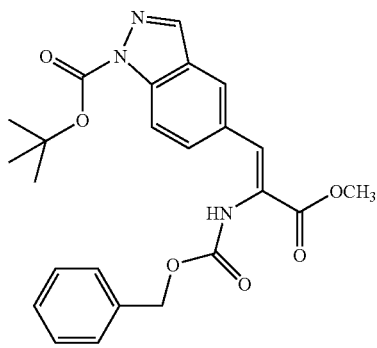

A solution of N-(benzyloxycarbonyl)-α-phosphonoglycine trimethyl ester (5.50 g, 16.6 mmol) and tetramethylguanidine (1.99 mL, 15.9 mmol) in anhydrous tetrahydrofuran (50 mL) was stirred at −78° C. for 20 min. To this was added a solution of 5-formyl-indazole-1-carboxylic acid tert-butyl ester (3.72 g, 15.1 mmol) in tetrahydrofuran (25 mL) slowly via syringe over 10 min. The reaction mixture was stirred at −78° C. for 4 h and then allowed to warm to room temperature overnight. The solvent was evaporated and the resulting residue subjected to flash column chromatography on silica gel (1:2 ethyl acetate/hexane) giving the title compound as a white foam (5.77 g, 85%). $^1$H-NMR (CDCl$_3$, 500 MHz) δ 8.09 (d, J=9.0 Hz, 1H), 8.08 (s, 1H), 7.84 (s, 1H), 7.67 (d, J=9.0 Hz, 1H), 7.47 (s, 1H), 7.30 (br s, 5H), 6.43 (br s, 1H), 5.09 (s, 2H), 3.84 (s, 3H), 1.72 (s, 9H). Mass spec.: 452 (MH)$^+$.

2-Trimethylsilanyl-ethanesulfonyl chloride

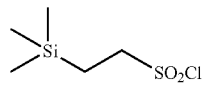

Sulfuryl chloride (43 ml, 539 mmol) was added in 3 min to a clear solution of triphenylphosphine (129 g, 490 mmol) in methylene chloride (200 mL) at 0° C. in a flame-dried three-neck round bottom flask. After stirring at 0° C. for 5 min, the ice-water bath was removed and sodium 2-trimethylsilylethanesulfonate (50 g, 245 mmol) was added in portions over 10 min. The resulting white suspension was stirred at room temperature for 16 h, then it was filtered through a pad of celite. The filtrate was concentrated to ca 50 mL, ethyl acetate/hexanes (1:3, 1000 mL) and celite (40 g) were added. The mixture was stirred at room temperature for 15 min and filtered through a pad of celite. Solvents were removed in vacuo and the residue was loaded onto a pre-wetted column with silica gel (300 mL) using 1:3 ethyl acetate/hexanes as the eluent. Solvents were removed and the title compound was obtained as a light tan liquid (41.9 g, 85%). If not used immediately, the final product should be stored under nitrogen in the freezer or refrigerator to minimize decomposition. $^1$H-NMR (CDCl$_3$, 500 MHz) δ 3.61-3.57 (m, 2H), 1.32-1.27 (m, 2H), 0.10 (s, 9H).

1-(2-Trimethylsilanyl-ethanesulfonyl)-1H-indole-5-carboxylic acid ethyl ester

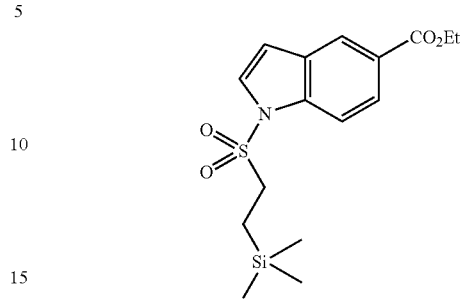

A solution of 1H-indole-5-carboxylic acid ethyl ester (10.31 g, 58.8 mmol) in dimethylformamide (50 mL) was added dropwise at 0° C. to a mixture of sodium hydride (1.83 g, 76.4 mmol) in dimethylformamide (150 mL). The resulting mixture was stirred at 0° C. for 30 min, then a solution of 2-trimethylsilanyl-ethanesulfonyl chloride (17.7 g, 88.2 mmol) in dimethylformamide (100 mL) was added slowly at 0° C. to the above mixture. After 2 h, sat. aqueous ammonium chloride (200 mL) was added, and the mixture was extracted with ethyl acetate (300 mL). After separation, the aqueous layer was extracted with ethyl acetate (2×150 mL). The combined organic layers were washed with brine (3×150 mL), and dried over anhydrous sodium sulfate. Solvents were removed in vacuo and the residue was subjected to flash chromatography on silica gel using 1:1.5 methylene chloride/hexanes as eluent to afford the title compound as a white solid (15.8 g, 79%). $^1$H-NMR (CDCl$_3$, 500 MHz) δ 8.36 (d, J=1.5 Hz, 1H), 8.03 (dd, J 9.0, 2.0 Hz, 1H), 7.92 (d, J=8.5 Hz, 1H), 7.50 (d, J=3.5 Hz, 1H), 6.75 (d, J=3.5 Hz, 1H), 3.94 (s, 3H), 3.21-3.18 (m, 2H), 0.84-0.80 (m, 2H), −0.06 (s, 9H). $^{13}$C-NMR (CDCl$_3$, 125 MHz) δ 167.3, 137.7, 130.3, 128.3, 125.9, 125.5, 124.0, 112.8, 108.3, 52.2, 51.2, 10.1, −2.1. Mass spec. 354.12 (MH)$^+$.

Similarly prepared:

1-(2-Trimethylsilanyl-ethanesulfonyl)-1H-indazole-5-carboxylic acid ethyl ester

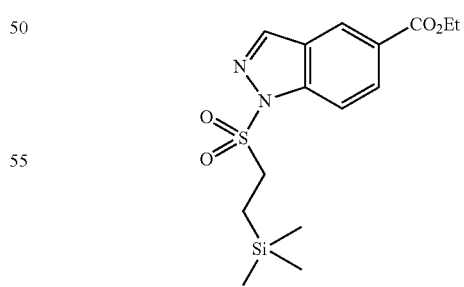

$^1$H-NMR (CDCl$_3$, 500 MHz) δ 8.51 (s, 1H), 8.34 (s, 1H), 8.21 (dd, J=8.9, 1.5 Hz, 1H), 8.12 (d, J=9.2 Hz, 1H), 3.96 (s, 3H), 3.42-3.39 (m, 2H), 0.86-0.82 (m, 2H), −0.02 (s, 9H). $^{13}$C-NMR (CDCl$_3$, 125 MHz) δ 166.4, 143.1, 141.2, 130.1, 126.5, 125.0, 124.2, 112.9, 52.5, 51.3, 9.8, −2.1. Mass spec. 355.13 (MH)$^+$.

[1-(2-Trimethylsilanyl-ethanesulfonyl)-1H-indol-5-yl]-methanol

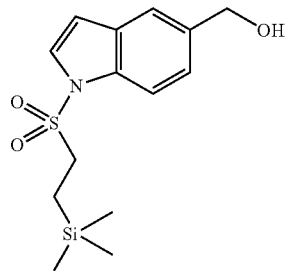

A solution of diisobutylaluminum hydride (82.9 mL, 1M in toluene, 82.9 mmol) was added slowly at 0° C. to the solution of 1-(2-trimethylsilanylethanesulfonyl)-1H-indole-5-carboxylic acid ethyl ester (8.81 g, 25.9 mmol) in toluene (200 mL). After it was stirred at 0° C. for 45 min, the reaction was quenched by the addition of methanol (26 mL), pulverized sodium sulfate decahydrate (194 g) and celite (26 mL). The mixture was warmed up to room temperature in 1 h and filtered through a pad of celite. Solvents were removed in vacuo to afford the title compound as a very viscous liquid, which solidified upon cooling. A white solid (8.08 g, 100% yield). $^1$H-NMR (CDCl$_3$, 500 MHz) δ 7.87 (d, J=8.5 Hz, 1H), 7.62 (s, 1H), 7.44 (d, J=3.7 Hz, 1H), 7.35 (dd, J=8.6, 1.5 Hz, 1H), 6.66 (d, J=3.7 Hz, 1H), 4.79 (s, 2H), 3.18-3.14 (m, 2H), 1.73 (s, 1H), 0.85-0.82 (m, 2H), −0.06 (s, 9H). Mass spec. 312.14 (MH)$^+$.

[1-(2-Trimethylsilanyl-ethanesulfonyl)-1H-indazol-5-yl]-methanol

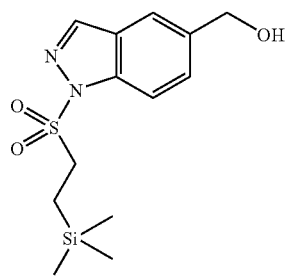

A solution of 1-(2-trimethylsilanyl-ethanesulfonyl)-1H-indazole-5-carboxylic acid ethyl ester (azeotropically dried with toluene (2×), 5.77 g, 16.9 mmol) in tetrahydrofuran (50 mL) was added at 0° C. to a mixture of lithium borohydride (3.68 g, 169 mmol) in tetrahydrofuran (100 mL). The mixture was warmed up to room temperature and stirred for 14 h. It was cooled to 0° C. and lithium borohydride (3.5 g) was added. The mixture was warmed up to room temperature and stirred for 14 h. It was re-cooled to 0° C. and sat. aqueous ammonium chloride (25 mL) was added slowly. The resulted white suspension was filtered through a pad of celite, solvents were removed and the residue was subjected to flash chromatography using ethyl acetate/hexanes (1:1.5) with 1% triethylamine to afford the title compound as a white solid (3.8 g, 72%). $^1$H-NMR (CD$_3$OD, 500 MHz) δ 8.41 (s, 1H), 8.04 (d, J=8.5 Hz, 1H), 7.85 (s, 1H), 7.61 (dd, J=8.5, 1.2 Hz, 1H), 4.76 (s, 2H), 3.49-3.46 (m, 2H), 0.76-0.72 (m, 2H), −0.03 (s, 9H); $^{13}$C-NMR (CD$_3$OD, 125 MHz) δ 141.2, 140.9, 138.3, 129.2, 125.8, 119.6, 112.7, 63.8, 50.8, 9.9, −3.2. Mass spec. 313.12 (MH)$^+$.

1-(2-Trimethylsilanyl-ethanesulfonyl)-1H-indole-5-carbaldehyde

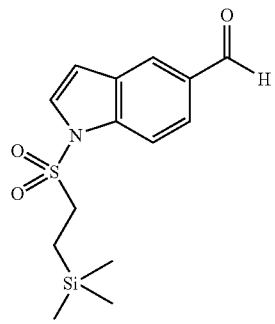

A solution of [1-(2-trimethylsilanyl-ethanesulfonyl)-1H-indol-5-yl]-methanol (2.1 g, 6.74 mmol) in methylene chloride (30 mL) was added at 0° C. to a mixture of activated manganese dioxide (22 g, azeotropically dried with toluene (2×)) and methylene chloride (70 mL) in a 500 mL round bottom flask. The reaction mixture was stirred at 0° C. for 30 min and filtered through a pad of celite. Solvents were removed in vacuo to afford the title compound as a white solid (1.8 g, 80%). $^1$H-NMR (CDCl$_3$, 500 MHz) δ 10.06 (s, 1H), 8.15 (s, 1H), 8.01 (d, J=8.6 Hz, 1H), 7.87 (dd, J=8.6, 1.5 Hz, 1H), 7.54 (d, J=3.4 Hz, 1H), 6.80 (d, J=3.6 Hz, 1H), 3.24-3.20 (m, 2H), 0.86-0.82 (m, 2H), −0.06 (s, 9H). $^{13}$C-NMR (CDCl$_3$, 125 MHz) δ 191.9, 138.5, 132.3, 130.7, 128.8, 125.3, 125.1, 1134.6, 108.4, 51.4, 10.2, −2.1. Mass spec. 310.12 (MH)$^+$.

Similarly prepared:

1-(2-Trimethylsilanyl-ethanesulfonyl)-1H-indazole-5-carbaldehyde

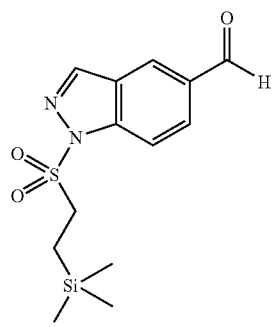

Mass spec. 311.10 (MH)$^+$.

2-Benzyloxycarbonylamino-3-[1-(2-trimethylsilanyl-ethanesulfonyl)-1H-indol-5-yl]-acrylic acid methyl ester

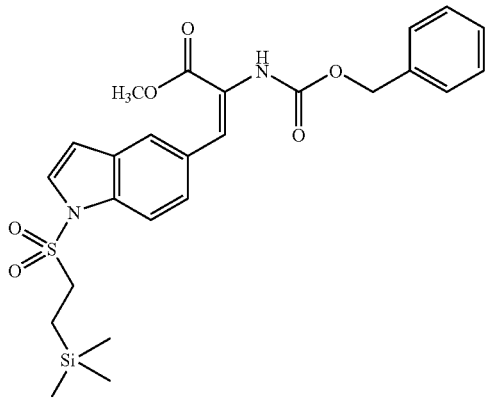

1,1,3,3-Tetramethylguanidine (0.68 mL, 5.43 mmol) was added at room temperature to a solution of N-(benzyloxycarbonyl)-α-phophonoglycine trimethyl ester (1.88 g, 5.69 mmol) in tetrahydrofuran (40 mL). The mixture was stirred at room temperature for 15 min and cooled to −78° C., and a solution of 1-(2-trimethylsilanyl-ethanesulfonyl)-1H-indole-5-carbaldehyde (1.6 g, 5.17 mmol) in tetrahydrofuran (15 mL) was added slowly. The resulting reaction mixture was stirred at −78° C. for 2 h and then warmed to room temperature in 3 h. Solvents were removed in vacuo and the residue was subjected to flash chromatography on silica gel using methylene chloride/hexanes (1:1.5) with 1% triethylamine as eluent to afford the title compound as a 92:8 Z/E mixture (determined by integration of $CO_2CH_3$, for Z isomer at 3.79 ppm, and E isomer at 3.65 ppm). For the Z isomer: $^1$H-NMR ($CD_3CN$, 500 MHz) δ 7.96 (s, 1H), 7.91 (d, J=8.5 Hz, 1H), 7.66 (d, J=8.5 Hz, 1H), 7.56 (d, J=3.7 Hz, 1H), 7.51 (s, 1H), 7.43-7.35 (m, 5H), 7.67 (d, J=3.7 Hz, 1H), 5.16 (s, 2H), 3.79 (s, 3H), 3.42-3.38 (m, 2H), 0.87-0.83 (m, 2H), −0.04 (s, 9H). Mass spec. 515.20 $(MH)^+$.

Similarly prepared:

2-Benzyloxycarbonylamino-3-[1-(2-trimethylsilanyl-ethanesulfonyl)-1H-indazol-5-yl]-acrylic acid methyl ester

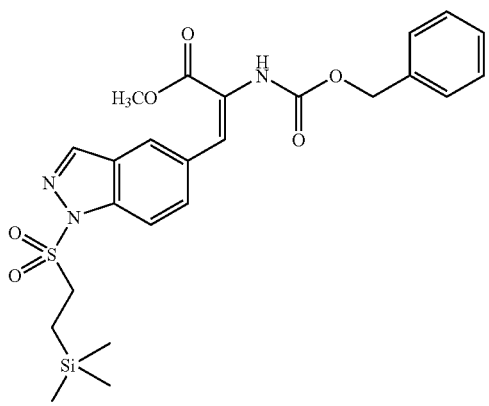

Flash chromatography on silica gel using methylene chloride containing 1% triethylamine as eluent afforded the title compound as a 95:5 Z/E mixture (determined by the integration of —CH=C($CO_2Me$)(NHCBz), 3.72 g, 92%). For the Z isomer: $^1$H-NMR ($CD_3CN$, 500 MHz) δ 8.39 (s, 1H), 8.12 (s, 1H), 8.03 (d, J=8.8 Hz, 1H), 7.84 (dd, J=8.8, 1.2 Hz, 1H), 7.51 (s, 1H), 7.43-7.35 (m, 5H), 5.14 (s, 2H), 3.81 (s, 3H), 3.51-3.47 (m, 2H), 0.83-0.79 (m, 2H), −0.02 (s, 9H). Mass spec. 516.18 $(MH)^+$.

7-Methyl-2-(2-trimethylsilanyl-ethanesulfonyl)-2H-indazole-5-carbaldehyde

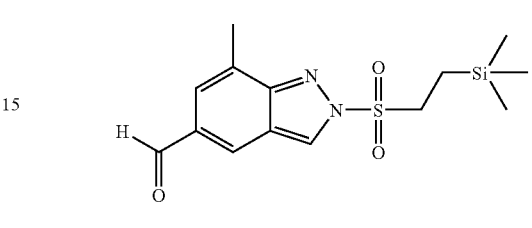

To a suspension of 7-methylindazole 5-aldehyde (3.0 g, 18.7 mmol) in methylene chloride (150 mL) was added triethylamine (7.83 mL, 56.2 mL, 3 equiv) followed by dropwise addition of neat 2-trimethylsilanyl-ethanesulfonyl chloride (5.60 g, 28.1 mmol, 1.5 equiv). The mixture gradually became homogeneous and was allowed to stir at room temperature for 16 h. The solution was concentrated to a minimum amount of methylene chloride and then subjected to flash column chromatography on silica gel (1:4 ethyl acetate/hexanes) to give 4.7 g (77%) of the product as a pale yellow solid. $^1$H-NMR ($CDCl_3$, 300 MHz) δ 9.98 (s, 1H), 8.77 (s, 1H), 8.09 (s, 1H), 7.64 (s, 1H), 3.64-3.58 (m, 2H), 2.65 (s, 3H), 0.88-0.82 (m, 2H), 0.01 (s, 9H).

2-Benzyloxycarbonylamino-3-[7-methyl-2-(2-trimethylsilanyl-ethanesulfonyl)-2H-indazol-5-yl]-acrylic acid methyl ester

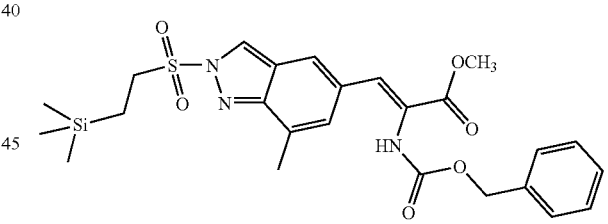

To a solution of N-(benzyloxycarbonyl)-α-phosphonoglycine trimethyl ester (4.93 g, 14.9 mmol, 1.1 equiv) in anhydrous tetrahydrofuran (75 mL) was added tetramethylguanidine (1.78 mL, 1.05 equiv). The mixture was stirred at room temperature under nitrogen for 5 min and was then cooled to −78° C. After stirring for 15 min at −78° C., a solution of 7-methyl-2-(2-trimethylsilanyl-ethanesulfonyl)-2H-indazole-5-carbaldehyde in tetrahydrofuran (25 mL) was added. The reaction mixture was allowed to slowly warm to room temperature overnight. Although the reaction was incomplete, the solvent was evaporated. The resulting residue was dissolved in ethyl acetate and washed with 1M sulfuric acid. The organic layer was separated, dried over magnesium sulfate, filtered and evaporated. Flash column chromatography (1:4 ethyl acetate/hexanes) gave 2.66 g (37%) of the product as white glass foam. $^1$H-NMR ($CDCl_3$, 300 MHz) δ 8.48 (s, 1H), 7.62 (s, 1H), 7.38-7.25 (m, 7H), 6.48 (bs, 1H), 5.10 (s, 2H), 3.83 (s, 3H), 3.58-3.52 (m, 2H), 2.51 (s, 3H), 0.89-0.83 (m, 2H), 0.02 (s, 9H). Mass spec.: 530 (MH)+.

4-Bromo-2,6-dimethylphenyldiazo-t-butyl sulfide

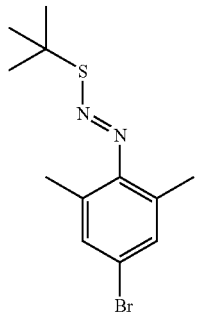

4-Bromo-2,6-dimethylaniline (20.00 g, 100 mmol) was ground to a powder with a mortar and pestle and then suspended in 24% hydrochloric acid (41 mL). The stirred mixture was cooled to −20° C. and treated with sodium nitrite (7.24 g, 1.05 equiv) in water (16 mL), dropwise over 40 min while the temperature was maintained below −5° C. After a further 30 min at −5° C. to −20° C., the mixture was buffered to ca. pH 5 with solid sodium acetate. This mixture (kept at ca. −10° C.) was added in portions to a stirred solution of t-butyl thiol (11.3 mL, 1 equiv) in ethanol (100 mL) at 0° C. over ca. 10 min. Following addition, the mixture was stirred at 0° C. for 30 min and then crushed ice (ca. 150 mL) was added. The mixture was stored in the refrigerator overnight. The resulting light-brown solid was collected by filtration, washed with water, and dried under high vacuum for several hours. (26.90 g, 89%). The compound appeared to be stable as a solid but underwent significant decomposition when recrystallization from ethanol was attempted. $^1$H-NMR (CDCl$_3$, 500 MHz) δ 1.58 (9H, s), 1.99 (6H, s), 7.21 (2H, s). Mass spec.: 303.05 (MH)+.

5-Bromo-7-methylindazole

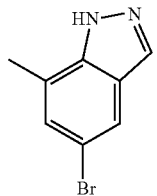

Into a flame-dried round bottom flask, 4-bromo-2,6-dimethylphenyldiazo-t-butyl sulfide (12.50 g, 41.5 mmol) and potassium t-butoxide (46.56 g, 10 equiv) were combined. A stir bar was added and the mixture placed under nitrogen. To this was added dry DMSO (120 mL). The mixture was stirred vigorously overnight at rt. The reaction mixture was then carefully poured into a mixture of crushed ice (400 mL) and 10% hydrochloric acid (200 mL). The resulting suspension was left to stand at 4° C. overnight and the solid was collected by filtration and washed with water. The crude solid was dissolved in 5:1 methylene chloride/methanol and the solution dried over magnesium sulfate and evaporated to give the product as an off-white solid (7.60 g, 87%). $^1$H-NMR (CDCl$_3$/CD$_3$OD, 500 MHz) δ 2.51 (3H, s), 7.22 (1H, s), 7.69 (1H, s), 7.94 (1H, s). Mass spec.: 211.03 (MH)+.

7-methylindazole-5-carboxaldehyde

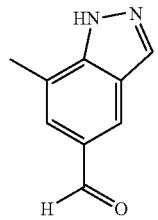

5-Bromo-7-methylindazole (6.10 g, 28.9 mmol) and sodium hydride (60% in mineral oil, 1.27 g, 1.1 equiv) were weighed into a flame-dried round-bottom flask containing a magnetic stir bar. Under a nitrogen atmosphere at room temperature, dry tetrahydrofuran (30 mL) was added. The mixture was stirred at room temperature for 15 min, during which time it became homogeneous. The stirred mixture was cooled to −70° C. and a solution of sec-butyllithium in cyclohexane (1.4M, 45 mL, 2.2 equiv) was added over several minutes. After 1 h at −70° C., dimethylformamide (10 mL) was added over several minutes. The mixture was allowed to warm to room temperature and was stirred overnight. It was then cooled to 0° C. and carefully treated with 1N hydrochloric acid (60 mL). After a few minutes, solid sodium bicarbonate was added to basify the mixture to pH 9-10. The layers were separated and the aqueous phase washed twice with ethyl acetate. The combined organic phases were extracted with 0.8M sodium hydrogen sulfate (3×125 mL). The combined aqueous phases were washed with ethyl acetate (100 mL) and then the pH was adjusted to ca. 10 with solid sodium hydroxide. The resulting suspension was extracted with ethyl acetate (3×150 mL). The combined organic phases were washed with brine, dried (magnesium sulfate) and evaporated to give the product as a light-tan solid (3.01 g, 65%). $^1$H-NMR (CDCl$_3$, 500 MHz) δ 2.63 (3H, s), 7.73 (1H, s), 8.12 (1H, s), 8.25 (1H, s), 10.03 (1H, s). Mass spec.: 161.06 (MH)+.

2-Benzyloxycarbonylamino-3-(7-methyl-1H-indazol-5-yl)-acrylic acid methyl ester

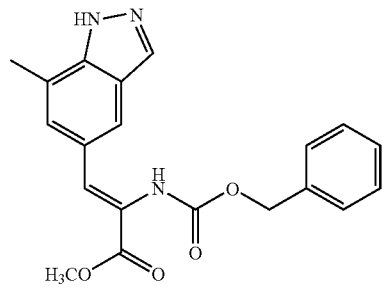

A stirred solution of N-benzyloxycarbonyl-α-phosphonoglycine trimethyl ester (5.51 g, 1.2 equiv.) in tetrahydrofuran (30 mL) at room temperature was treated with tetramethylguanidine (1.91 mL, 1.1 equiv). After 10 min, 7-methylindazole-5-carboxaldehyde (2.22 g, 13.86 mmol) in tetrahydrofuran (20 mL) was added. Disappearance of starting material was monitored by TLC and LC/MS. After 5 days at room temperature, the solvent was evaporated and the residue dissolved in ethyl acetate. The solution was washed with 2% phosphoric acid and brine, dried (magnesium sulfate) and evaporated. The residue was purified by flash chromatography on silica gel, eluting with 1) 1:1 and 2) 2:1 ethyl acetate/hexane, to give the product as a colorless foam (4.93 g, 97%). $^1$H-NMR (CDCl$_3$, 500 MHz) δ 2.43 (3H, s), 3.80 (3H, s), 5.12 (2H, s), 6.66 (1H, s), 7.28 (5H, brs), 7.33 (1H, s), 7.47 (1H, s), 7.74 (1H, s), 7.96 (1H, s). Mass spec.: 366.16 (MH)$^+$.

tert-Butyl(Z)-1-(methoxycarbonyl)-2-(2-((2-(trimethylsilyl)ethoxy)methyl)-7-methyl-2H-indazol-5-yl)vinylcarbamate

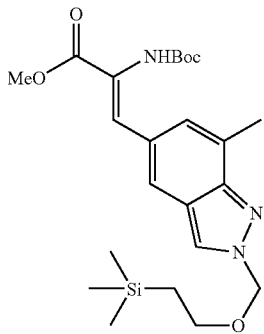

To a solution of 2-((2-(trimethylsilyl)ethoxy)methyl)-7-methyl-2H-indazole-5-carbaldehyde (4.46 g, 15.4 mmol) and N-(tert-butoxycarbonyl)-methyl-2-(dimethylphosphono)glycinate (4.80 g, 1.0 equiv) in tetrahydrofuran (40 mL) at room temperature was added N,N,N',N'-tetramethylguanidine (3.29 mL, 1.7 equiv). The reaction was allowed to stir at room temperature for 3 d. The reaction was diluted with ethyl acetate and water. Poured into diethyl ether, and washed with water (2×), then brine, dried over magnesium sulfate and concentrated. Column chromatography (30% ethyl acetate/hexanes->40% ethyl acetate/hexanes) gave 5.90 g (83%) as a foam. Mass spec.: 462.40 (MH)$^+$.

Methyl 3-(2-((2-(trimethylsilyl)ethoxy)methyl)-7-methyl-2H-indazol-5-yl)-2-hydroxypropanoate

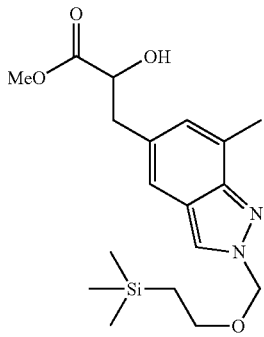

To a solution of tert-butyl(Z)-1-(methoxycarbonyl)-2-(2-((2-(trimethylsilyl)ethoxy)methyl)-7-methyl-2H-indazol-5-yl)vinylcarbamate (200 mg, 0.43 mmol) in dichloromethane (2 mL) at 0° C. was added trifluoroacetic acid (1 mL). The ice bath was removed. After 30 minutes, the reaction was poured into separatory funnel containing ethyl acetate and water, neutralized with solid sodium bicarbonate, and the layers separated. The organics were washed with saturated sodium bicarbonate, then brine, dried over magnesium sulfate, and concentrated. The yellow residue was treated with sodium cyanoborohydride (200 mg, 7.4 equiv) and tetrahydrofuran (2 mL). The reaction was stirred at room temperature overnight, diluted with ethyl acetate, washed with water (2×), then brine, dried over magnesium sulfate, and concentrated. Column chromatography (25% ethyl acetate/hexanes) gave 20.4 mg (13%) as a light yellow oil. Mass spec.: 365.40 (MH)$^+$.

1-(Methoxycarbonyl)-2-(2-((2-(trimethylsilyl)ethoxy)methyl)-7-methyl-2H-indazol-5-yl)ethyl 4-nitrophenyl carbonate

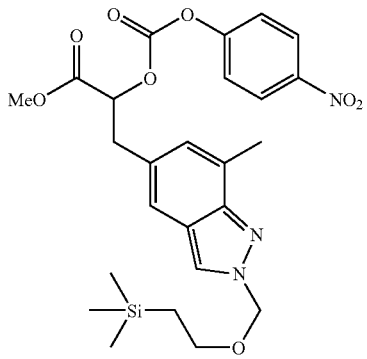

To a solution of methyl 3-(2-((2-(trimethylsilyl)ethoxy)methyl)-7-methyl-2H-indazol-5-yl)-2-hydroxypropanoate (20 mg, 55 μmoles) in pyridine (1 mL) was added 4-nitrophenylchloroformate (55 mg, 5 equiv). The reaction was stirred at room temperature overnight. The reaction was treated with an additional portion of 4-nitrophenylchloroformate (30 mg, 2.7 equiv) and stirred at room temperature for 8 hours. The reaction was poured into diethyl ether, washed with 1M potassium bisulfate until very acidic, then saturated bicarbonate, then 1M sodium hydroxide until most of the nitrophenol had been removed, then brine, dried over sodium sulfate, and concentrated to give 50 mg (quant.) of a pale yellow solid which was used immediately in the next reaction. Mass spec.: 530.30 (MH)$^+$.

1-(Methoxycarbonyl)-2-(2-((2-(trimethylsilyl)ethoxy)methyl)-7-methyl-2H-indazol-5-yl)ethyl 4-(1,2-dihydro-2-oxoquinazolin-3(4H)-yl)piperidine-1-carboxylate

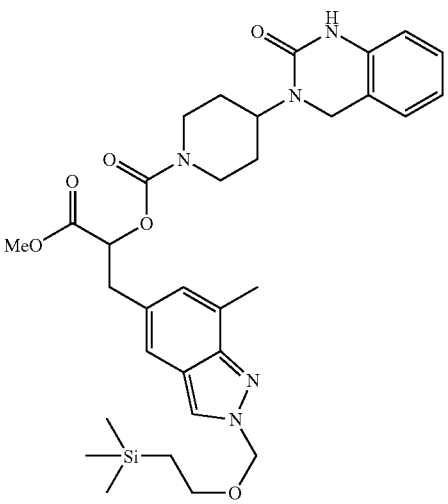

A flask was charged with 1-(methoxycarbonyl)-2-(2-((2-(trimethylsilyl)ethoxy)methyl)-7-methyl-2H-indazol-5-yl)ethyl 4-nitrophenyl carbonate (27 mg, 51 μmoles) and 3,4- dihydro-3-(piperidin-4-yl)quinazolin-2(1H)-one (34 mg, 2.8 equiv). The solids were dissolved in dimethylformamide (1 mL) and treated with diisopropylethylamine (0.1 mL, 11 equiv). The reaction was stirred at room temperature for 2 d. The reaction was concentrated, dissolved in ethyl acetate, washed with 20% potassium hydroxide (3×), then brine, dried over magnesium sulfate, and concentrated. Column chromatography (100% ethyl acetate) removed baseline material to give 50 mg (quant.). Mass spec.: 622.50 (MH)$^+$.

1-(Methoxycarbonyl)-2-(7-methyl-1H-indazol-5-yl) ethyl 4-(1,2-dihydro-2-oxoquinazolin-3(4H)-yl)piperidine-1-carboxylate

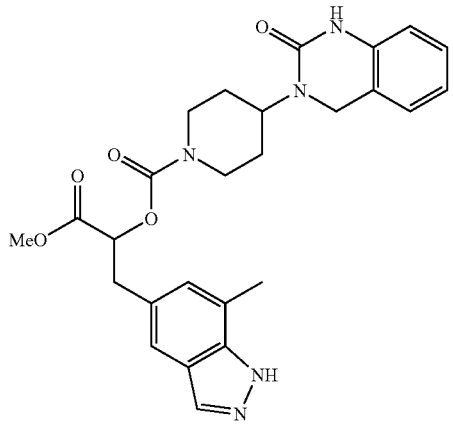

1-(Methoxycarbonyl)-2-(2-((2-(trimethylsilyl)ethoxy) methyl)-7-methyl-2H-indazol-5-yl)ethyl 4-(1,2-dihydro-2-oxoquinazolin-3(4H)-yl)piperidine-1-carboxylate (50 mg, 40 mmoles) was dissolved in trifluoroacetic acid (50% in dichloromethane, 5 mL). After 2 h at room temperature, the reaction was concentrated. Column chromatography (50% ethyl acetate/hexanes->100% ethyl acetate) gave 14.5 mg (37%). Mass spec.: 492.15 (MH)$^+$.

Example 1

3-(7-Methyl-1H-indazol-5-yl)-1-oxo-1-(4-(piperidin-1-yl)piperidin-1-yl)propan-2-yl 4-(1,2-dihydro-2-oxoquinazolin-3(4H)-yl)piperidine-1-carboxylate

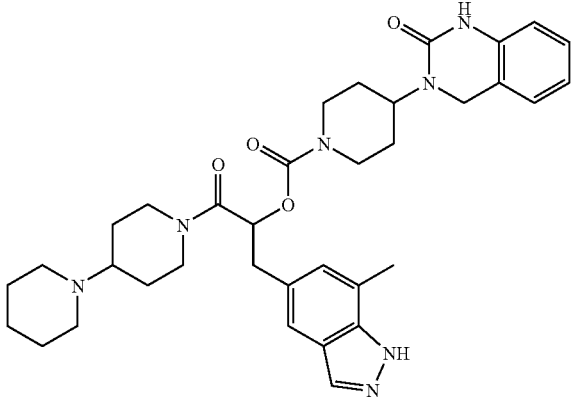

To a solution of 1-(methoxycarbonyl)-2-(7-methyl-1H-indazol-5-yl)ethyl 4-(1,2-dihydro-2-oxoquinazolin-3(4H)-yl) piperidine-1-carboxylate (14.5 mg, 30 μmoles) in methanol (1 mL) was added a solution of lithium hydroxide monohydrate (6.2 mg, 5 equiv) in water (1 mL). The reaction was stirred overnight at room temperature. The reaction was concentrated, dissolved in water, treated with 0.1 mL of 1M hydrochloric acid. A precipitate formed and the reaction was concentrated to give the crude carboxylic acid which was carried on to the next step without purification. Mass spec.: 478.17 (MH)$^+$.

To a solution of the crude acid, 4-piperidinopiperidine (9.9 mg, 2 equiv), and diisopropylethylamine (10 μL, 2 equiv) in dimethylformamide (1 mL) and dichloromethane (1 mL) at 0° C. was added PyBOP® (16 mg, 1.05 equiv). The ice bath was removed and stirring continued for 1 h. The reaction was concentrated and purified by preparative HPLC to give the title compound (16 mg, 73%) as its trifluoroacetic acid salt. $^1$H-NMR (CD$_3$OD) δ 0.10 (m, 0.5), 1.11 (m, 0.5H), 1.50-2.35 (m, 13H), 2.45-3.30 (m, 10H), 3.38 (m, 2H), 3.55 (m, 2H), 4.15-4.70 (m, 6H), 4.85 (m, 1H), 5.76 (m, 1H), 6.98 (d, J=7.6, 1H), 7.14 (dd, J=7.6, 7.3, 1H), 7.20-7.55 (m, 3H), 7.71 (m, 1H), 8.25 (m, 1H). Mass spec.: 628.29 (MH)$^+$.

7-Methyl-2-((2-(trimethylsilyl)ethoxy)methyl)-2-H-indazole-5-carbaldehyde

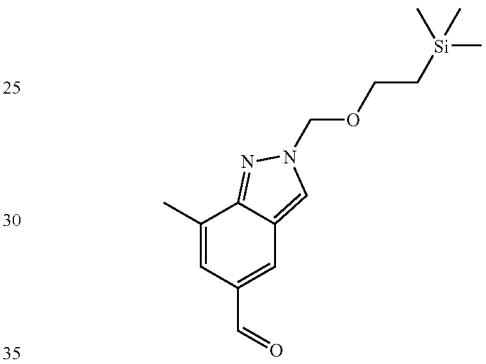

To a solution of 7-methyl-1H-indazole-5-carbaldehyde (5.0 g, 31.25 mmol) and N-methyl-dicyclohexylamine (113.5 mL, 62.35 mmol) in dry tetrahydrofuran (120 mL) at 0° C., was added 2-(trimethylsilyl)ethoxymethyl chloride (6.65 mL, 39.5 mmol). The icebath was removed and stirring continued for 5 h. The reaction mixture was diluted with ethyl acetate, washed with water (2×), brine (2×), dried over sodium sulfate, and concentrated in vacuo. Column chromatography afforded 8.5 g (93%). $^1$H-NMR (CD$_3$OD, 300 MHz) δ -0.04 (s, 9H), 0.83-1.01 (m, 2H), 2.60 (s, 3H), 3.22-3.34 (m, 2H), 3.60-3.76 (m, 2H), 5.58 (s, 2H), 7.54 (s, 1H), 8.23 (s, 1H), 8.64 (s, 1H), 9.91 (s, 1H). Mass spec.: 291.33 (MH)$^+$.

2-Acetoxy-2-(diethoxyphosphoryl)acetic acid

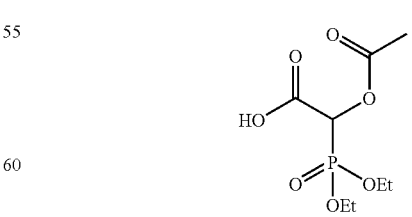

Glyoxylic acid monohydrate (4.0 g, 43.45 mmol) was suspended in diethyl phosphite (5.59 mL, 1.0 equiv), warmed to 60° C., and held there for 5 h. The reaction was cooled, diluted with dichloromethane (40 mL), and treated with pyridine (3.51 mL, 1.0 equiv) and acetyl chloride (3.09 mL, 1.0 equiv). A significant exotherm was noted. The reaction was stirred at room temperature for 2 h. The reaction was washed with 1M hydrochloric acid (2×20 mL), then saturated sodium bicarbonate. The organics were dried over magnesium sulfate, and concentrated to give <2 g as an oil. The aqueous washes were combined and extracted with dichloromethane (4×). The organics were dried over magnesium sulfate and concentrated to give 5.85 g (53%) as an oil which solidified upon standing. $^1$H-NMR (CDCl$_3$, 500 MHz) δ 1.36 (t, J=7.0, 6H), 2.21 (s, 3H), 4.28 (m, 4H), 5.54 (d, J=17.7, 1H), 8.90 (bs, 1H). Mass spec.: 255.10 (MH)$^+$.

Methyl 2-acetoxy-2-(diethylphosphoryl)acetate

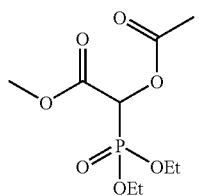

To a heterogeneous mixture of 5 M sodium hydroxide (50 mL) and diethyl ether (100 mL) in a fire-polished erlenmeyer flask at 0° C. was added N-methyl-N'-nitro-N-nitrosoguanidine (6.37 g, 43.3 mmol) in small portions with swirling (no stirbar). After addition was complete, the mixture was allowed to stand at 0° C. for 15 min with occasional swirling. The ethereal was transferred in portions to a suspension of 2-acetoxy-2-(diethoxyphosphoryl)acetic acid (5.50 g, 21.6 mmol) in ether (ca. 50 mL) until the solid had all dissolved and a yellow color persisted. The reaction was allowed to rest at 0° C. for 15 min before bubbling nitrogen through the solution to remove unreacted diazomethane. The reaction was concentrated to give 5.90 g (quant.) as a faint yellow oil. $^1$H-NMR (CDCl$_3$, 500 MHz) δ 1.36 (td, J=7.0, 2.4, 6H), 2.21 (s, 3H), 3.82 (s, 3H), 4.23 (m, 4H), 5.43 (d, J=16.8, 1H). Mass spec.: 269.17 (MH)$^+$.

Methyl 2-acetoxy-3-(7-methyl-2-((2-(trimethylsilyl)ethoxy)methyl)-2H-indazol-5-yl)acrylate

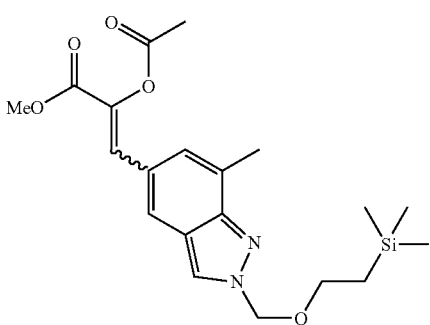

To a solution of methyl 2-acetoxy-2-(diethylphosphoryl)acetate (923 mg, 3.44 mmol) in tetrahydrofuran (7 mL) was added lithium chloride (146 mg, 3.44 mmol). The reaction was stirred until dissolution was complete. The reaction was cooled to −78° C., and treated with N,N,N',N'-tetramethylguanidine (0.43 mL, 3.44 mmol) to give a white suspension which was stirred for 10 min. To this was added the 7-methyl-2-((2-(trimethylsilyl)ethoxy)methyl)-2-H-indazole-5-carbaldehyde (1.00 g, 3.44 mmol) in one portion. The reaction was stirred for 1 h at −78° C., and then allowed to slowly warm to room temperature in the dewar. Allowed to stir overnight at room temperature. The reaction was poured into water/ether. The mixture was extracted with diethyl ether (2×), which were washed with water, then brine, dried over magnesium sulfate, and concentrated. Column chromatography (12% to 25% ethyl acetate/hexanes) gave 825 mg (59%) as a mixture of Z- and E-isomers as a colorless oil. Major (Z isomer): $^1$H-NMR (CDCl$_3$, 500 MHz) δ −0.02 (s, 9H), 0.95 (t, J=8.5, 2H), 2.25 (s, 3H), 2.62 (s, 3H), 3.66 (m, 2H), 3.71 (s, 3H), 5.75 (s, 2H), 6.88 (s, 1H), 7.09 (s, 1H), 7.73 (s, 1H), 8.11 (s, 1H). Mass spec.: 405.17 (MH)$^+$. Minor (E isomer): $^1$H-NMR (CDCl$_3$, 500 MHz) δ −0.02 (s, 9H), 0.95 (t, J=8.5, 2H), 2.36 (s, 3H), 2.62 (s, 3H), 3.66 (m, 2H), 3.85 (s, 3H), 5.74 (s, 2H), 7.32 (s, 1H), 7.38 (s, 1H), 7.78 (s, 1H), 8.14 (s, 1H). Mass spec.: 405.17 (MH)$^+$.

(R)-Methyl 2-acetoxy-3-(7-methyl-2-((2-(trimethylsilyl)ethoxy)methyl)-2H-indazol-5-yl)propanoate

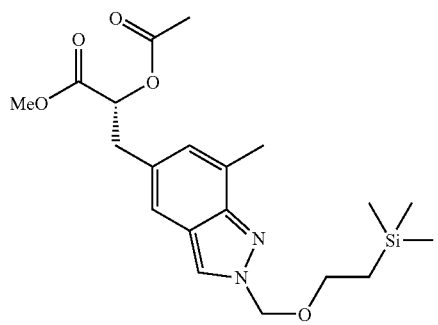

To a solution of methyl 2-acetoxy-3-(7-methyl-2-((2-(trimethylsilyl)ethoxy)methyl)-2H-indazol-5-yl)acrylate (825 mg, 2.04 mmol) in degassed (by bubbling nitrogen) dichloromethane (20.00 mL) under nitrogen was added solid (−)-1,2-bis-((2R,5R)-2,5-diethylpholano)benzene-(cyclooctadiene)rhodium(I) tetrafluoroborate (100.00 mg), all at once. The reaction was placed under a hydrogen atmosphere (55 psi), and shaken for 6 h. The reaction was concentrated and purified by column chromatography (25% ethyl acetate/hexanes) to give 700 mg (84%) as a colorless oil. $^1$H-NMR (CDCl$_3$, 500 MHz) δ −0.03 (s, 9H), 0.94 (t, J=8.2, 2H), 2.07 (s, 3H), 2.61 (s, 3H), 3.11 (dd, J=14.3, 8.9, 1H), 3.20 (dd, J=14.3, 4.6, 1H), 3.64 (t, J=8.5, 2H), 3.72 (s, 3H), 5.26 (dd, J=8.5, 4.6, 1H), 5.72 (s, 2H), 6.93 (s, 1H), 7.33 (s, 1H), 8.02 (s, 1H).

(R)-2-Hydroxy-3-(7-methyl-2-((2-(trimethylsilyl)ethoxy)methyl)-2H-indazol-5-yl)propanoic acid

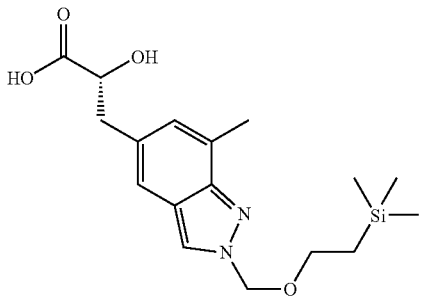

To a solution of (R)-methyl 2-acetoxy-3-(7-methyl-2-((2-(trimethylsilyl)ethoxy)methyl)-2H-indazol-5-yl)propanoate (700 mg, 1.72 mmol) in tetrahydrofuran (6 mL) and methanol (6 mL) at 0° C. was added a solution of lithium hydroxide monohydrate (289 mg, 6.89 mmol) in water (6 mL). The reaction was stirred at 0° C. for 1 h. The reaction was concentrated, dissolved in 5 mL of water, cooled to 0° C., and treated with 1M hydrochloric acid until mildly acidic. A non-solid ppt formed. The suspension was extracted with ethyl acetate (2×), which were washed with brine, dried over magnesium sulfate, and concentrated to give 620 mg (quant.) which was pure by LC/MS and was used without purification. Mass spec.: 351.13 (MH)$^+$.

2-(Methoxymethyl)-7-methyl-2H-indazole-5-carbaldehyde

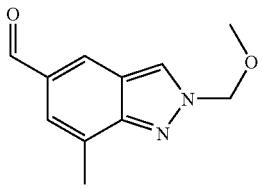

To a solution of 7-methylindazole-5-carboxaldehyde (8.80 g, 54.9 mmol) and N-methyl-dicyclohexylamine (23.6 mL, 110 mmol) in tetrahydrofuran (200 mL) at 0° C. was added chloromethyl methyl ether (7.50 mL, 1.8 equiv). The reaction was allowed to gradually warm to room temperature overnight. The reaction was concentrated, dissolved in diethyl ether, washed with water, then 1 M hydrochloric acid, then water, then brine, dried over magnesium sulfate, and concentrated to give an oil. The oil was dissolved in ethyl acetate and treated with hexanes until lasting turbidity. The suspension was heated until a clear solution was obtained and the flask placed in the freezer. The resulting crystalline solid was crushed with a spatula to break it up, reheated to dissolve some of the solids, and placed in the freezer. The solids were filtered, washed with very cold diethyl ether (−78° C.), and air-dried to give 5.43 g. The mother liquor was concentrated, redissolved in diethyl ether (ca. 20 mL), cooled to −78° C., and treated with a seed crystal of the product. After 1 h, the resulting solids were filtered, washed with cold diethyl ether (−78° C.), and air-dried to give an additional 1.05 g (total yield=58%). $^1$H-NMR (CDCl$_3$, 500 MHz) δ 2.66 (s, 3H), 3.44 (s, 3H), 5.73 (s, 2H), 7.59 (s, 1H), 8.09 (s, 1H), 8.32 (s, 1H), 9.97 (s, 1H). Mass spec.: 205.19 (MH)$^+$.

Methyl 2-acetoxy-3-(2-(methoxymethyl)-7-methyl-2H-indazol-5-yl)acrylate

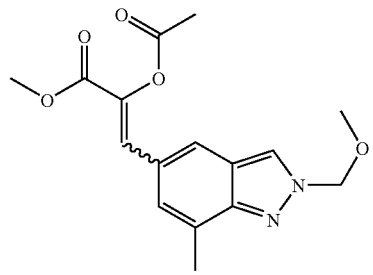

To a solution of methyl 2-acetoxy-2-(diethylphosphoryl)acetate (4.89 g, 18.2 mmol) in tetrahydrofuran (25 mL) was added lithium chloride (0.74 g, 17.5 mmol). The reaction was stirred until dissolution was complete. The reaction was cooled to −78° C., and treated with tetramethylguanidine (2.20 mL, 17.5 mmol) to give a white suspension which was stirred for 10 min. To this was added 2-(methoxymethyl)-7-methyl-2H-indazole-5-carbaldehyde (3.10 g, 15.2 mmol) in one portion. After 10 min, the ice bath was concentrated and the reaction stirred overnight. The reaction was poured onto water/diethyl ether, and the layers separated. The ethereal was washed with water, then brine, dried over magnesium sulfate, and concentrated. Column chromatography gave recovered 2-(methoxymethyl)-7-methyl-2H-indazole-5-carbaldehyde (0.57 g, 18%) and the title compound (2.86 g, 59%) as a mixture of Z- and E-isomers as a colorless oil. Major (Z isomer): $^1$H-NMR (CDCl$_3$, 500 MHz) δ 2.25 (s, 3H), 2.62 (s, 3H), 3.40 (s, 3H), 3.71 (s, 3H), 5.69 (s, 2H), 6.88 (s, 1H), 7.09 (s, 1H), 7.72 (s, 1H), 8.10 (s, 1H). Mass spec.: 319.18 (MH)$^+$. Minor (E isomer): $^1$H-NMR (CDCl$_3$, 500 MHz) δ 2.35 (s, 3H), 2.62 (s, 3H), 3.40 (s, 3H), 3.85 (s, 3H), 5.69 (s, 2H), 7.32 (s, 1H), 7.38 (s, 1H), 7.78 (s, 1H), 8.14 (s, 1H). Mass spec.: 319.18 (MH)$^+$.

(R)-Methyl 2-acetoxy-3-(2-(methoxymethyl)-7-methyl-2H-indazol-5-yl)propanoate

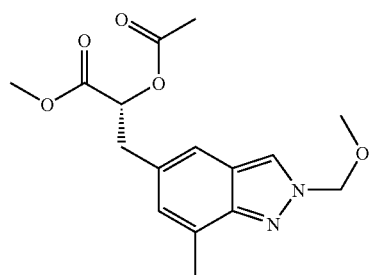

A solution of methyl 2-acetoxy-3-(2-(methoxymethyl)-7-methyl-2H-indazol-5-yl)acrylate (2.80 g, 8.8 mmol) in dichloromethane (20 mL) was degassed by passing a stream of nitrogen through the solution. To this solution was quickly added (−)-1,2-bis((2R,5R)-2,5-diethylphospholano)benzene (cyclooctadiene) rhodium (I) trifluoromethylsulfonate (100 mg, 0.016 equiv) as a solid. The reaction was placed under a hydrogen atmosphere (55 psi) and shaken overnight. The reaction was concentrated and purified by column chromatography (50% ethyl acetate/hexanes) to give 2.74 g (97%) as a colorless oil. $^1$H-NMR (CDCl$_3$, 500 MHz) δ 2.08 (s, 3H), 2.61 (s, 3H), 3.11 (dd, J=14.3, 8.9, 1H), 3.20 (dd, J=14.3, 4.6, 1H), 3.39 (s, 3H), 3.72 (s, 3H), 5.26 (dd, J=8.9, 4.6, 1H), 5.68 (s, 2H), 6.93 (s, 1H), 7.33 (s, 1H), 8.02 (s, 1H).

(R)-2-Hydroxy-3-(2-(methoxymethyl)-7-methyl-2H-indazol-5-yl)propanoic acid

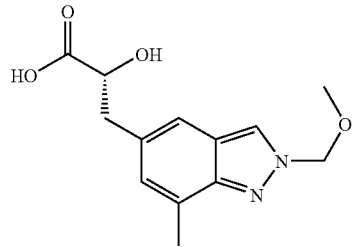

To a solution of (R)-methyl 2-acetoxy-3-(2-(methoxymethyl)-7-methyl-2H-indazol-5-yl)propanoate (2.70 g, 8.4 mmol) in tetrahydrofuran (20 mL) and methanol (20 mL) at 0° C. was added a solution of lithium hydroxide monohydrate (1.41 g, 4.0 equiv) in water (20 mL). The reaction was stirred at 0° C. for 1 h. The reaction was concentrated, dissolved in water (5 mL), cooled to 0° C., and treated with 1M hydrochloric acid until mildly acidic. The solution was was extracted extensively with ethyl acetate and then dichloromethane. The organics were combined, dried over magnesium sulfate, and concentrated to give 1.40 g (63%) as an oil which solidified to a crystalline solid upon standing. $^1$H-NMR (CDCl$_3$, 500 MHz) δ 2.40 (s, 3H), 2.78 (dd, J=14.0, 7.9, 1H), 3.00 (dd, J=14.0, 4.0, 1H), 3.18 (s, 3H), 4.24 (dd, J=7.9, 4.3, 1H), 5.47 (s, 2H), 6.85 (s, 1H), 7.22 (s, 1H), 7.90 (s, 1H). Mass spec.: 265.08 (MH)$^+$.

(R)-Methyl 2-hydroxy-3-(2-(methoxymethyl)-7-methyl-2H-indazol-5-yl)propanoate

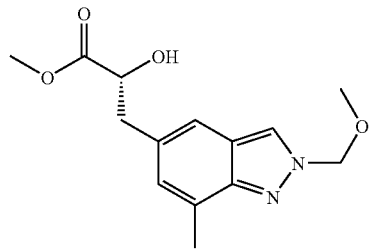

To a heterogeneous mixture of 5 M sodium hydroxide (20 mL) and diethyl ether (60 mL) in a fire-polished erlenmeyer flask at 0° C. was added N-methyl-N'-nitro-N-nitrosoguanidine (1.17 g, 7.95 mmol) in small portions with swirling (no stirbar). After addition was complete, the mixture was allowed to stand at 0° C. for 15 min with occasional swirling. The ethereal was transferred in portions to a suspension of (R)-2-hydroxy-3-(2-(methoxymethyl)-7-methyl-2H-indazol-5-yl)propanoic acid (1.40 g, 5.30 mmol) in dichloromethane (20 mL) until the solid had all dissolved and a yellow color persisted. The reaction was allowed to rest at room temperature for ca. 5 min. before bubbling nitrogen through the solution to remove unreacted diazomethane. The reaction was concentrated and purified by column chromatography (50% to 75% ethyl acetate/hexanes) to give 1.47 g (100%) as a colorless oil. $^1$H-NMR (CDCl$_3$, 500 MHz) δ 1.60 (bs, 1H), 2.58 (s, 3H), 2.95 (dd, J=13.9, 7.0, 1H), 3.14 (dd, J=13.9, 4.0, 1H), 3.36 (s, 3H), 3.76 (s, 3H), 4.46 (bm, 1H), 5.65 (s, 2H), 6.90 (s, 1H), 7.31 (s, 1H), 7.99 (s, 1H). Mass spec.: 279.11 (MH)$^+$.

2-(Benzoyloxy)-2-(diethoxyphosphoryl)acetic acid

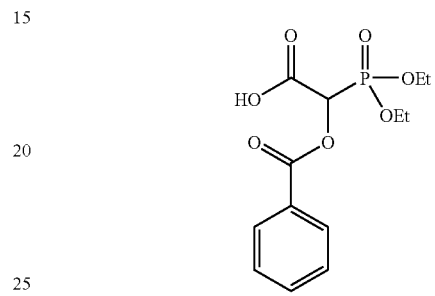

Glyoxylic acid monohydrate (20.10 g, 218 mmol) was suspended in diethyl phosphite (28.1 mL, 1.0 equiv) and warmed to 60° C., and held there for 5 h. The reaction was cooled to 0° C., diluted with dichloromethane (200 mL), and treated with pyridine (17.7 mL, 1.0 equiv) and benzoyl chloride (25.3 mL, 1.0 equiv). The ice bath was removed and stirring continued overnight. The reaction was concentrated, diluted with ethyl acetate, washed with water, then 1M potassium bisulfate, then brine, dried over magnesium sulfate, and concentrated to give an oil. The oil was triturated with ether to give a white powder which was filtered, washed with diethyl ether, and air dried to give 29.0 g (42%). $^1$H-NMR (CDCl$_3$, 500 MHz) δ 1.35 (m, 6H), 4.31 (m, 4H), 5.82 (d, J=17.7, 1H), 7.46 (m, 2H), 7.60 (m, 1H), 7.94 (bs, 1H), 8.12 (m, 2H).

1-(Diethoxyphosphoryl)-2-methoxy-2-oxoethyl benzoate

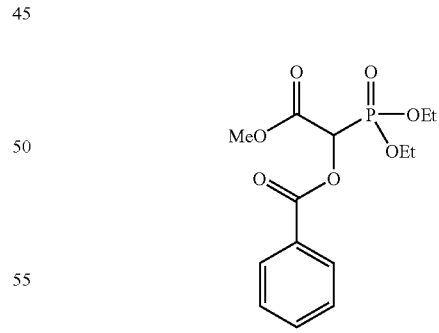

Diazomethane was generated in 3 fire-polished erlenmeyer flasks using ⅓ of each N-methyl-N'-nitro-N-nitrosoguanidine (17.1 g 116. mmol), 5 M sodium hydroxide (200 mL), and diethyl ether (450 mL) at 0° C. by adding the guanidine in small portions with swirling to the other two. After addition was complete, the mixture was allowed to stand at 0° C. for 10 min with occasional swirling. The ethereal was transferred in portions to a suspension of 2-(benzoyloxy)-2-(diethoxyphosphoryl)acetic acid (21.0 g, 66.4 mmol) in dichloromethane (ca. 20 mL) until the solid had all dissolved and a yellow color persisted. The reaction was allowed to rest at 0° C. for 15 min, before bubbling nitrogen through the solution to remove most of the unreacted diazomethane (reaction went almost colorless). The reaction was concentrated to give the 22.0 g (quant.) as a faint yellow oil which was used without purification. ¹H-NMR (CDCl₃, 500 MHz) δ 1.37 (m, 6H), 3.85 (s, 3H), 4.28 (m, 4H), 5.71 (d, J=16.8, 1H), 7.47 (m, 2H), 7.61 (m, 1H), 8.11 (m, 2H).

1-Methoxy-3-(7-methyl-2-((2-(trimethylsilyl)ethoxy) methyl)-2H-indazol-5-yl)-1-oxoprop-2-en-2-yl benzoate

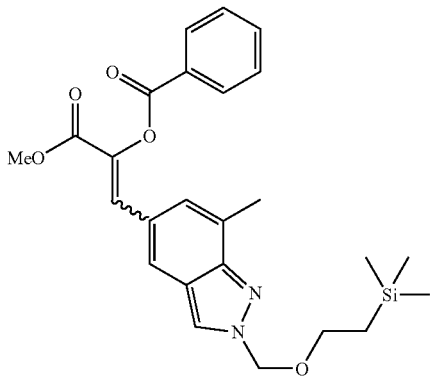

To a solution of 1-(diethoxyphosphoryl)-2-methoxy-2-oxoethyl benzoate (13.7 g, 41.3 mmol) in tetrahydrofuran (70 mL) was added lithium chloride (1.75 g, 41.3 mmol). The reaction was stirred until dissolution was complete. The reaction was cooled to −78° C., and treated with N,N,N',N'-tetramethylguanidine (5.20 mL, 41.3 mmol) to give a white suspension which was stirred for 10 min. To this was added 7-methyl-2-((2-(trimethylsilyl)ethoxy)methyl)-2-H-indazole-5-carbaldehyde (10.0 g, 34.4 mmol) in one portion. The reaction was stirred for 10 min at −78° C., placed in a 0° C. bath, and allowed to slowly warm to room temperature overnight. The reaction was diluted with ethyl acetate, washed with water, then 1M potassium bisulfate, then saturated sodium bicarbonate, then brine, dried over magnesium sulfate, and concentrated. Column chromatography (25% ethyl acetate/hexanes) gave 15.10 g (94%) as a mixture of Z- and E-isomers as a viscous colorless oil. Major (Z isomer): ¹H-NMR (CDCl₃, 500 MHz) δ 0.02 (s, 9H), 0.95 (m, 2H), 2.63 (s, 3H), 3.66 (m, 2H), 3.73 (s, 3H), 5.74 (s, 2H), 7.02 (s, 1H), 7.15 (s, 1H), 7.51 (m, 2H), 7.64 (m, 1H), 7.80 (s, 1H), 8.12 (s, 1H), 8.17 (m, 2H). Mass spec.: 467.18 (MH)⁺. Minor (E isomer): ¹H-NMR (CDCl₃, 500 MHz) δ 0.04 (s, 9H), 0.92 (m, 2H), 2.50 (s, 3H), 3.62 (m, 2H), 3.85 (s, 3H), 5.69 (s, 2H), 7.37 (s, 1H), 7.49 (s, 1H), 7.54 (m, 2H), 7.67 (m, 1H), 7.82 (s, 1H), 8.07 (s, 1H), 8.25 (m, 2H). Mass spec.: 467.18 (MH)⁺.

(R)-1-Methoxy-3-(7-methyl-2-((2-(trimethylsilyl) ethoxy)methyl)-2H-indazol-5-yl)-1-oxopropan-2-yl benzoate

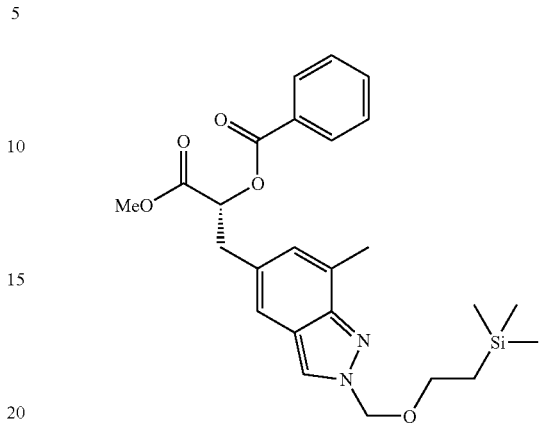

A Parr shaker was purged with nitrogen. A flask containing 1-methoxy-3-(7-methyl-2-((2-(trimethylsilyl)ethoxy)methyl)-2H-indazol-5-yl)-1-oxoprop-2-en-2-yl benzoate (15.7 g, 33.7 mmol) was purged with nitrogen. The substrate was dissolved in dichloromethane (100 mL). The solution was transferred via canula into the Parr shaker and degassed by passing a stream of nitrogen into the solution for 30 min. (−)-1,2-Bis-((2R,5R)-2,5-diethylphospholano)benzene (cyclooctadiene)rhodium(I)tetrafluoroborate (300 mg) was quickly poured into the flask which was re-sealed and purged for an additional 5 min. The Parr shaker was pressurized to 60 psi of hydrogen and shaken overnight. The reaction was concentrated and purified by column chromatography to give 15.5 g (98%) as a colorless oil. Mass spec.: 469.24 (MH)⁺.

(R)-Methyl 2-hydroxy-3-(7-methyl-2-((2-(trimethylsilyl)ethoxy)methyl)-2H-indazol-5-yl)propanoate

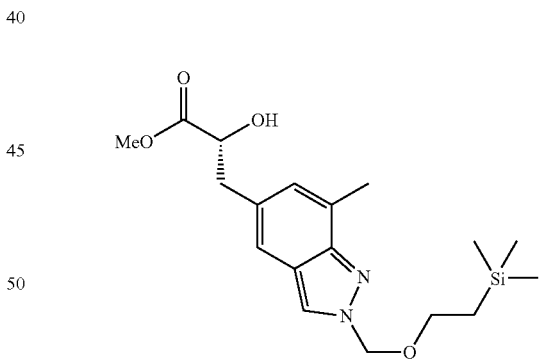

To a solution of (R)-1-methoxy-3-(7-methyl-2-((2-(trimethylsilyl)ethoxy)methyl)-2H-indazol-5-yl)-1-oxopropan-2-yl benzoate (14.2 g, 30.3 mmol) in tetrahydrofuran (80 mL) and methanol (80 mL) at 0° C. was added a solution of lithium hydroxide monohydrate (5.09 g, 121 mmol) in water (80 mL). The reaction was stirred at 0° C. for 1 h. The ice bath was removed and stirring continued at room temperature for 2 h. The reaction was concentrated, dissolved in water (5 mL), cooled to 0° C., and treated with 1M hydrochloric acid until mildly acidic. A non-solid ppt formed. The suspension was extracted with ethyl acetate (3×), which were washed with brine, dried over magnesium sulfate, and concentrated to give the crude hydroxy acid as an oil with white solid forming in it (probably residual benzoic acid) which was used without purification. Mass spec.: 349.34 (M–H)⁻.

To a heterogeneous solution of 5 M sodium hydroxide(150 mL) and diethyl ether (450 mL) in a fire-polished erlenmeyer flask at 0° C. was added N-methyl-N'-nitro-N-nitrosoguanidine (13.4 g, 90.9 mmol) in small portions with swirling (no stirbar). After addition was complete, the mixture was allowed to stand at 0° C. for 15 min with occasional swirling. The ethereal was transferred in portions to a solution of the crude hydroxy acid prepared above in a minimum of diethyl ether until a yellow color persisted. The reaction was allowed to rest at room temperature for 5 min, before bubbling nitrogen through the solution to remove most of the unreacted diazomethane (reaction went almost colorless). The reaction was concentrated and purified by column chromatography (25 to 50% ethyl acetate/hexanes) to give 10.5 g (95%) of the title compound as a colorless oil. $^1$H-NMR (CDCl$_3$, 500 MHz) δ –0.03 (s, 9H), 0.94 (m, 2H), 2.60 (s, 3H), 2.69 (d, J=6.1, 1H), 2.98 (dd, J=14.0, 7.0, 1H), 3.16 (dd, J=13.7, 4.3, 1H), 3.63 (m, 2H), 3.78 (s, 3H), 4.49 (m, 1H), 5.71 (s, 2H), 6.92 (s, 1H), 7.33 (s, 1H), 8.01 (s, 1H). Mass spec.: 365.02 (MH)⁺.

(R)-2-Hydroxy-3-(7-methyl-2-((2-(trimethylsilyl)ethoxy)methyl)-2H-indazol-5-yl)-1-(4-(piperidin-1-yl)piperidin-1-yl)propan-1-one

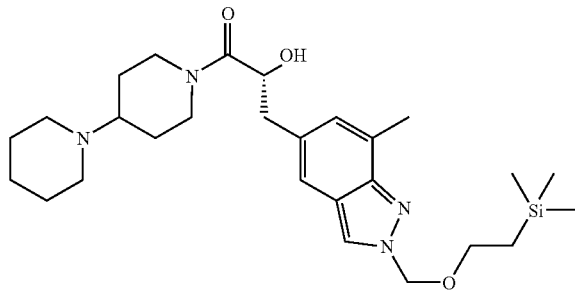

To a solution of the (R)-2-hydroxy-3-(7-methyl-2-((2-(trimethylsilyl)ethoxy)methyl)-2H-indazol-5-yl)propanoic acid (610 mg, 1.74 mmol), diisopropylethylamine (0.61 mL, 3.48 mmol), and 4-piperidinopiperidine (585.76 mg, 2.0 equiv) in dimethylformamide (20 mL) and dichloromethane (20 mL) at 0° C. was added PyBOP® (951 mg, 1.83 mmol). The reaction was stirred at 0° C. for 2 h. The reaction was concentrated, diluted with ethyl acetate, washed with water, then brine, dried over magnesium sulfate, and concentrated. The product was purified by column chromatography (4:96:1 methanol/dichloromethane/triethylamine) to give 795 mg (91%). Mass spec.: 501.40 (MH)⁺.

(R)-3-(7-Methyl-2-((2-(trimethylsilyl)ethoxy)methyl)-2H-indazol-5-yl)-1-oxo-1-(4-(piperidin-1-yl)piperidin-1-yl)propan-2-yl 4-nitrophenyl carbonate

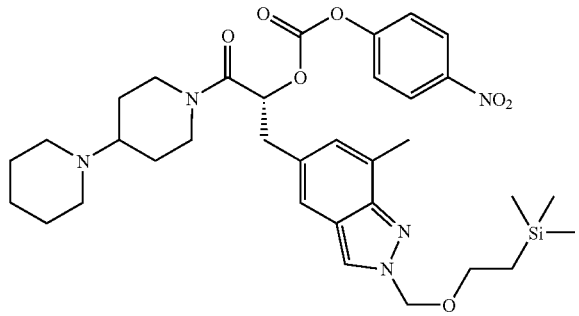

To a solution of (R)-2-hydroxy-3-(7-methyl-2-((2-(trimethylsilyl)ethoxy)methyl)-2H-indazol-5-yl)-1-(4-(piperidin-1-yl)piperidin-1-yl)propan-1-one (795 mg, 1.59 mmol) and diisopropylethylamine (0.55 mL, 3.18 mmol) in dichloromethane (10 mL) at 0° C. was added 4-nitrophenyl-chloroformate (352 mg, 1.10 equiv) followed by dimethylaminopyridine (10 mg). The ice bath was removed and stirring continued for 7 h. The reaction was treated with an additional portion of diisopropylethylamine (0.25 mL, 1.45 mmol), 4-nitrophenyl-chloroformate (352 mg, 1.10 equiv), and dimethylaminopyridine (10 mg) and stirred overnight at room temperature. The reaction was concentrated, dissolved in ethyl acetate, washed with saturated sodium bicarbonate (3×), then brine, dried over magnesium sulfate, and concentrated to give 1.06 g (quant.) as a light brown oil which was used without purification. Mass spec.: 666.31 (MH)⁺.

(R)-3-(7-Methyl-2-((2-(trimethylsilyl)ethoxy)methyl)-2H-indazol-5-yl)-1-oxo-1-(4-(piperidin-1-yl)piperidin-1-yl)propan-2-yl 4-(2-oxo-1,2-dihydroquinazolin-3(4H)-yl)piperidine-1-carboxylate

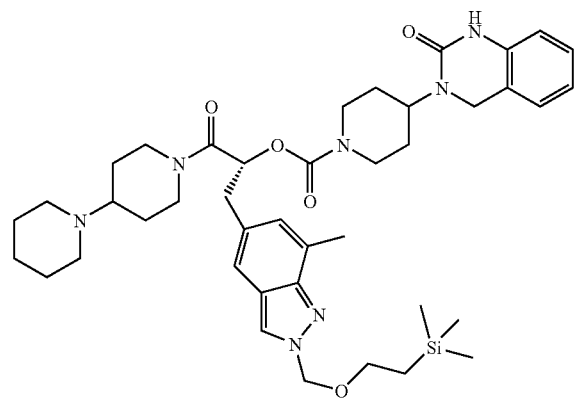

To a solution of (R)-3-(7-methyl-2-((2-(trimethylsilyl)ethoxy)methyl)-2H-indazol-5-yl)-1'-oxo-1'-(4-(piperidin-1-yl)piperidin-1-yl)propan-2-yl 4-nitrophenyl carbonate (150 mg, 0.23 mmol) and 3-(piperidin-4-yl)-3,4-dihydroquinazolin-2(1H)-one (78.2 mg, 1.50 equiv) in dimethylformamide (1 mL) was added diisopropylethylamine (79 μL). The reaction was stirred at room temperature overnight. The reaction was concentrated and purified by column chromatography to give 90 mg (53%) as a colorless film. Mass spec.: 758.56 (MH)⁺.

Example 2

(R-3-(7-Methyl-1-H-indazol-5-yl)-1-oxo-1-(4-(piperidin-1-yl)piperidin-1-yl)propan-2-yl 4-(2-oxo-1,2-dihydroquinazolin-3(4H)-yl)piperidine-1-carboxylate

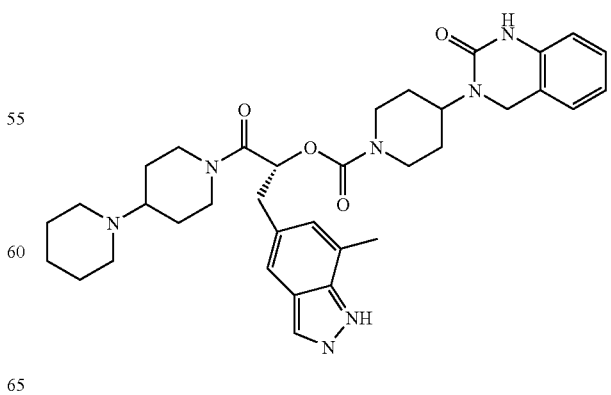

(R)-3-(7-Methyl-2-((2-(trimethylsilyl)ethoxy)methyl)-2H-indazol-5-yl)-1-oxo-1-(4-(piperidin-1-yl)piperidin-1-yl)

propan-2-yl 4-(2-oxo-1,2-dihydroquinazolin-3(4H)-yl)piperidine-1-carboxylate (90 mg, 0.12 mmol) was dissolved in trifluoroacetic acid (50% in dichloromethane, 6 mL) and stirred at room temperature for 2 h. The reaction was concentrated and purified by column chromatography (5:95:1 methanol/dichloromethane/triethylamine). The compound was then dissolved in 10% methanol/dichloromethane and passed through a plug of basic alumina to give 23 mg (31%) as a white solid. $^1$H-NMR (CD$_3$OD, 500 MHz) δ −0.21 (m, 0.7H), 0.74 (m, 1H), 1.10-2.05 (m, 17H), 2.15-2.60 (m, 7H), 2.83 (m, 3H), 3.07 (m, 1.5H), 3.16 (dd, J=12.8, 5.8, 0.7H), 3.70-4.55 (m, 7H), 5.42 (m, 0.3H), 5.50 (dd, J=9.5, 6.1, 0.7H), 6.70 (m, 1H), 6.85 (m, 1H), 6.90-7.15 (m, 3H), 7.40 (bs, 1H), 7.93 (bs, 1H). Mass spec.: 628.34 (MH)$^+$.

(R)-3-(7-Methyl-2-((2-(trimethylsilyl)ethoxy)methyl)-2H-indazol-5-yl)-1-oxo-1-(4-(piperidin-1-yl)piperidin-1-yl)propan-2-yl 4-(8-fluoro-2-oxo-1,2-dihydroquinazolin-3 (4H)-yl)piperidine-1-carboxylate

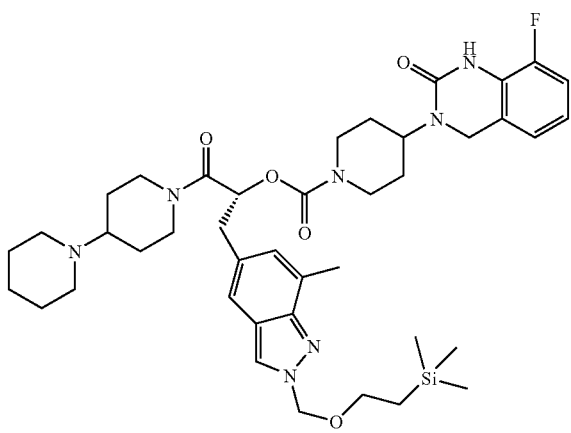

To a solution of (R)-3-(7-methyl-2-((2-(trimethylsilyl)ethoxy)methyl)-2H-indazol-5-yl)-1-oxo-1-(4-(piperidin-1-yl)piperidin-1-yl)propan-2-yl 4-nitrophenyl carbonate (150 mg, 0.23 mmol) and 8-fluoro-3-(piperidin-4-yl)-3,4-dihydroquinazolin-2(1H)-one (84.2 mg, 1.50 equiv) in dimethylformamide (1 mL) was added diisopropylethylamine (79 μL, 0.45 mmol). The reaction was stirred at room temperature overnight. The reaction was concentrated and purified by column chromatography to give 78 mg (45%) as a colorless film. Mass spec.: 776.58 (MH)$^+$.

Example 3

(R)-3-(7-Methyl-1H-indazol-5-yl)-1-oxo-1-(4-(piperidin-1-yl)piperidin-1-yl)propan-2-yl 4-(8-fluoro-2-oxo-1,2-dihydroquinazolin-3(4H)-yl)piperidine-1-carboxylate

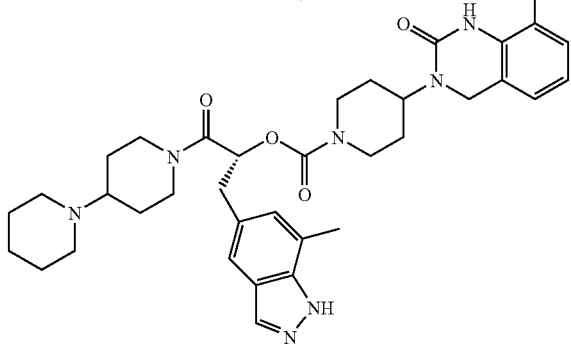

(R)-3-(7-Methyl-2-((2-(trimethylsilyl)ethoxy)methyl)-2H-indazol-5-yl)-1-oxo-1-(4-(piperidin-1-yl)piperidin-1-yl)

propan-2-yl 4-(8-fluoro-2-oxo-1,2-dihydroquinazolin-3(4H)-yl)piperidine-1-carboxylate (78 mg, 0.10 mmol) was dissolved in trifluoroacetic acid (50% in dichloromethane, 6 mL) and stirred at room temperature for 2 h. The reaction was concentrated and purified by column chromatography (5:95:1 methanol/dichloromethane/triethylamine). The residue was dissolved in 10% methanol/dichloromethane and passed through a plug of basic alumina to give 40.1 mg (62%) as a white solid. $^1$H-NMR (CD$_3$OD, 500 MHz) δ −0.20-0.30 (m, 0.6H), 0.80-1.20 (m, 0.7H), 1.40-2.35 (m, 16H), 2.45-2.83 (m, 6H), 2.90-3.48 (m, 5H), 4.00-4.83 (m, 7H), 5.71 (m, 0.3H), 5.79 (dd, J=9.5, 6.1, 0.7H), 7.00-7.25 (m, 3H), 7.25-7.41 (m, 1H), 7.69 (bs, 1H), 8.22 (bs, 1H). Mass spec.: 646.50 (MH)$^+$.

(R)-3-(7-Methyl-2-((2-(trimethylsilyl)ethoxy)methyl)-2H-indazol-5-yl)-1-oxo-1-(4-(piperidin-1-yl)piperidin-1-yl)propan-2-yl 4-(2-oxo-1,2-dihydroquinolin-3-yl)piperidine-1-carboxylate

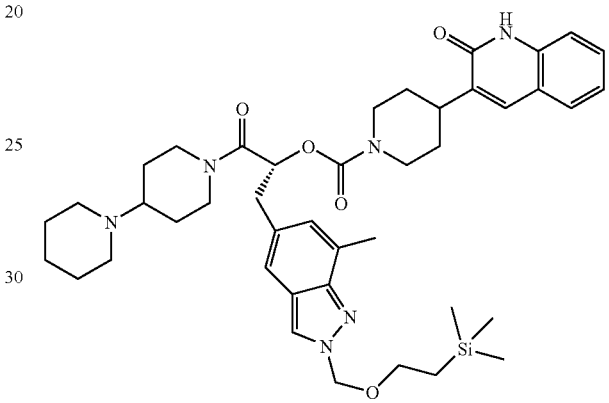

To a solution of (R)-3-(7-methyl-2-((2-(trimethylsilyl)ethoxy)methyl)-2H-indazol-5-yl)-1-oxo-1-(4-(piperidin-1-yl)piperidin-1-yl)propan-2-yl 4-nitrophenyl carbonate (150 mg, 0.23 mmol) and 3-(piperidin-4-yl)quinolin-2(1H)-one hydrochloride (89.5 mg, 1.50 equiv) in dimethylformamide (1 mL) was added diisopropylethylamine (0.16 mL, 0.90 mmol), and stirred at room temperature overnight. The reaction was concentrated and purified by column chromatography to give 102 mg (60%) as a colorless film. Mass spec.: 755.53 (MH)$^+$.

Example 4

(R)-3-(7-Methyl-1H-indazol-5-yl)-1-oxo-1-(4-(piperidin-1-yl)piperidin-1-yl)propan-2-yl 4-(2-oxo-1,2-dihydroquinolin-3-yl)piperidine-1-carboxylate

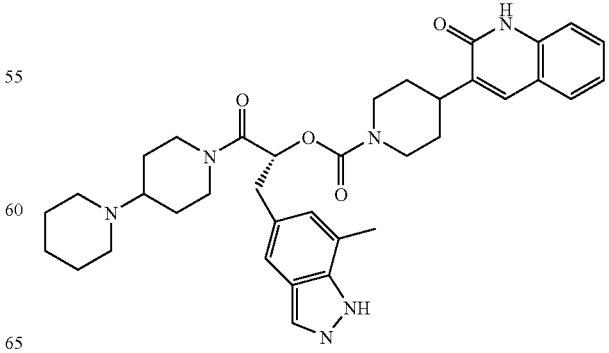

(R)-3-(7-Methyl-2-((2-(trimethylsilyl)ethoxy)methyl)-2H-indazol-5-yl)-1-oxo-1-(4-(piperidin-1-yl)piperidin-1-yl)

propan-2-yl 4-(2-oxo-1,2-dihydroquinolin-3-yl)piperidine-1-carboxylate (102 mg, 0.14 mmol) was dissolved in trifluoroacetic acid (50% in dichloromethane, 6 mL), and stirred at room temperature for 2 h. The reaction was concentrated and purified by column chromatography (5:95:1 methanol/dichloromethane/triethylamine). The residue was dissolved in 10% methanol/dichloromethane and passed through a plug of basic alumina to give 56.4 mg (67%) as a white solid. $^1$H-NMR (CD$_3$OD, 500 MHz) δ −0.50-0.01 (m, 0.7H), 0.50-0.85 (m, 0.8H), 1.00-2.05 (m, 16H), 2.05-2.55 (m, 7H), 2.55-3.00 (m, 4H), 3.00-3.15 (m, 2H), 3.70-4.50 (m, 4H), 5.41 (m, 0.3H), 5.48 (dd, J=9.5, 6.1, 0.6H), 7.01 (m, 1H), 7.11 (m, 1H), 7.21 (m, 1H), 7.36 (m, 2H), 7.44-7.65 (m, 2H), 7.90 (m, 1H). Mass spec.: 625.33 (MH)$^+$.

(R)-3-(7-Methyl-2-((2-(trimethylsilyl)ethoxy)methyl)-2H-indazol-5-yl)-1-oxo-1-(4-(piperidin-1-yl)piperidin-1-yl)propan-2-yl 4-(2-oxo-4-phenyl-2,3-dihydroimidazol-1-yl)piperidine-1-carboxylate

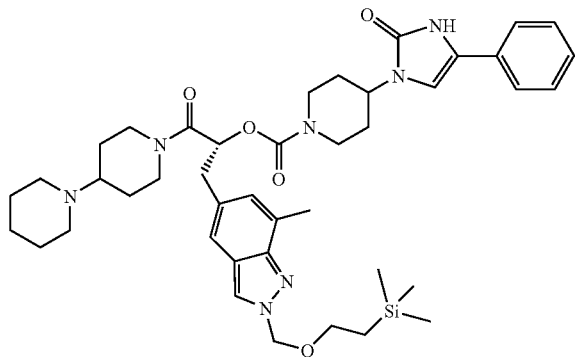

To a solution of (R)-3-(7-methyl-2-((2-(trimethylsilyl)ethoxy)methyl)-2H-indazol-5-yl)-1-oxo-1-(4-(piperidin-1-yl)piperidin-1-yl)propan-2-yl 4-nitrophenyl carbonate (150 mg, 0.23 mmol) and 4-phenyl-(piperidin-4-yl)-1H-imidazol-2(3H)-one (PCT Int. Appl. 1998, WO 9811128 A1) (82.2 mg, 1.50 equiv) in dimethylformamide (1 mL) was added diisopropylethylamine (79 µL, 0.45 mmol) and stirred at room temperature overnight. The reaction was concentrated and purified by column chromatography to give 74 mg (43%) as a colorless film. Mass spec.: 770.57 (MH)$^+$.

Example 5

(R)-3-(7-Methyl-1H-indazol-5-yl)-1-oxo-1-(4-(piperidin-1-yl)piperidin-1-yl)propan-2-yl 4-(2-oxo-4-phenyl-2,3-dihydroimidazol-1-yl)piperidine-1-carboxylate

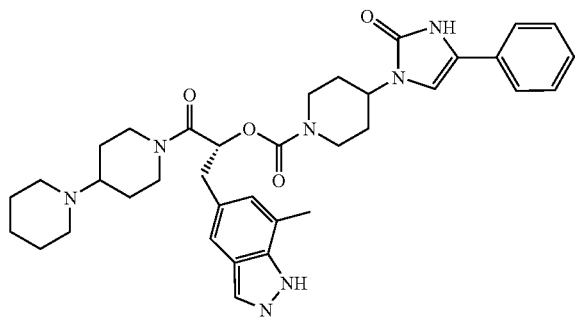

(R)-3-(7-Methyl-2-((2-(trimethylsilyl)ethoxy)methyl)-2H-indazol-5-yl)-1-oxo-1-(4-(piperidin-1-yl)piperidin-1-yl)

propan-2-yl 4-(2-oxo-4-phenyl-2,3-dihydroimidazol-1-yl)piperidine-1-carboxylate (74 mg, 96.1 µmol) was dissolved in trifluoroacetic acid (50% in dichloromethane, 6 mL), and stirred at room temperature for 2 h. The reaction was concentrated and purified by column chromatography (5:95:1 methanol/dichloromethane/triethylamine). The residue was dissolved in 10% methanol/dichloromethane and passed through a plug of basic alumina to give 31.7 (52%) as a white solid. $^1$H-NMR (CD$_3$OD, 500 MHz) δ-0.50-0.10 (m, 0.7H), 0.50-0.90 (m, 1H), 1.05-1.55 (m, 12H), 1.55-2.60 (m, 16H), 2.73 (m, 0.8H), 2.85-3.19 (m, 2.6H), 3.30-3.60 (m, 1H), 3.65-4.18 (m, 3.4H), 4.26 (m, 1H), 4.40 (m, 1H), 5.25-5.57 (m, 1H), 6.90-7.10 (m, 1H), 7.10-7.60 (m, 7H), 7.84-7.97 (bs, 1H). Mass spec.: 638.46 (M−H)$^−$.

tert-Butyl 4-hydroxy-4-(2-oxo-1,2-dihydroquinolin-3-yl)piperidine-1-carboxylate

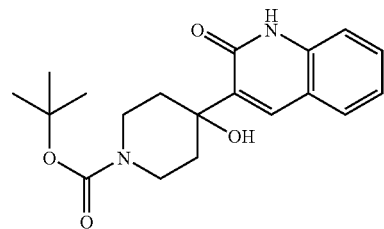

A flask was charged with 3-bromoquinolin-2(1H)-one (U.S. Pat. Appl. Publ. 2002, U.S. 2002099208 A1; Payack, J. F. et al. J. Org. Chem. 2005, 70, 1, 175.) (1.0 g, 4.46 mmol) and sodium hydride (118 mg, 4.91 mmol). The solids were dissolved in tetrahydrofuran (30 mL), stirred for 15 min, and cooled to −78° C. The solution was treated with tert-butyl-lithium (1.7 M in pentane, 5.25 mL, 8.93 mmol) and stirred for 1 h. To this was added N-tert-butoxycarbonyl-4-piperidone (889 mg, 1.0 equiv). The ice bath was removed and stirring continued for 1 h. The reaction was quenched by addition of saturated ammonium chloride. The reaction was diluted with diethyl ether, washed with water (2×), then brine, dried over magnesium sulfate, and concentrated. The resulting oil was triturated with diethyl ether to give a white solid which was filtered, washed with diethyl ether, and air dried to give 430 mg (28%) as a white powder. $^1$H-NMR (CDCl$_3$, 500 MHz) δ 1.48 (s, 9H), 1.57 (bs, 2H), 1.87 (m, 2H), 2.13 (m, 2H), 3.37 (m, 2H), 4.06 (m, 2H), 7.28 (m, 2H), 7.53 (m, 2H), 7.60 (m, 1H), 7.69 (s, 1H). Mass spec.: 367.35 (MNa)$^+$.

3-(4-Hydroxypiperidin-4-yl)quinolin-2(1H)-one

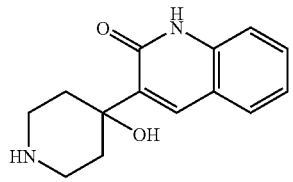

tert-Butyl 4-hydroxy-4-(2-oxo-1,2-dihydroquinolin-3-yl)piperidine-1-carboxylate (300 mg, 0.87 mmol) was dissolved in trifluoroacetic acid (50% in dichloromethane, 6 mL). The reaction was stirred 30 min and concentrated. The residue was dissolved in water, extracted with dichloromethane (2×) which were discarded. The aqueous was made basic with solid potassium carbonate. The resulting solid was filtered to give 145 mg (68%) as a white powder. Mass spec.: 245.35 (MH)+.

(R)-3-(7-Methyl-2-((2-(trimethylsilyl)ethoxy)methyl)-2H-indazol-5-yl)-1-oxo-1-(4-(piperidin-1-yl)piperidin-1-yl)propan-2-yl 4-hydroxy-4-(2-oxo-1,2-dihydroquinolin-3-yl)piperidine-1-carboxylate

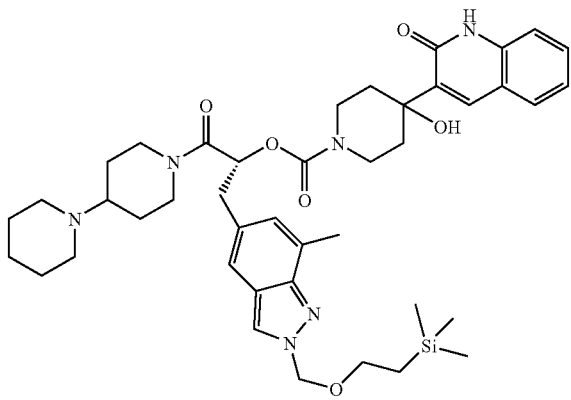

To a solution of (R)-3-(7-methyl-2-((2-(trimethylsilyl)ethoxy)methyl)-2H-indazol-5-yl)-1-oxo-1-(4-(piperidin-1-yl)piperidin-1-yl)propan-2-yl 4-nitrophenyl carbonate (150 mg, 0.23 mmol) and 3-(4-hydroxypiperidin-4-yl)quinolin-2(1H)-one (55 mg, 1.0 equiv) in dimethylformamide (1 mL) was added diisopropylethylamine (79 μL, 0.45 mmol). The reaction was stirred at room temperature overnight. The reaction was concentrated and purified by column chromatography (3:97:1 methanol/dichloromethane/triethylamine) to give 90 mg (52%) as a foam solid. Mass spec.: 771.48 (MH)+.

Example 6

(R)-3-(7-Methyl-1H-indazol-5-yl)-1-oxo-1-(4-(piperidin-1-yl)piperidin-1-yl)propan-2-yl 4-hydroxy-4-(2-oxo-1,2-dihydroquinolin-3-yl)piperidine-1-carboxylate

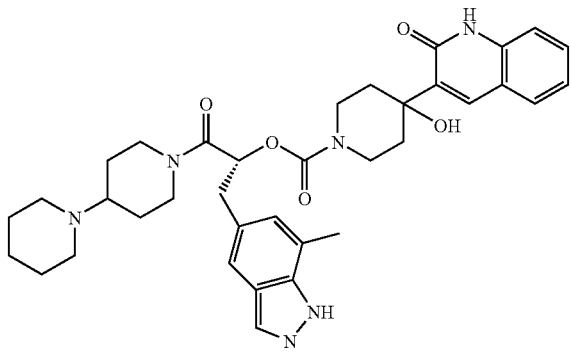

(R)-3-(7-Methyl-2-((2-(trimethylsilyl)ethoxy)methyl)-2H-indazol-5-yl) 1-oxo-1-(4-(piperidin-1-yl)piperidin-1-yl)propan-2-yl 4-hydroxy-4-(2-oxo-1,2-dihydroquinolin-3-yl)piperidine-1-carboxylate (90 mg, 0.12 mmol) was dissolved in trifluoroacetic acid (50% in dichloromethane, 6 mL) and stirred at room temperature for 2 h. The reaction was concentrated and purified by column chromatography (5:95:1 to 10:90:1 methanol/dichloromethane/triethylamine). The residue was dissolved in 10% methanol/dichloromethane and passed through a plug of basic alumina to give 41 mg (55%) as a white solid. $^1$H-NMR (CD$_3$OD, 500 MHz) δ −0.40-0.00 (m, 0.6H), 0.50-0.95 (m, 0.7H), 1.10-2.75 (m, 21H), 2.83 (m, 0.7H), 3.02-3.65 (m, 6H), 3.68-4.35 (m, 3H), 4.37-4.57 (m, 1H), 5.40-5.65 (m, 1H), 7.00-7.15 (m, 1H), 7.15-7.25 (m, 1H), 7.25-7.35 (m, 1H), 7.40-7.52 (m, 2H), 7.57-7.70 (m, 1H), 7.87-8.03 (m, 1H). Mass spec.: 641.61 (MH)+.

(R)-3-(7-Methyl-2-((2-(trimethylsilyl)ethoxy)methyl)-2H-indazol-5-yl)-1-oxo-1-(4-(piperidin-1-yl)piperidin-1-yl)propan-2-yl 4-(7-fluoro-2-oxo-1,2-dihydroquinazolin-3 (4H)-yl)piperidine-1-carboxylate

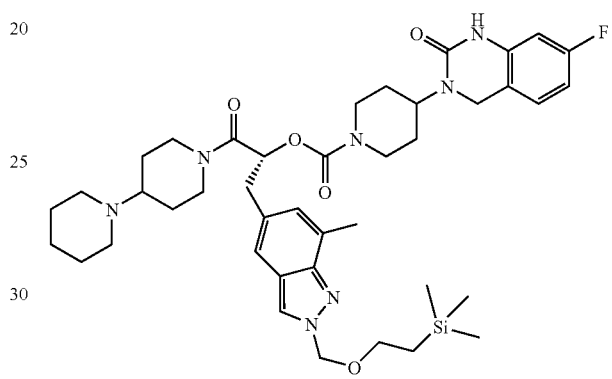

To a solution of (R)-3-(7-methyl-2-((2-(trimethylsilyl)ethoxy)methyl)-2H-indazol-5-yl)-1-oxo-1-(4-(piperidin-1-yl)piperidin-1-yl)propan-2-yl 4-nitrophenyl carbonate (150 mg, 0.23 mmol) and 7-fluoro-3-(piperidin-4-yl)-3,4-dihydroquinazolin-2(1H)-one (56.2 mg, 1.0 equiv) in dimethylformamide (1 mL) was added diisopropylethylamine (79 μL, 0.45 mmol) and the reaction stirred at room temperature overnight. The reaction was concentrated and purified by column chromatography (3:97:1 methanol/dichloromethane/triethylamine) to give 93 mg (53%) as a tan foam solid. Mass spec.: 776.48 (MH)+.

Example 7

(R)-3-(7-Methyl-1H-indazol-5-yl)-1-oxo-1-(4-(piperidin-1-yl)piperidin-1-yl)propan-2-yl 4-(7-fluoro-2-oxo-1,2-dihydroquinazolin-3(4H)-yl)piperidine-1-carboxylate

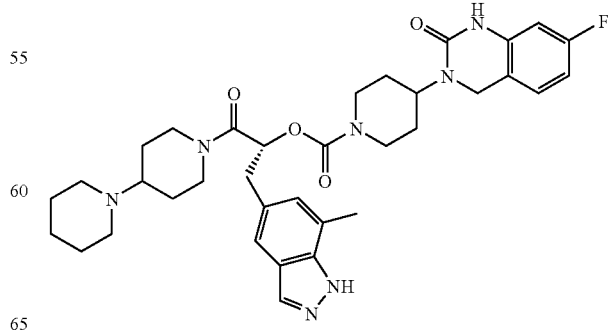

(R)-3-(7-Methyl-2-((2-(trimethylsilyl)ethoxy)methyl)-2H-indazol-5-yl)-1-oxo-1-(4-(piperidin-1-yl)piperidin-1-yl)

propan-2-yl 4-(7-fluoro-2-oxo-1,2-dihydroquinazolin-3 (4H)-yl)piperidine-1-carboxylate (93 mg, 0.12 mmol) was dissolved in trifluoroacetic acid (50% in dichloromethane, 6 mL) and stirred at room temperature for 2 h. The reaction was concentrated and purified by column chromatography (5:95:1 to 10:90:1 methanol/dichloromethane/triethylamine). The residue was dissolved in 10% methanol/dichloromethane and passed through a plug of basic alumina to give 41 mg (53%) as a white powder. $^1$H-NMR (CD$_3$OD, 500 MHz) δ −0.38-0.15 (m, 0.7H), 0.60-0.95 (m, 1H), 1.18-2.18 (m, 17H), 2.29 (m, 0.7H), 2.35-2.50 (m, 3H), 2.58-3.01 (m, 3.4H), 3.01-3.25 (m, 2.4H), 3.65-4.60 (m, 7H), 5.47 (m, 0.4H), 5.55 (dd, J=9.5, 6.1, 0.7H), 6.51 (m, 0.8H), 6.62 (m, 0.8H), 6.90-7.20 (m, 2.2H), 7.45 (bs, 1.1H), 7.98 (bs, 1H). Mass spec.: 648.64 (MH)$^+$.

(R)-Methyl 3-(2-(methoxymethyl)-7-methyl-2H-indazol-5-yl)-2-((4-nitrophenoxy)carbonyloxy)propanoate

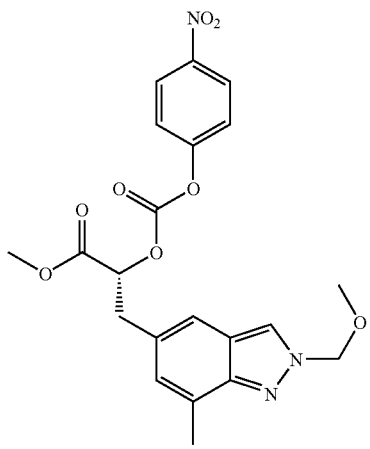

To a solution of (R)-methyl 2-hydroxy-3-(2-(methoxymethyl)-7-methyl-2H-indazol-5-yl)propanoate (1.45 g, 5.21 mmol) and diisopropylethylamine (2.73 mL, 3.0 equiv) in dichloromethane (27 mL) at 0° C. was added 4-nitrophenyl-chloroformate (1.58 g, 1.5 equiv) and N,N-dimethylaminopyridine (10 mg). The ice bath was removed and stirring continued for 7 h. The reaction was treated with an additional portion of diisopropylethylamine (1.5 mL, 1.65 equiv), 4-nitrophenyl-chloroformate (1.6 g, 1.5 equiv), and N,N-dimethylaminopyridine (10 mg) and stirred overnight. The reaction was concentrated, dissolved in ethyl acetate, washed with water, then 1M potassium bisulfate, then saturated sodium bicarbonate (5×), then brine, dried over magnesium sulfate, and concentrated to give 6.0 g (quant.) as a light brown oil, which was used immediately without purification. Mass spec.: 444.10 (MH)$^+$.

(R)-1-Methoxy-3-(2-(methoxymethyl)-7-methyl-2H-indazol-5-yl)-1-oxopropan-2-yl 4-(2-oxo-1,2-dihydroquinolin-3-yl)piperidine-1-carboxylate

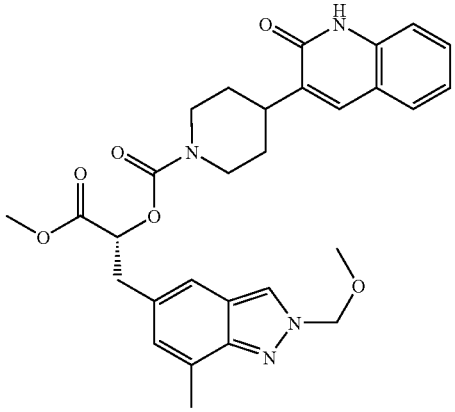

A flask was charged with (R)-methyl 3-(2-(methoxymethyl)-7-methyl-2H-indazol-5-yl)-2-((4-nitrophenoxy)carbonyloxy)propanoate (2.31 g, 5.20 mmol), 3-(piperidin-4-yl)quinolin-2(1H)-one (1.78 g, 1.5 equiv), diisopropylethylamine (1.82 mL, 2.0 equiv), and dimethylformamide (20 mL). The reaction was stirred at room temperature for 8 h and concentrated under vacuum. The resulting residue was dissolved in ethyl acetate and washed with water to give a suspension which was exhaustively extracted with ethyl acetate then dichloromethane. The organics were dried over magnesium sulfate and concentrated. Column chromatography (25% ethyl acetate/hexanes to 10% methanol/ethyl acetate) gave 2.40 g (86%) as a light yellow foam solid. Mass spec.: 533.30 (MH)$^+$.

(R)-1-Methoxy-3-(7-methyl-1H-indazol-5-yl)-1-oxopropan-2-yl 4-(2-oxo-1,2-dihydroquinolin-3-yl)piperidine-1-carboxylate

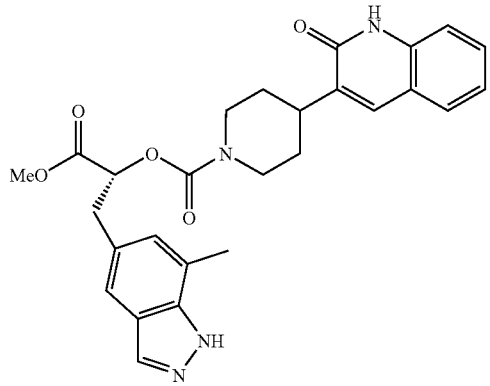

To a solution of (R)-1-methoxy-3-(2-(methoxymethyl)-7-methyl-2H-indazol-5-yl)-1-oxopropan-2-yl 4-(2-oxo-1,2-dihydroquinolin-3-yl)piperidine-1-carboxylate (1.20 g, 2.25 mmol) in methanol (20 mL) was added acetyl chloride (0.40 mL, 5.62 mmol). The reaction was warmed to reflux and held there for 1 h. The reaction was concentrated by rotary evaporation under high vacuum and purified by column chromatography (5% methanol/dichloromethane) to give 1.09 g (99%) as a white foam solid. Mass spec.: 489.29 (MH)$^+$.

(R)-3-(7-Methyl-1H-indazol-5-yl)-2-(4-(2-oxo-1,2-dihydroquinolin-3-yl)piperidine-1-carbonyloxy)propanoic acid

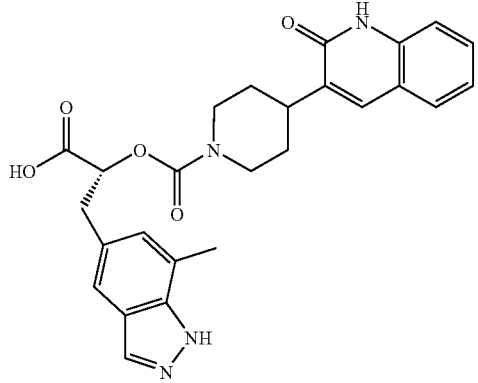

To a solution of (R)-1-methoxy-3-(7-methyl-1H-indazol-5-yl)-1-oxopropan-2-yl 4-(2-oxo-1,2-dihydroquinolin-3-yl)piperidine-1-carboxylate (1.20 g, 2.46 mmol) in methanol (10 mL) and tetrahydrofuran (10 mL) at 0° C. was added a precooled solution of lithium hydroxide monohydrate (309 mg, 3.0 equiv) in water (10 mL). After 2 h, the reaction was concentrated under high vaccuum (<25° C.). The resulting residue was dissolved in water (20 mL), cooled to 0° C., and acidified to ca. pH 2 with 1 N hydrochloric acid. The suspension was maintained at 0° C. for 1 h, filtered, and the solid washed with cold water. The resulting white solid was air dried and then dried under high vacuum overnight to give 1.04 g (89%) as a white solid. Mass spec.: 475.30 (MH)$^+$.

Example 4

(R)-3-(7-Methyl-1H-indazol-5-yl)-1-oxo-1-(4-(piperidin-1-yl)piperidin-1-yl)propan-2-yl 4-(2-oxo-1,2-dihydroquinolin-3-yl)piperidine-1-carboxylate

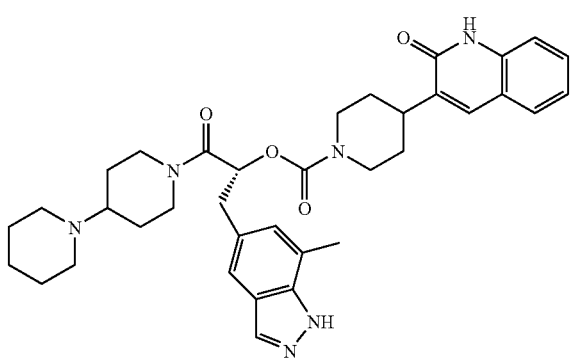

To a solution of (R)-3-(7-methyl-1H-indazol-5-yl)-2-(4-(2-oxo-1,2-dihydroquinolin-3-yl)piperidine-1-carbonyloxy)propanoic acid (500 mg, 1.05 mmol), diisopropylethylamine (0.37 mL, 2.11 mmol), and 4-piperidinopiperidine (355 mg, 2.0 equiv) in dimethylformamide (4 mL) and dichloromethane (4 mL) at 0° C. was added PyBOP® (576 mg, 1.11 mmol). The reaction was stirred at 0° C. for 4 h, was concentrated, and purified by column chromatography (95:5:1 to 93:7:1 dichloromethane/methanol/triethylamine). The resulting residue was dissolved in 5% methanol/dichloromethane and passed through a basic alumina column to give 600 mg (88%) as a white powder. Mass spec.: 625.56 (MH)$^+$.

tert-Butyl 4-(5,6-dihydropyridin-1(2H)-yl)piperidine-1-carboxylate

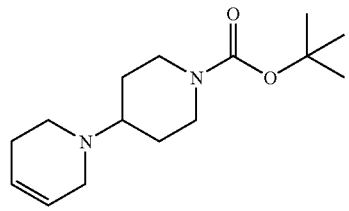

4-Oxo-piperidine-1-carboxylic acid tert-butyl ester (797 mg, 4 mmol), 1,2,3,6-tetrahydropyridine (349 mg, 4.2 mmol), sodium cyanoborohydride (126 mg, 2 mmol), zinc chloride (410 mg, 3.2 mmol), and anhydrous methanol (20 mL) were mixed together and the mixture stirred overnight at room temperature. The solvent was evaporated from the mixture and the residue partitioned between 1 N sodium hydroxide and dichloromethane. The phases were separated and the aqueous layer extracted with dichloromethane. The organic extracts were combined, dried over magnesium sulfate, and the solvent evaporated. The residue was purified by flash column chromatography (1:1 hexanes/ethyl acetate to ethyl acetate to 1:3 methanol/ethyl acetate) to give 800 mg (75%) as a colorless oil. $^1$H-NMR (CDCl$_3$, 400 MHz) δ 5.75-5.70 (m, 1H), 5.68-5.64 (m, 1H), 4.13-4.07 (m, 2H), 3.08 (m, 2H), 2.71-2.60 (m, 4H), 2.48-2.41 (m, 1H), 2.15 (m, 2H), 1.82-1.79 (m, 2H), 1.49-1.38 (m, 11H).

1-(Piperidin-4-yl)-1,2,3,6-tetrahydropyridine

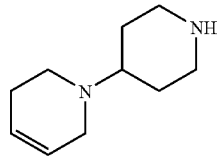

tert-Butyl 4-(5,6-dihydropyridin-1 (2H)-yl)piperidine-1-carboxylate (800 mg, 3 mmol) was dissolved in dichloromethane (54 ml). To this was added trifluoroacetic acid (7.9 ml) and triethyl silane (1.2 ml). The mixture was stirred at room temperature for 3 h. Solvent was removed from the mixture en vacuo. The residue was dissolved in saturated sodium bicarbonate (50 ml) and stirred for 30 min. Sodium hydroxide (50 ml, 50% in water) was added to the solution which was then extracted with dichloromethane (3×100 ml). The organic extract was dried over sodium sulfate and the solvent evaporated to give 370 mg (74%) as a colorless oil. $^1$H-NMR (CDCl$_3$, 400 MHz) δ 5.74-5.70 (m, 1H), 5.68-5.64 (m, 1H), 3.14-3.07 (m, 4H), 2.64-2.53 (m, 4H), 2.43-2.37 (m, 1H), 2.15 (m, 2H), 1.85-1.82 (m, 2H), 1.73 (s, 1H), 1.47-1.38 (m, 2H).

Example 8

(R)-1-(4-(5,6-Dihydropyridin-1(2H)-yl)piperidin-1-yl)-3-(7-methyl-1H-indazol-5-yl)-1-oxopropan-2-yl 4-(2-oxo-1,2-dihydroquinolin-3-yl)piperidine-1-carboxylate

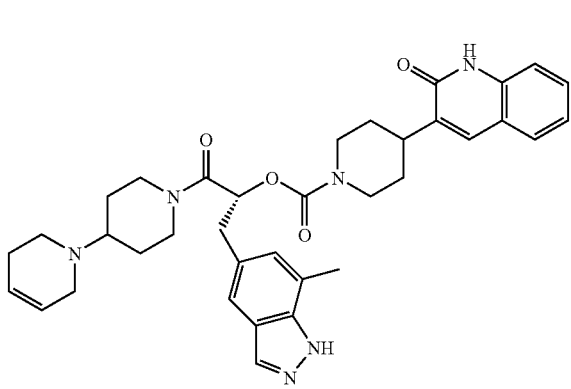

To a solution of (R)-3-(7-methyl-1H-indazol-5-yl)-2-(4-(2-oxo-1,2-dihydroquinolin-3-yl)piperidine-1-carbonyloxy) propanoic acid (50 mg, 0.11 mmol), diisopropylethylamine (37 µL, 0.21 mmol), and 1-(piperidin-4-yl)-1,2,3,6-tetrahydropyridine (75.7 mg, 2.0 equiv) in dimethylformamide (0.50 mL) and dichloromethane (0.50 mL) at 0° C. was added PyBOP® (57.6 mg, 0.11 mmol). The reaction was stirred at 0° C. for 4 h. The reaction was concentrated and purified by column chromatography (95:5:1 to 90:10:1 dichloromethane/methanol/triethylamine). The resulting residue was dissolved in 5% methanol/dichloromethane and passed through a basic alumina column to give 35.9 mg (53%) as a white powder. $^1$H-NMR (CD$_3$OD, 500 MHz) δ −0.35-0.15 (m, 0.7H), 0.60-0.93 (m, 1H), 1.15-2.20 (m, 11H), 2.30-3.25 (m, 11H), 3.75-4.58 (m, 4H), 5.35-5.75 (m, 3H), 7.01-7.14 (m, 1H), 7.18 (m, 1H), 7.28 (m, 1H), 7.36-7.50 (m, 2H), 7.53-7.73 (m, 2H), 7.90-8.01 (m, 1H). Mass spec.: 623.33 (MH)$^+$.

3-Methyl-3,9-diaza-spiro[5.5]undecane dihydrochloride

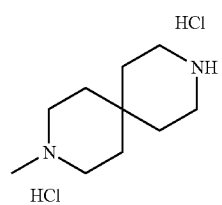

3-Benzyl-9-methyl-3,9-diaza-spiro[5.5]undecane (Rice, L. M. et al. *J Heterocyclic Chem.* 1964, 1, 3, 125.) (1.2 g, 4.65 mmol) was dissolved in ethanol (20 mL). To this solution was added hydrochloric acid (4 N in dioxane, 3 mL) and palladium (10% on charcoal, 500 mg). The reaction was shaken on a Parr shaker overnight under 60 psi of hydrogen. The reaction mixture was filtered through a pad of celite, concentrated, and the residue treated with a mixture of ethyl acetate and hexanes, to yield 670 mg (60%) as a white powder. $^1$H-NMR (CD$_3$OD) δ 1.68-1.72 (m, 4H), 2.88 (s, 3H), 3.16-3.22 (m, 6H), 3.38 (m, 2H). Mass spec.: 169.12 (MH)$^+$.

Example 9

(R)-3-(7-Methyl-1H-indazol-5-yl)-1-oxo-1-(9-methyl-3,9-diaza-spiro[5.5]undecan-3-yl)propan-2-yl 4-(2-oxo-1,2-dihydroquinolin-3-yl)piperidine-1-carboxylate

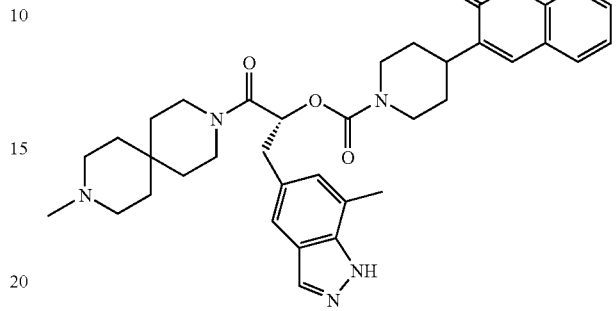

To a solution of (R)-3-(7-methyl-1H-indazol-5-yl)-2-(4-(2-oxo-1,2-dihydroquinolin-3-yl)piperidine-1-carbonyloxy) propanoic acid (50 mg, 0.11 mmol), diisopropylethylamine (37 UL, 0.21 mmol), and 3-methyl-3,9-diaza-spiro[5.5]undecane dihydrochloride (65.2 mg, 2.0 equiv) in dimethylformamide (0.50 mL) and dichloromethane (0.50 mL) at 0° C. was added PyBOP® (57.6 mg, 0.11 mmol). The reaction was stirred at 0° C. for 4 h. The reaction was concentrated and purified by column chromatography (95:5:1 to 90:10:1 dichloromethane/methanol/triethylamine). The resulting residue was dissolved in 5% methanol/dichloromethane and passed through a basic alumina column to give 52 mg (77%) as a white powder. $^1$H-NMR (CD$_3$OD, 500 MHz) δ 0.12-0.55 (m, 1H), 0.85-1.70 (m, 1H), 1.85 (m, 2H), 2.05-2.42 (m, 8H), 2.50 (s, 3H), 2.73-3.30 (m, 8H), 3.65 (bs, 1H), 4.00-4.43 (m, 2H), 5.46 (dd, J=7.6, 7.6, 1H), 7.07 (s, 1H), 7.17 (m, 1H), 7.27 (m, 1H), 7.38-7.46 (m, 2H), 7.50 (bs, 0.5H), 7.58 (m, 1H), 7.65 (bs, 0.5H), 7.96 (s, 1H). Mass spec.: 625.33 (MH)$^+$.

Example 10

(R)-3-(7-Methyl-1H-indazol-5-yl)-1-oxo-1-(piperidin-1-yl)propan-2-yl 4-(2-oxo-1,2-dihydroquinolin-3-yl)piperidine-1-carboxylate

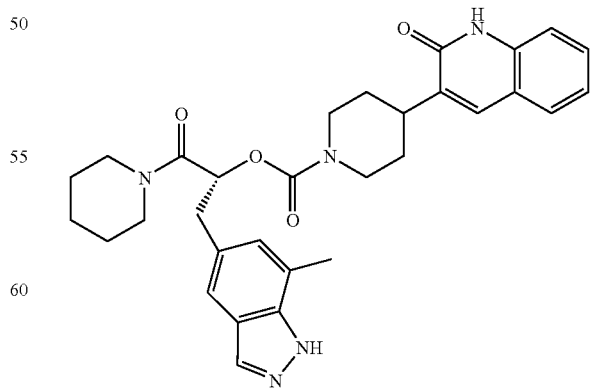

To a solution of (R)-3-(7-methyl-1H-indazol-5-yl)-2-(4-(2-oxo-1,2-dihydroquinolin-3-yl)piperidine-1-carbonyloxy)

propanoic acid (50 mg, 0.11 mmol), diisopropylethylamine (37 μL, 0.21 mmol), and piperidine (21 μL, 2.0 equiv) in dimethylformamide (0.5 mL) and dichloromethane (0.5 mL) at 0° C. was added PyBOP® (57.6 mg, 0.11 mmol). The reaction was stirred at 0° C. for 4 h. The reaction was concentrated and purified by column chromatography (95:5:1 to 90:10:1 dichloromethane/methanol/triethylamine). The resulting residue was dissolved in 5% methanol/dichloromethane and passed through a basic alumina column to give 55 mg (93%) as a white powder. $^1$H-NMR (CD$_3$OD, 500 MHz) δ 0.75-1.70 (m, 9H), 1.70-1.95 (m, 4H), 2.51 (s, 3H), 2.72-3.04 (m, 3H), 3.11 (m, 4H), 3.19-3.58 (m, 4H), 3.98-4.49 (m, 2H), 5.47 (dd, J=7.3, 7.3, 1H), 7.07 (s, 1H), 7.17 (m, 1H), 7.27 (m, 1H), 7.43 (m, 2.5H), 7.58 (d, J=7.3, 1H), 7.65 (bs, 0.5H), 7.96 (s, 1H). Mass spec.: 542.29 (MH)$^+$.

Example 11

(R)-1-(4-Cyclohexylpiperazin-1-yl)-3-(7-methyl-1H-indazol-5-yl)-1-oxopropan-2-yl 4-(2-oxo-1,2-dihydroquinolin-3-yl)piperidine-1-carboxylate

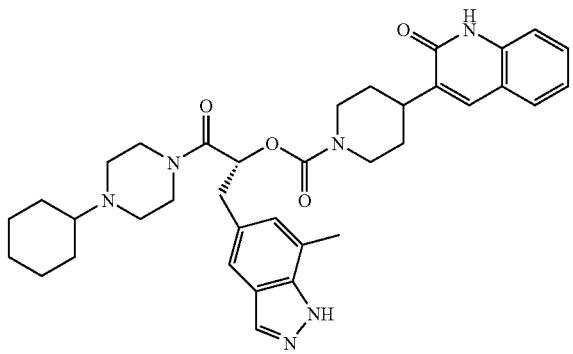

To a solution of (R)-3-(7-methyl-1H-indazol-5-yl)-2-(4-(2-oxo-1,2-dihydroquinolin-3-yl)piperidine-1-carbonyloxy) propanoic acid (50 mg, 0.11 mmol), diisopropylethylamine (37 μL, 0.21 mmol), and 1-cyclohexylpiperazine (35.5 mg, 2.0 equiv) in dimethylformamide (0.50 mL) and dichloromethane (0.50 mL) at 0° C. was added PyBOP® (57.6 mg, 0.11 mmol). The reaction was stirred at 0° C. for 4 h. The reaction was concentrated and purified by column chromatography (95:5:1 to 90:10:1 dichloromethane/methanol/triethylamine). The resulting residue was dissolved in 5% methanol/dichloromethane and passed through a basic alumina column to give 62.3 mg (92%) as a white powder. $^1$H-NMR (CD$_3$OD, 500 MHz) δ 0.75-2.10 (m, 20H), 2.29 (m, 1H), 2.47 (m, 1H), 2.56 (s, 3H), 2.77-3.41 (m, 9H), 3.73 (m, 1H), 4.04-4.49 (m, 2H), 5.52 (dd, J=8.2, 7.3, 1H), 7.11 (s, 1H), 7.22 (dd, J=7.0, 7.0, 1H), 7.33 (d, J=7.9, 1H), 7.42-7.53 (m, 2H), 7.53-7.76 (m, 2H), 8.01 (s, 1H). Mass spec.: 625.33 (MH)$^+$.

Example 12

(R)-1-(4-(4-Fluorophenyl)piperazin-1-yl)-3-(7-methyl-1H-indazol-5-yl)-1-oxopropan-2-yl 4-(2-oxo-1,2-dihydroquinolin-3-yl)piperidine-1-carboxylate

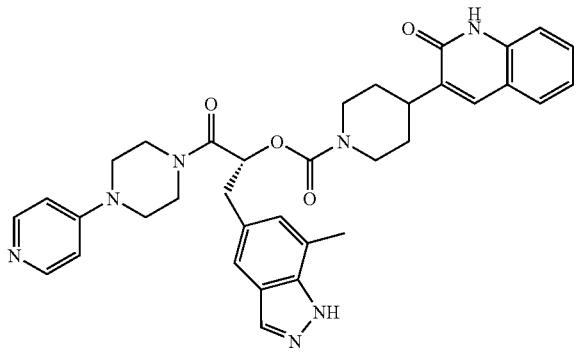

To a solution of (R)-3-(7-methyl-1H-indazol-5-yl)-2-(4-(2-oxo-1,2-dihydroquinolin-3-yl)piperidine-1-carbonyloxy) propanoic acid (50 mg, 0.11 mmol), diisopropylethylamine (37 μL, 0.21 mmol), and N-(4-fluorophenyl)piperazine (38.0 mg, 2.0 equiv) in dimethylformamide (0.50 mL) and dichloromethane (0.50 mL) at 0° C. was added PyBOP® (57.6 mg, 0.11 mmol). The reaction was stirred at 0° C. for 4 h. The reaction was concentrated and purified by column chromatography (95:5:1 to 90:10:1 dichloromethane/methanol/triethylamine). The resulting residue was dissolved in 5% methanoudichloromethane and passed through a basic alumina column to give 71.2 mg (quant.) as a white powder. $^1$H-NMR (CD$_3$OD, 500 MHz) δ 1.25-1.75 (m, 2H), 1.75-2.25 (m, 9H), 2.51 (s, 3H), 2.75 (m, 1H), 2.75-3.30 (m, 13H), 3.48 (m, 3H), 3.80 (m, 1H), 4.05-4.50 (m, 2H), 5.55 (dd, J=7.6, 7.3, 1H), 6.68 (m, 2H), 6.91 (m, 1H), 7.11 (s, 1H), 7.21 (dd, J=7.9, 7.3, 1H), 7.32 (d, J=8.2, 1H), 7.47 (dd, J=7.9, 7.3, 1H), 7.51 (m, 1.5H), 7.61 (d, J=7.6, 1H), 7.67 (bs, 0.5H), 8.00 (s, 1H). Mass spec.: 637.28 (MH)$^+$.

Example 13

(R)-3-(7-Methyl-1H-indazol-5-yl)-1-oxo-1-(4-(pyridin-4-yl)piperazin-1-yl)propan-2-yl 4-(2-oxo-1,2-dihydroquinolin-3-yl)piperidine-1-carboxylate To a solution of (R)-3-(7-methyl-1H-indazol-5-yl)-2-(4-(2-oxo-1,2-dihydroquinolin-3-yl)piperidine-1-carbonyloxy) propanoic acid (50 mg, 0.11 mmol), diisopropylethylamine (37 μL, 0.21 mmol), and 1-(4-pyridyl)piperazine (34.4 mg, 2.0 equiv) in dimethylformamide (0.50 mL) and dichloromethane (0.50 mL) at 0° C. was added PyBOP® (57.6 mg, 0.11 mmol). The reaction was stirred at 0° C. for 4 h, was concentrated, and purified by column chromatography (95:5:1 to 90:10:1 dichloromethane/methanol/triethylamine). The resulting residue was dissolved in 5% methanol/dichloromethane and passed through a basic alumina column to give 53.8 mg (80%) as a white powder. $^1$H-NMR (CD$_3$OD, 500 MHz) δ 1.25-2.00 (m, 4H), 2.51 (s, 3H), 2.67 (bs, 1H), 2.80-3.31 (m, 7H), 3.35-3.83 (m, 5H), 4.05-4.49 (m, 2H), 5.52 (dd, J=7.6, 7.3, 1H), 6.64 (bs, 2H), 7.12 (s, 11H), 7.22 (dd, J=7.0, 7.0, 1H), 7.32 (d, J=8.2, 1H), 7.47 (m, 1H), 7.52 (m, 1.5H), 7.62 (d, J=7.0, 11H), 7.69 (bs, 0.5H), 7.99 (s, 1H), 8.10 (m, 2H). Mass spec.: 620.28 (MH)$^+$.

(±)-2-Hydroxy-3-(7-methyl-2-((2-(trimethylsilyl)ethoxy)methyl)-2H-indazol-5-yl)propanoic acid

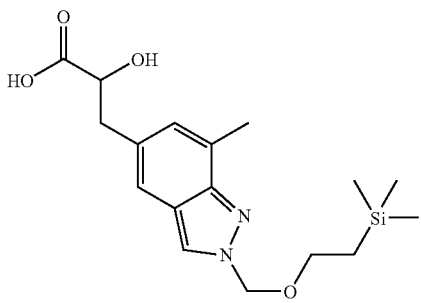

A Parr bottle was charged with 1-methoxy-3-(7-methyl-2-((2-(trimethylsilyl)ethoxy)methyl)-2H-indazol-5-yl)-1-oxo-prop-2-en-2-yl benzoate (1.0 g, 2.14 mmol), methanol (15 mL), and palladium (10% on charcoal, 100 mg). The Parr shaker was pressurized to 60 psi of hydrogen and shaken for 6 h. The reaction was filtered through celite and concentrated. The resulting residue was dissolved in tetrahydrofuran (8 mL) and methanol (8 mL) and cooled to 0° C. To this was added a solution of lithium hydroxide monohydrate (358 mg, 8.54 mmol) in water (8 mL). The reaction was stirred at 0° C. for 1 h, then at room temperature for 2 h. The reaction was concentrated, dissovled in water, cooled to 0° C., and acidified with 1M hydrochloric acid. The resulting mixture was extracted with ethyl acetate (2×). The organics were washed with a minimum of brine, dried over magnesium sulfate, and concentrated. Column chromatography (5% to 10% methanol/dichloromethane) gave 340 mg (45%) as a colorless oil. $^1$H-NMR (CDCl$_3$, 500 MHz) 8-0.04 (s, 9H), 0.93 (m, 2H), 2.53 (s, 3H), 2.92 (m, 1H), 3.19 (m, 1H), 3.61 (m, 2H), 4.46 (bs, 1H), 5.68 (s, 2H), 6.93 (s, 1H), 7.31 (bs, 1H), 7.94 (bs, 1H). Mass spec.: 351.36 (MH)$^+$.

(±)-2-Hydroxy-3-(7-methyl-2-((2-(trimethylsilyl)ethoxy)methyl)-2H-indazol-5-yl)-1-(4-(piperidin-1-yl)piperidin-1-yl)propan-1-one

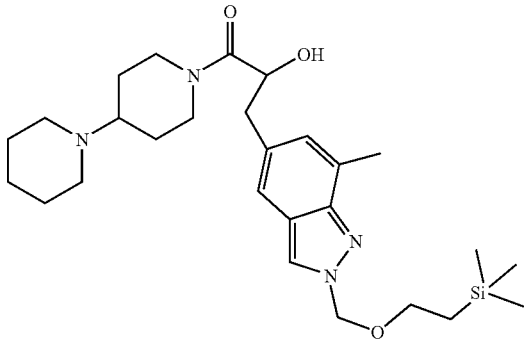

To a solution of (±)-2-hydroxy-3-(7-methyl-2-((2-(trimethylsilyl)ethoxy)methyl)-2H-indazol-5-yl)propanoic acid (100 mg, 0.29 mmol), 4-piperidinopiperidine (96.0 mg, 2.0 equiv), and diisopropylethylamine (0.10 mL, 0.57 mmol) in dichloromethane (3.6 mL) at 0° C. was added PyBOP® (156 mg, 0.30 mmol) in two portions. The reaction was stirred at 0° C. for 15 minutes and at room temperature overnight. The reaction was diluted with ethyl acetate, washed with water (2×), then brine, dried over magnesium sulfate, and concentrated. Column chromatography (4% to 10% methanol/dichloromethane) gave 130 mg (91%) as an oil. Mass spec.: 501.36 (MH)$^+$.

(±)-3-(7-Methyl-2-((2-(trimethylsilyl)ethoxy)methyl)-2H-indazol-5-yl)-1-oxo-1-(4-(piperidin-1-yl)piperidin-1-yl)propan-2-yl 4-(2-oxo-1,2-dihydroquinolin-3-yl)piperidine-1-carboxylate

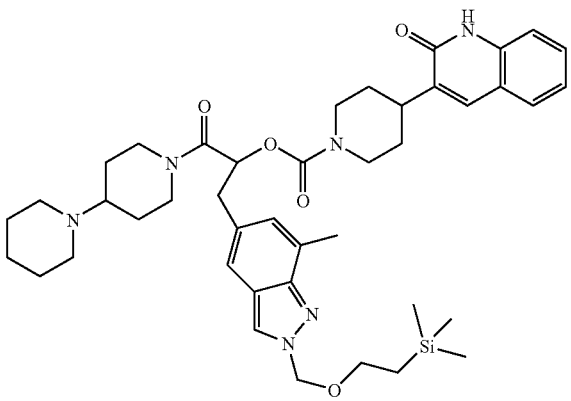

To a solution of (±)-2-hydroxy-3-(7-methyl-2-((2-(trimethylsilyl)ethoxy)methyl)-2H-indazol-5-yl)-1-(4-(piperidin-1-yl)piperidin-1-yl)propan-1-one (130 mg, 0.26 mmol) and diisopropylethylamine (91 μL, 0.52 mmol) in dichloromethane (1 mL) at 0° C. was added 4-nitrophenyl-chloroformate (57.6 mg, 1.10 equiv). The ice bath was removed and stirring continued for 4 h. The reaction was treated with a solution of 3-(piperidin-4-yl)quinolin-2(1H)-one (88.9 mg, 1.50 equiv) and diisopropylethylamine (91 μL, 0.52 mmol) in dimethylformamide (1 mL). The reaction was stirred at room temperature overnight. The reaction was poured into water/dichloromethane. The mixture was extracted with dichloromethane (2×) which was washed with saturated sodium bicarbonate, then water (2×), then brine, dried over magnesium sulfate, and concentrated. Column chromatography (5% to 20% methanol/dichloromethane) gave 112 mg (57%) as an oil.

Example 14

(±)-3-(7-Methyl-1H-indazol-5-yl)-1-oxo-1-(4-(piperidin-1-yl)piperidin-1-yl)propan-2-yl 4-(2-oxo-1,2-dihydroquinolin-3-yl)piperidine-1-carboxylate

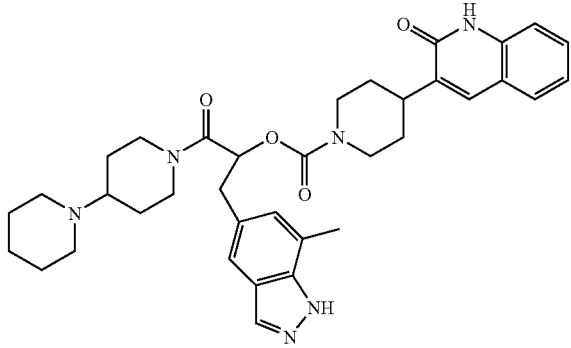

(±)-3-(7-Methyl-2-((2-(trimethylsilyl)ethoxy)methyl)-2H-indazol-5-yl)-1-oxo-1-(4-(piperidin-1-yl)piperidin-1-yl)propan-2-yl 4-(2-oxo-1,2-dihydroquinolin-3-yl)piperidine-1-carboxylate (112 mg, 0.15 mmol) was dissolved in trifluoroacetic acid (50% in dichloromethane, 6 mL) and stirred at room temperature for 2 h. The reaction was concentrated and purified by column chromatography (5% methanol/dichloromethane to 7:93:1 methanol/dichloromethane/33% trimethylamine in ethanol) gave 89.6 mg (97%) as a white solid. Mass spec.: 755.37 (MH)⁺.

(R)-1-Methoxy-3-(7-methyl-2-((2-(trimethylsilyl)ethoxy)methyl)-2H-indazol-5-yl)-1-oxopropan-2-yl 4-(8-fluoro-2-oxo-1,2-dihydroquinolin-3-yl)piperidine-1-carboxylate

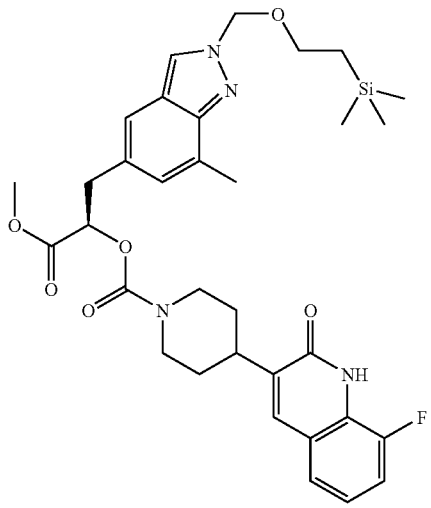

(R)-Methyl 3-(4-methyl-2-((2-(trimethylsilyl)ethoxy)methyl)-2H-indazol-6-yl)-2-((4-nitrophenoxy)carbonyloxy)propanoate (75 mg, 0.24 mmol) was dissolved in N,N-dimethylformamide (6 mL). N,N-Diisopropylethylamine (1.5 mL, 8.6 mmol) was added to the mixture followed by 8-fluoro-3-(piperidin-4-yl)quinolin-2(1H)-one hydrochloride (75 mg, 0.27 mmol). The reaction stirred at room temperature for 3 h. The mixture was diluted with ethyl acetate (20 mL), washed successively with water (2×), 1 N hydrochloric acid, and brine. The organic layer was dried (magnesium sulfate), filtered, and concentrated in vacuo. The title compound was obtained as white solid in 82% yield and used without further purification. Mass spec.: 637.2 (MH)⁺.

(R)-2-(4-(8-Fluoro-2-oxo-1,2-dihydroquinolin-3-yl)piperidine-1-carbonyloxy)-3-(7-methyl-2-((2-(trimethylsilyl)ethoxy)methyl)-2H-indazol-5-yl)propanoic acid

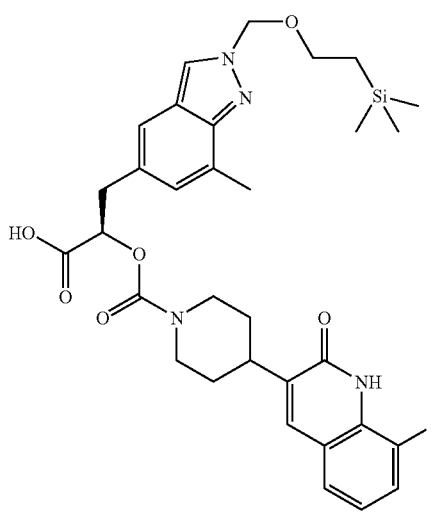

(R)-1-Methoxy-3-(4-methyl-2-((2-(trimethylsilyl)ethoxy)methyl)-2H-indazol-6-yl)-1-oxopropan-2-yl 4-(8-fluoro-2-oxo-1,2-dihydroquinolin-3-yl)piperidine-1-carboxylate (120 mg, 0.19 mmol) was dissolved in tetrahydrofuran (3 mL). Water (2 mL) was added to the mixture followed by lithium hydroxide monohydrate (25 mg, 0.60 mmol). The reaction was stirred at room temperature for 3 h and quenched by the addition of 1 N hydrochloric acid. The mixture was extracted with ethyl acetate (2×). The combined organics were dried (magnesium sulfate), filtered, and concentrated in vacuo. The title compound was obtained without further purification as white solid in 95% yield. Mass spec.: 621.1 (M–H)⁻.

(R)-3-(7-Methyl-2-((2-(trimethylsilyl)ethoxy)methyl)-2H-indazol-5-yl)-1-oxo-1-(4-(piperidin-1-yl)piperidin-1-yl)propan-2-yl 4-(8-fluoro-2-oxo-1,2-dihydroquinolin-3-yl)piperidine-1-carboxylate

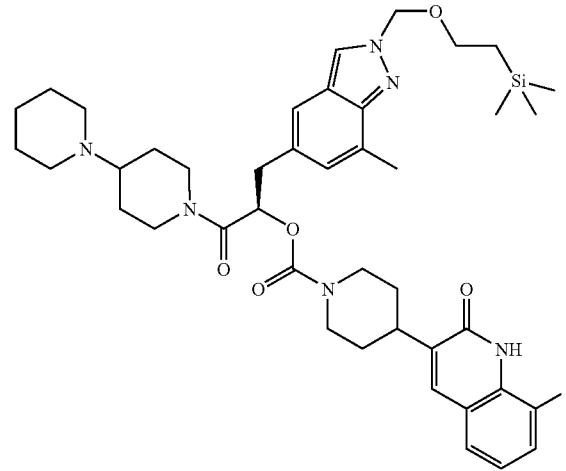

(R)-2-(4-(8-Fluoro-2-oxo-1,2-dihydroquinolin-3-yl)piperidine-1-carbonyloxy)-3-(7-methyl-2-((2-(trimethylsilyl)

ethoxy)methyl)-2H-indazol-5-yl)propanoic acid (105 mg, 0.17 mmol) was dissolved in N,N-dimethylformamide (3 mL). N,N-Diisopropylethylamine (100 µL, 0.57 mmol) was added to the mixture followed by o-benzotriazol-1-yl-N,N,N'-tetramethyluronium tetrafluoroborate (65 mg, 0.20 mmol). The reaction was stirred at room temperature for 5 min. 4-Piperidinopiperidine (41 mg, 0.22 mmol) was added to the mixture. The reaction was stirred at room temperature for 2 h. The mixture was diluted with ethyl acetae (25 mL), washed successively with water (3x), and brine. The organic layer was dried (magnesium sulfate), filtered, and concentrated in vacuo. The title compound was obtained without further purification as white solid in 96% yield. Mass spec.: 773.3 (MH)⁺.

Example 15

(R)-3-(7-Methyl-1H-indazol-5-yl)-1-oxo-1-(4-(piperidin-1-yl)piperidin-1-yl)propan-2-yl 4-(8-fluoro-2-oxo-1,2-dihydroquinolin-3-yl)piperidine-1-carboxylate

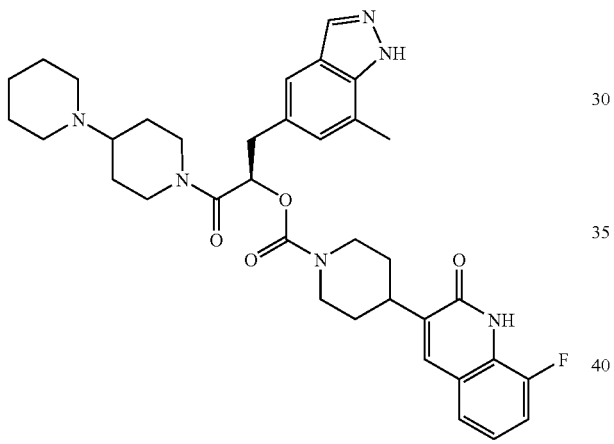

(R)-3-(7-Methyl-2-((2-(trimethylsilyl)ethoxy)methyl)-2H-indazol-5-yl)-1-oxo-1-(4-(piperidin-1-yl)piperidin-1-yl) propan-2-yl 4-(8-fluoro-2-oxo-1,2-dihydroquinolin-3-yl)piperidine-1-carboxylate (122 mg, 0.16 mmol) was dissolved in ethyl acetate (2 mL). Hydrochloric acid (4 N in dioxane, 3.0 mL) was added to the mixture. The reaction was stirred at room temperature for 18 h. The reaction mixture was concentrated en vacuo and purified by preparatory HPLC. Organic solvents were removed from the product fractions. The remaining aqueous solution was made basic with aqueous sodium bicarbonate and was extracted with ethyl acetate (2x). The combined organic extracts were dried (magnesium sulfate), filtered, and concentrated in vacuo. The title compound was obtained as an off-white solid in 59% yield. ¹H NMR (500 MHz, DMSO-d6): δ 13.03 (s, 1H), 11.78 (s, 1H), 7.99 (s, 1H), 7.70 (m, 1H), 7.46 (m, 3H), 7.34 (dd, J=10.81, 8.09, 1H), 7.15 (m, 1H), 7.06 (s, 1H), 5.43 (m, 1H), 4.34 (m, 1H), 4.17 (m, 1H), 3.88 (m, 1H), 3.06 (m, 2H), 2.97 (m, 2H), 2.83 (m, 3H), 2.50 (m, 3H), 2.36 (m, 2H), 2.27 (m, 1H), 2.05 (m, 2H), 1.82 (d, J=12.51, 2H), 1.68 (m, 1H), 1.39 (m, 10H), 0.78-0.26 (m, 1H). Mass spec.: 643.3425 (MH)⁺.

tert-Butyl 2-fluorophenylcarbamate

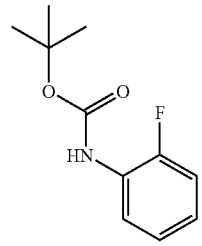

To a solution of di-tert-butyldicarbonate (90.4 g, 414 mmol) in tetrahydrofuran (414 mL) was added 2-fluorobenzenamine (40.0 mL, 414 mmol). The reaction was heated at reflux overnight. The reaction was cooled, concentrated, dissolved in pentane, washed, in order, with 1 N potassium bisulfate (2x), water, 20% potassium hydroxide, and brine, and then dried over magnesium sulfate and concentrated to give a light brown oil which was dried under high vacuum to give 83.7 g (96%) as a light brown oil which was used without further purification. ¹H-NMR (CDCl₃, 500 MHz) δ 1.52 (s, 9H), 6.68 (bs, 1H), 6.85-7.20 (m, 3H), 8.07 (dd, J=8.1, 8.1 Hz, 1H). Mass spec.: 234.18 (MNa)⁺.

tert-Butyl 2-fluoro-6-formylphenylcarbamate

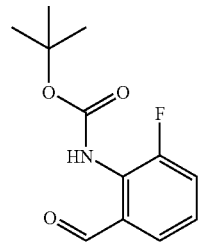

tert-Butyl 2-fluorophenylcarbamate (42.7 g, 202 mmol) was concentrated from toluene in vacuo (3x) to remove any traces of water. The resulting residue was dissolved in tetrahydrofuran (600 mL), and cooled to −78° C. To this was added tert-butyllithium (1.7 M in pentane, 285 mL, 485 mmol) in dropwise fashion. After addition was complete, the reaction was stirred at −78° C. for 30 minutes. The solution was allowed to gradually warm to −20° C. before re-cooling to −78° C. To this was added dimethylformamide (46.9 mL, 606 mmol). The reaction was allowed to gradually warm to room temperature overnight. The reaction was poured into a separatory funnel containing diethyl ether and water. The organics were washed with water (3x) and concentrated. The combined aqueous washes were neutralized with 1 M potassium bisulfate and extracted with diethyl ether. The ethereal layers were combined with the other organics, washed with water, then brine, dried over magnesium sulfate, and concentrated to give 48.1 g (100%) as a yellow oil which was used without further purification. 1H-NMR (CDCl₃, 500 MHz) δ 1.50 (s, 9H), 7.27 (m, 1H), 7.35 (m, 1H), 7.56 (d, J=7.6 Hz, 1H), 7.85 (bs, 1H), 9.99 (d, J=1.2 Hz, 1H). Mass spec.: 262.16 (MNa)⁺.

tert-Butyl 2-((1-benzylpiperidin-4-ylamino)methyl)-6-fluorophenylcarbamate

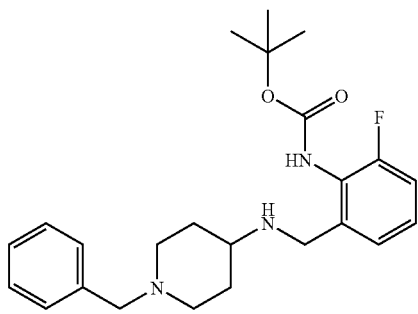

To a solution of tert-butyl 2-fluoro-6-formylphenylcarbamate (48.0 g, 201 mmol) in ethanol (100 mL) was added 4-amino-1-benzylpiperidine (41.0 mL, 201 mmol). The solution was concentrated in vacuo, and then water was removed by twice dissolving the residue in toluene and concentrating the solution in vacuo. The resulting oil was dissolved in tetrahydrofuran (250 mL), cooled to 0° C., and treated with sodium borohydride (3.80 g, 100 mmol). The ice bath was removed and stirring continued overnight. The reaction was treated with ethanol (250 mL), an additional portion of sodium borohydride (2.00 g, 53 mmol), and an additional portion of 4-amino-1-benzylpiperidine (2.0 mL, 9.8 mmol). The resulting solution was stirred for 4 h at room temperature. The reaction was cooled to 0° C., quenched by addition of saturated ammonium chloride, filtered to remove solids, and concentrated to remove most (but not all) of the tetrahydrofuran. The reaction was extracted with diethyl ether (2×). The ethereal layer was washed with water (3×), then brine, dried over magnesium sulfate, and concentrated to give 83 g (100%) as a viscous yellow oil which was pure enough to use in the following step. Mass spec.: 414.51 (MH)$^+$.

3-(1-Benzylpiperidin-4-yl)-8-fluoro-3,4-dihydroquinazolin-2(1H)-one

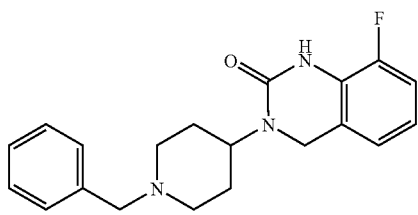

tert-Butyl 2-((1-benzylpiperidin-4-ylamino)methyl)-6-fluorophenylcarbamate (83.0 g, 201 mmol) was dissolved in pyridine (600 mL) and heated at reflux for 12 h. The reaction was concentrated, triturated with hot diethyl ether and placed in the freezer overnight. The resulting solid was filtered to give 68.1 g (64%) as a white solid. $^1$H-NMR (CDCl$_3$, 500 MHz) δ 1.68 (m, 2H), 1.86 (dddd, J=11.9, 11.9, 11.9, 3.4 Hz, 2H), 2.14 (dd, J=11.6, 10.1 Hz, 2H), 2.98 (d, J=11.6 Hz, 2H), 3.51 (s, 2H), 4.34-4.44 (m, 3H), 6.71 (bs, 1H), 6.79-6.89 (m, 2H), 6.94 (dd, J=9.2, 9.2 Hz, 1H), 7.21-7.34 (m, 5H). Mass spec.: 340.30 (MH)$^+$.

8-Fluoro-3-(piperidin-4-yl)-3,4-dihydroquinazolin-2(1H)-one

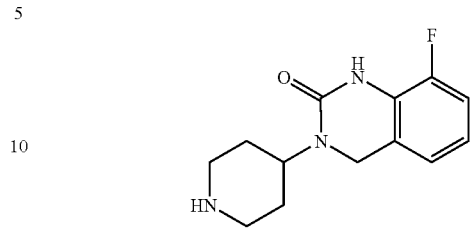

To a solution of 3-(1-benzylpiperidin-4-yl)-8-fluoro-3,4-dihydroquinazolin-2(1H)-one (2.50 g, 7.37 mmol) in acetic acid (50 mL) under nitrogen, was added palladium (10% on charcoal, 300 mg). The Parr shaker was pressurized to 50 psi and shaken for two days. The flask was flushed with nitrogen, filtered, and concentrated. The residue was dissolved in methanol and re-concentrated to give a light brown oil which solidified upon standing. The residue was dissolved in 1 N hydrochloric acid, and concentrated in vacuo, maintaining the temperature at 40° C. The resulting oil was dissolved in methanol, concentrated, and dried under high vacuum to give 2.19 g (quant.) of the hydrochloride salt as an off-white solid. Generation of the freebase: The hydrochloride salt (15.1 g, 52.8 mmol) was suspended in 2 N sodium hydroxide (40 mL) and stirred at room temperature for 2.5 h. The remaining solid was filtered, washed with water (0° C., 2×50 mL), then anhydrous diethyl ether (100 mL). The resulting solid was dried under high vacuum overnight to give 12.5 g (95%). $^1$H-NMR (CDCl$_3$, 500 MHz) δ 1.71 (m, 4H), 2.75 (m, 2H), 3.16 (m, 2H), 4.38 (s, 2H), 4.46 (m, 1H), 6.77 (bs, 1H), 6.81-6.89 (m, 2H), 6.95 (m, 1H). Mass spec.: 250.22 (MH)$^+$.

Methyl 2-(1-benzylpiperidin-4-yl)acetate

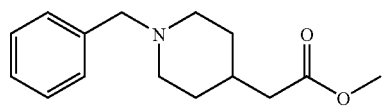

Sodium hydride (60% in mineral oil, 10.55 g, 264 mmol) was washed with hexanes then suspended in N,N-dimethylformamide (200 mL). Mixture was cooled to 0° C. Trimethyl phosphonoacetate (38.0 mL, 249 mmol) was added to the mixture dropwise. The reaction was stirred at 0° C. for 30 minutes. 1-Benzyl-4-piperidone (40.0 mL, 220 mmol) was added to the reaction mixture dropwise. The reaction was warmed to ambient temperature and held with stirring for 1 h. The reaction mixture was diluted with diethyl ether (500 mL), washed with water (2×), then brine. The organic layer was dried (magnesium sulfate), filtered, and concentrated in vacuo. The residue was dissolved in methanol (220 mL). Platinum(IV) oxide (600 mg, 2.64 mmol) was added to the mixture. The reaction vessel was placed on a Parr apparatus, charged with 40 psi of hydrogen gas, and shaken at room temperature for 5 h. The reaction mixture was removed from the apparatus, filtered through celite, and concentrated. The residue was passed through a short column of silica gel eluting with ethyl acetate. Fractions were concentrated in vacuo. The title compound was obtained as amber oil in 90% yield. $^1$H NMR (300 MHz, CDCl$_3$): δ 7.31-7.16 (m, 5H), 3.62 (s, 3H), 3.45 (s, 2H), 2.83 (d, J=11.71, 2H), 2.20 (d, J=6.95, 2H), 2.00-1.88 (m, 1H), 1.82-1.69 (m, 1H), 1.69-1.59 (m, 2H), 1.38-1.25 (m, 2H). Mass spec.: 249.3 (MH)+.

Methyl 2-(1-benzylpiperidin-4-yl)-3-hydroxy-3-(2-nitrophenyl)propanoate

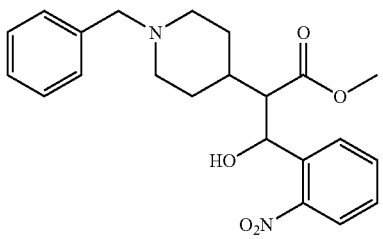

Diisopropylamine (3.50 mL, 24.9 mmol) was dissolved in tetrahydrofuran (30 mL). The mixture was cooled to −78° C. Butyllithium (2.5 M in pentane, 9.8 mL, 24.5 mmol) was added to the mixture dropwise, and the reaction stirred at −78° C. for 15 min. A solution of methyl 2-(1-benzylpiperidin-4-yl)acetate (5.50 g, 22.2 mmol) in THF (8 mL) was then added to the mixture dropwise over 20 minutes. The reaction was stirred at −78° C. for 45 minutes. A solution of 2-nitrobenzaldehyde (3.70 g, 24.5 mmol) in THF (5 mL) was then added to the mixture dropwise over 15 minutes. The reaction was stirred at −78° C. for 30 minutes and quenched by the addition of saturated aqueous ammonium chloride. The resulting mixture was warmed to room temperature, extracted with ethyl acetate (2×). The combined organics were dried (magnesium sulfate), filtered, and concentrated. Silica gel chromatography afforded the desired product in 89% yield as light yellow foam. Mass spec.: 399.3 (MH)+.

3-(1-Benzylpiperidin-4-yl)-4-hydroxy-3,4-dihydro-quinolin-2(1H)-one

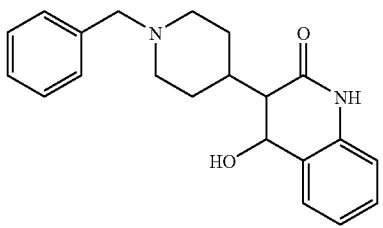

Methyl 2-(1-benzylpiperidin-4-yl)-3-hydroxy-3-(2-nitrophenyl)propanoate (950 mg, 2.4 mmol) was dissolved in acetic acid (20 mL). Iron(0) (1.0 g, 17.7 mmol) was added to the mixture. The reaction was heated at 85° C. and held with stirring for 1.5 h. The mixture was cooled to room temperature and diluted with water (30 mL). The liquid was decanted away from the solids. The aqueous solution was concentrated in vacuo. The residue was treated with ethyl acetate (50 mL). The mixture was made basic with aqueous sodium hydroxide. Celite was added to the resulting suspension to create a slurry which was in turn was filtered. The filtrate layers were separated. The aqueous layer was extracted with ethyl acetate. Combined organic layers were dried (magnesium sulfate), filtered, and concentrated in vacuo. The title compound was obtained without further purification as yellow oil in 69% yield. Mass spec.: 335.3 (MH)+.

3-(1-Benzylpiperidin-4-yl)quinolin-2(1H)-one

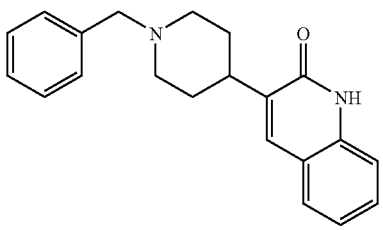

3-(1-Benzylpiperidin-4-yl)-4-hydroxy-3,4-dihydroquinolin-2(1H)-one (550 mg, 1.6 mmol) was suspended in benzene (10 mL). p-Toluenesulfonic acid monohydrate (370 mg, 1.9 mmol) was added to the mixture. The reaction was heated to reflux and held there for 1 h. The reaction mixture was concentrated in vacuo. The resulting residue was dissolved in 10% ethanol/dichloromethane (50 mL) and washed with aqueous sodium bicarbonate (2×). The organic layer was dried (magnesium sulfate), filtered, and concentrated in vacuo. The residue was triturated with diethyl ether to give a solid which was filtered, washed with diethyl ether, and dried in vacuo. The title compound was obtained as off-white solid in 63% yield. $^1$H NMR (300 MHz, DMSO-d$_6$): δ 11.72 (s, 1H), 7.72 (s, 1H), 7.62 (d, J=6.95, 1H), 7.47-7.38 (m, 1H), 7.35-7.30 (m, 4H), 7.29-7.20 (m, 2H), 7.14 (t, J=7.50, 1H), 3.49 (s, 3H), 2.92 (d, J=11.34, 2H), 2.83-2.69 (m, 1H), 2.04 (t, J=10.61, 2H), 1.78 (d, J=12.08, 2H), 1.71-1.47 (m, 2H). Mass spec.: 319.3 (MH)+.

3-(Piperidin-4-yl)quinolin-2(1H)-one

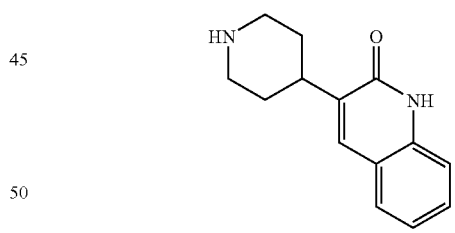

3-(1-Benzylpiperidin-4-yl)quinolin-2(1H)-one (1.72 g, 5.40 mmol) was suspended in methanol (70 mL). A catalytic amount of palladium hydroxide (20% on carbon) was added to the mixture. The reaction vessel was placed on a Parr apparatus and charged with 55 psi of hydrogen. The reaction was shaken at room temperature for 5 h. The mixture was removed from the apparatus and filtered. The filtrate was concentrated to give the title compound as white solid in 90% yield. $^1$H NMR (300 MHz, DMSO-d6): δ 7.65 (s, 1H), 7.64 (d, J=10.61, 1H), 7.41 (t, J=7.50, 1H), 7.26 (d, J=8.05, 1H), 7.13 (t, J=7.32, 1H), 3.02 (d, J=11.71, 2H), 2.82 (t, J=11.89, 2H), 2.58 (t, J=11.71, 2H), 1.73 (t, J=11.71, 2H), 1.42 (m, 2H). Mass spec.: 229.4 (MH)+.

N-(2-Bromo-6-fluorophenyl)pivalamide

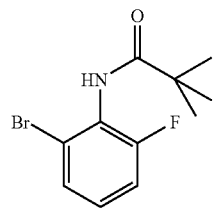

2-Bromo-6-fluoroaniline (8.2 g, 43.2 mmol) was dissolved in pyridine (10 mL) and treated with pivaloyl chloride (7.0 mL, 57.2 mmol). The reaction was stirred at room temperature for 3 h. The reaction mixture was concentrated in vacuo and treated with ethyl acetate (50 mL). Mixture was washed 1 N hydrochloric acid (2×), then brine. The organic layer was dried (magnesium sulfate), filtered, and concentrated in vacuo. The residue was triturated with hexanes to give a solid which was filtered, washed with hexanes, and dried in vacuo. The title compound was obtained as white solid in 76% yield. $^1$H NMR (300 MHz, CDCl$_3$): δ 7.39-7.31 (m, 1H), 7.14-7.03 (m, 2H), 6.98 (bs, 1H), 1.34 (s, 9H). Mass spec.: 274.1 (MH)$^+$, 276.1 (MNa)$^+$.

N-(2-Fluoro-6-formylphenyl)pivalamide

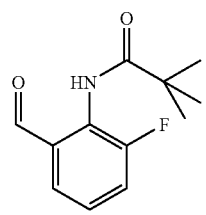

N-(2-Bromo-6-fluorophenyl)pivalamide (7.0 g, 25.5 mmol) was dissolved in tetrahydrofuran (200 mL). The mixture was cooled to −78° C., and treated with butyllithium (2 M in cyclohexane, 31.0 mL, 62.0 mmol) dropwise. The reaction mixture was held at −78° C. for 30 minutes. A solution of N,N-dimethylformamide (10.0 mL, 129 mmol) in tetrahydrofuran (30 mL) was added to the reaction mixture dropwise. The reaction was held at −78° C. for 30 minutes and quenched by the addition of aqueous ammonium chloride. The mixture was allowed to warm to room temperature and extracted with ethyl acetate (2×). The combined organic layers were dried (magnesium sulfate), filtered, and concentrated. Silica gel chromatography afforded the desired product as white solid in 80% yield. $^1$H NMR (300 MHz, CDCl$_3$): δ 9.93 (d, J=1.83, 1H), 9.14 (bs, 1H), 7.56-7.50 (m, 1H), 7.42-7.25 (m, 2H), 1.34 (s, 9H). Mass spec.: 224.2 (MH)$^+$.

tert-Butyl 4-(2-methoxy-2-oxoethyl)piperidine-1-carboxylate

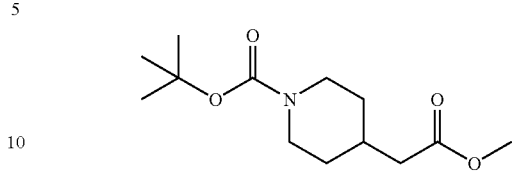

Sodium hydride (60% in mineral oil, 4.8 g, 120 mmol) was washed with hexanes and then suspended in N,N-dimethylformamide (100 mL). The mixture was cooled to 0° C. Trimethyl phosphonoacetate (17.0 mL, 111 mmol) was added to the mixture dropwise. The reaction was held at 0° C. for 45 minutes. A solution of N-tert-butoxycarbonyl-4-piperidone (18.5 g, 92.6 mmol) in N,N-dimethylformamide (25 mL) was added to the reaction mixture dropwise. The mixture was held at 0° C. for 1 h and then warmed to room temperature where it was held for 1 h. The reaction was quenched with 1 N hydrochloric acid. The mixture was extracted with diethyl ether (2×). Combined organic layers were washed with water (2×), then brine. The organic layer was dried (magnesium sulfate), filtered, and concentrated in vacuo. The residue was dissolved in 1:1 ethyl acetate/methanol (60 mL). A catalytic amount of palladium (10% on charcoal) was added to the mixture. The reaction vessel was placed on a Parr apparatus, charged with 55 psi of hydrogen, and shaken at room temperature for 18 h. The reaction mixture was removed from the Parr apparatus and filtered. The filtrate was concentrated in vacuo to give the title compound as lightly colored oil in 94% yield. $^1$H NMR (300 MHz, CDCl$_3$): δ 4.04 (d, J=10.25, 2H), 3.64 (s, 3H), 2.68 (t, J=14.44, 2H), 2.21 (d, J=6.95, 2H), 1.99-1.80 (m, 1H), 1.64 (d, J=13.54, 2H), 1.41 (s, 9H), 1.25-1.03 (m, 2H).

tert-Butyl 4-(1-(3-fluoro-2-pivalamidophenyl)-1-hydroxy-3-methoxy-3-oxopropan-2-yl)piperidine-1-carboxylate

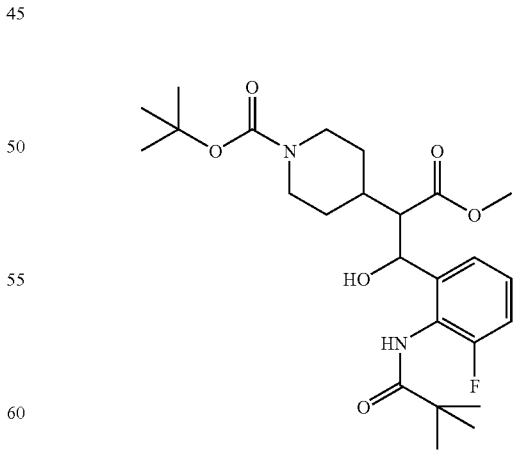

Diisopropylamine (3.40 mL, 24.2 mmol) was dissolved in tetrahydrofuran (70 mL). The mixture was cooled to −78° C. Butyllithium (2 M in cyclohexane, 12.2 µL, 24.4 mmol) was added dropwise to the reaction. The mixture was held at −78°

C. with stirring and held for 20 minutes. A solution of tert-butyl 4-(2-methoxy-2-oxoethyl)piperidine-1-carboxylate (5.20 g, 20.2 mmol) in tetrahydrofuran (15 mL) was added to the mixture dropwise. The mixture was held at −78° C. with stirring and held for 45 min. In a separate flask, sodium hydride (60% in mineral oil, 970 mg, 24.3 mmol) was washed with hexanes then suspended in tetrahydrofuran (50 mL). The mixture was cooled to 0° C. A solution of N-(2-Fluoro-6-formylphenyl)pivalamide (4.50 g, 20.2 mmol) in tetrahydrofuran (20 mL) was added to the mixture dropwise. The mixture was held at 0° C. with stirring and held for 1 h. The above prepared aldehyde mixture was added to the ester mixture dropwise over 1.25 h. The mixture was held at −78° C. with stirring and held for 1 h. The reaction was quenched with aqueous ammonium chloride, warmed to room temperature, and diluted with water. The mixture was extracted ethyl acetate (2×) and the aqueous phase was discarded. The material was dried (magnesium sulfate), filtered, and concentrated to dryness. Silica gel chromatography gave the title compound as white foam in 81% yield. Mass spec.: 381.2 $(M-C_4H_8O_2+H)^+$.

8-Fluoro-3-(piperidin-4-yl)quinolin-2(1H)-one hydrochloride

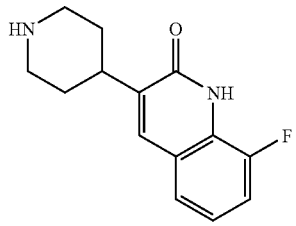

tert-Butyl 4-(1-(3-fluoro-2-pivalamidophenyl)-1-hydroxy-3-methoxy-3-oxopropan-2-yl)piperidine-1-carboxylate (7.86 g, 16.4 mmol) was dissolved in methanol (20 mL). Water (45 mL) was added to the mixture followed by concentrated hydrochloric acid (15 mL, 183 mmol). The reaction was heated to reflux and held for 2.5 h. The reaction mixture was concentrated in vacuo, redissolved in ethanol (50 mL), and concentrated in vacuo. The residue was crystallized from ethanol. The resulting solids were filtered, washed with cold ethanol, and dried in vacuo. The title compound was obtained as white solid in 83% yield. $^1$H NMR (500 MHz, DMSO-$d_6$): δ 11.85 (s, 1H), 8.98 (m, 1H), 8.85 (m, 1H), 7.75 (s, 1H), 7.54 (d, J=7.63, 1H), 7.36 (dd, J=0.22, 8.09, 1H), 7.21-7.11 (m, 1H), 3.41-3.29 (m, 2H), 3.14-2.94 (m, 3H), 2.02 (d, J=13.43, 2H), 1.88-1.71 (m, 2H). Mass spec.: 247.2 $(MH)^+$.

N-(1-Benzylpiperidin-4-yl)-4-fluoro-2-nitrobenzamide

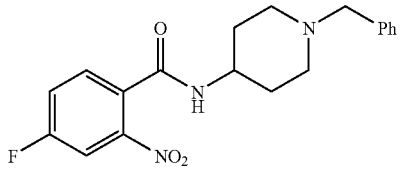

An oven dried flask was charged with 4-fluoro-2-nitrobenzoic acid (7.87 g, 42.5 mmol), 1-hydroxybenzotriazole (6.32 g, 46.8 mmol), 1-(3-dimethylaminopropyl)-3-ethylcarbodiimide (8.96 g, 46.7 mmol) and ethyl acetate (150 mL), followed by fast dropwise addition of triethylamine (11.8 mL, 84.7 mmol) at room temperature. The resulting white suspension was stirred for 3 h. The reaction was poured into 1:1 water/ethyl acetate (400 mL). After separation, the aqueous layer was extracted with ethyl acetate (200 mL). The combined organic layer was washed with brine (50 mL), dried over magnesium sulfate, and concentrated in vacuo to give a solid upon standing over night. Trituration and washing with ethyl acetate (2×6 mL) afforded the title compound as a light yellow solid (9.87 g, 71% yield). $^1$H-NMR (CDCl$_3$, 400 MHz) δ 7.74 (dd, J=6.4, 2.0, 1H), 7.50 (dd, J=6.8, 4.0, 1H), 7.43-7.22 (m, 6H), 5.71 (d, J=6.4, 1H), 4.05-3.93 (m, 1H), 3.50 (s, 2H), 2.85-2.79 (m, 2H), 2.20-2.14 (m, 2H), 2.05-2.02 (m, 2H), 1.58-1.49 (m, 2H). Mass spec.: 358.49 $(MH^+)$.

N-(2-amino-4-fluorobenzyl)-1-benzylpiperidin-4-amine

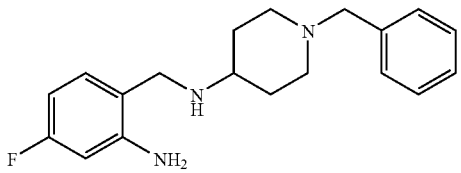

To a solution of lithium aluminum hydride (4.01 g, 105.7 mmol) in anhydrous 1,4-dioxane (40 mL) at reflux was added N-(1-benzylpiperidin-4-yl)-4-fluoro-2-nitrobenzamide (9.87 g, 30.2 mmol) in anhydrous 1,4-dioxane (125 mL) dropwise under nitrogen over 30 minutes. The resulting mixture was heated at reflux for 3 h under nitrogen. After cooling to room temperature, the reaction was carefully quenched with ice water (10 mL), sodium hydroxide (50% in water, 50 mL), and extracted with diethyl ether (2×500 mL). The combined organic layers were washed with brine (100 mL), dried over magnesium sulfate, and concentrated in vacuo to afford the title compound (8.64 g, 100% yield) as a yellow oil, which was pure enough for use in the next step. $^1$H-NMR (CD$_3$OD, 400 MHz) δ 7.52-7.40 (m, 5H), 7.28-7.18 (m, 1H), 6.53 (dd, J=11.2, 2.4, 1H), 6.48-6.38 (m, 1H), 4.33 (s, 2H), 4.18 (s, 2H), 3.68-3.46 (m, 3H), 3.25-3.10 (m, 2H), 2.50-2.42 (m, 2H), 2.16-1.93 (m, 2H). Mass spec.: 314.21 $(MH^+)$.

3-(1-Benzylpiperidin-4-yl)-7-fluoro-3,4-dihydroquinazolin-2(1H)-one

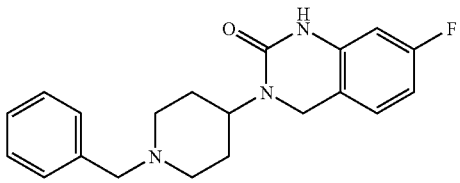

1,1'-Carbonyldiimidazole (6.92 g, 42.7 mmol) was added to a solution of N-(2-amino-4-fluorobenzyl)-1-benzylpiperidin-4-amine (8.64 g, 30.2 mmol) in dry tetrahydrofuran (150 mL) at 0° C. in one portion. After 5 min, the mixture was allowed to warm to room temperature and stirred for 3 h. The reaction was partitioned between water/diethyl ether (200 mL/200 mL). After separation, the aqueous solution was extracted with diethyl ether (200 mL). The combined organic solution was washed with brine (100 mL), dried over magnesium sulfate, and concentrated in vacuo to afford a light yellow solid which was triturated with diethyl ether (3×10 mL) to give the title compound as a white solid (3.41 g, 36% yield). $^1$H-NMR (CDCl$_3$, 400 MHz) δ 7.40-7.18 (m, 5H), 6.92-6.82 (m, 1H), 6.75 (dd, J=8.2, 2.6, 1H), 6.66 (dd, J=8.8, 4.8, 1H), 4.48-4.34 (m, 1H), 4.03 (s, 2H), 3.53 (s, 2H), 2.98 (d, J=11.2, 2H), 2.37-2.12 (m, 2H), 1.99-1.82 (m, 2H), 1.67 (d, J=11.2, 2H); Mass spec.: 340.03 (MH+).

7-Fluoro-3-(piperidin-4-yl)-3,4-dihydroquinazolin-2(1H)-one

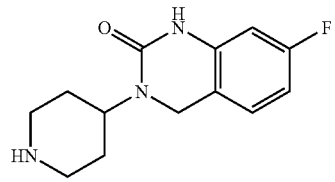

3-(1-Benzylpiperidin-4-yl)-7-fluoro-3,4-dihydroquinazolin-2(1H)-one (1.32 g, 3.89 mmol) was dissolved in ethanol (100 mL) at room temperature. To this was added palladium (10% on charcoal, 130 mg). The resulting mixture was stirred under a hydrogen balloon for 4 d. The reaction was filtered through a pad of celite, eluting with ethanol (50 mL), and concentrated in vacuo to afford a yellow residue. Upon addition of diethyl ether (20 mL), a solid precipitated from solution. Trituration and filtration with diethyl ether (2×5 mL) gave the title compound as a yellow solid (0.842 g, 87% yield). $^1$H-NMR (CD$_3$OD, 400 MHz) δ 6.94-6.88 (m, 2H), 6.78 (dd, J=6.2, 4.0, 1H), 4.42 (s, 2H), 4.41-4.35 (m, 1H), 3.53-3.47 (m, 2H), 3.21-3.13 (m, 2H), 2.25-2.14 (m, 2H), 1.98-1.92 (m, 2H). Mass spec.: 250.10 (MH+).

Furthermore, the following are also prophetically envisaged as compounds of the present invention (represented by structure):

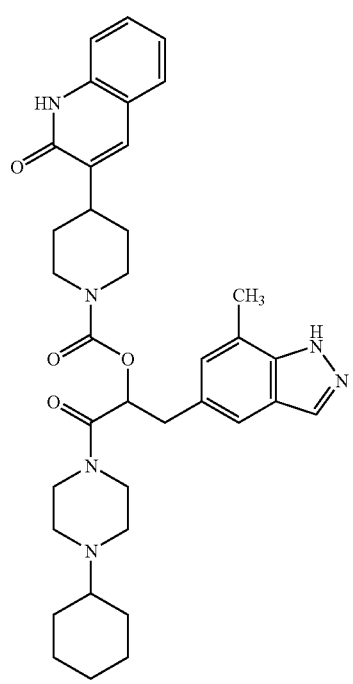

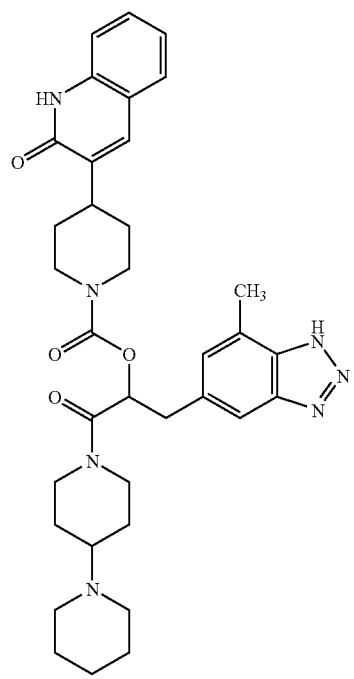

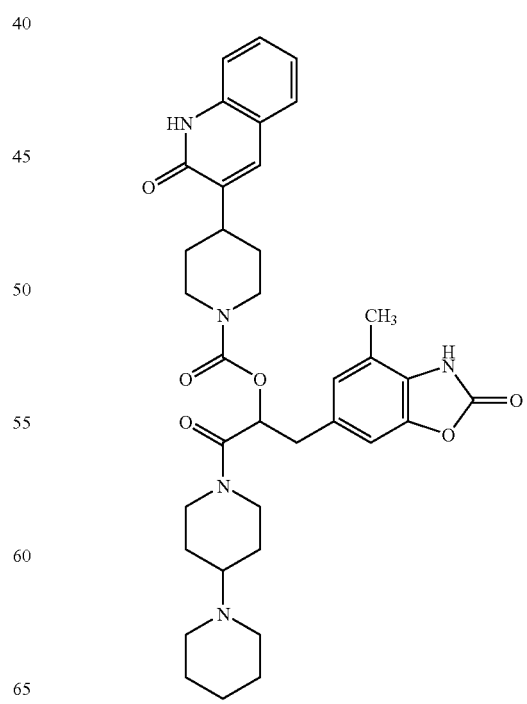

87
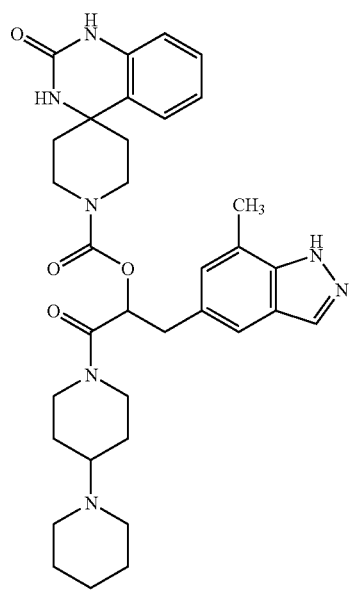
88
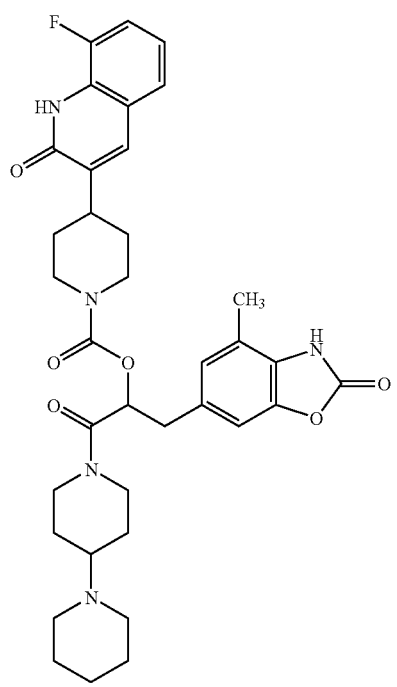
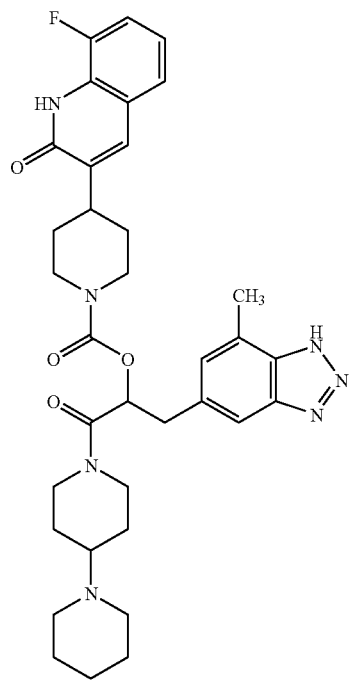
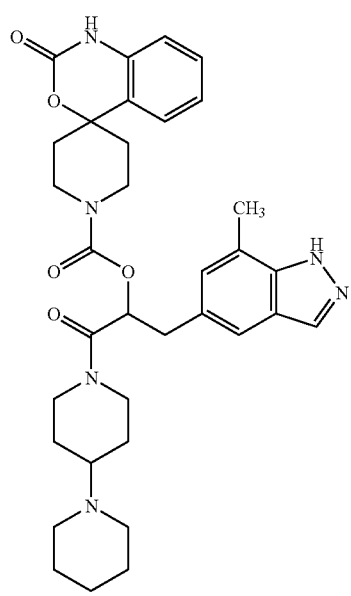

89
-continued
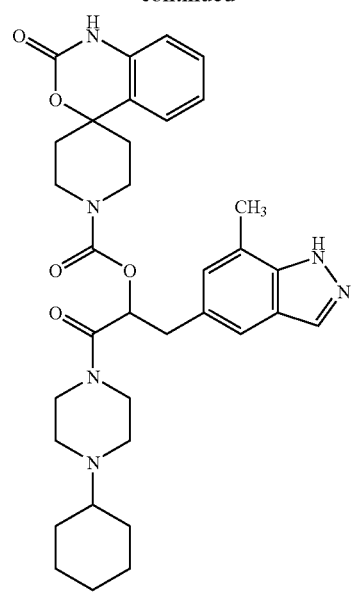
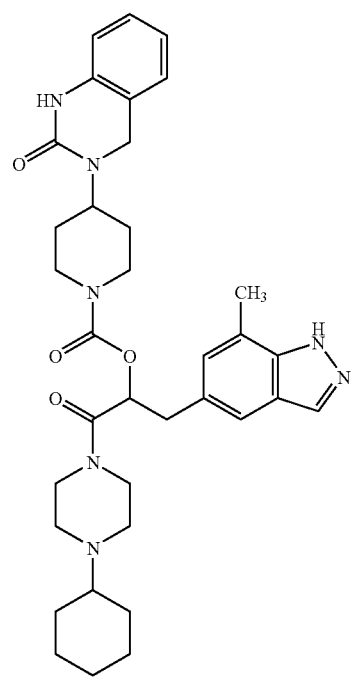
90
-continued
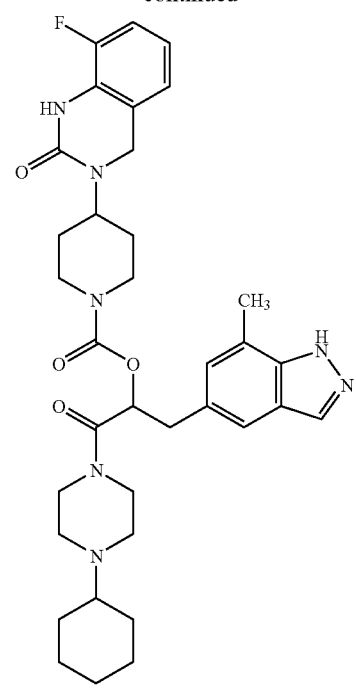
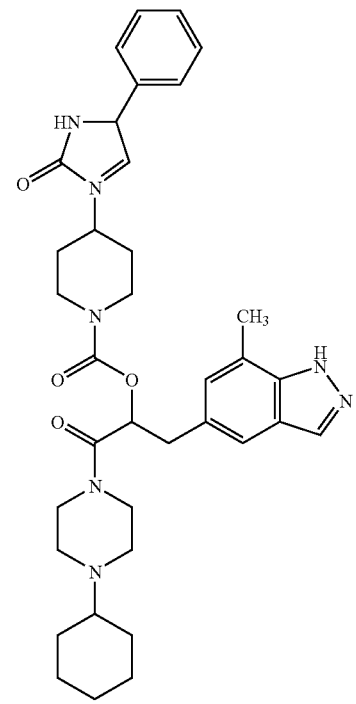

91
-continued
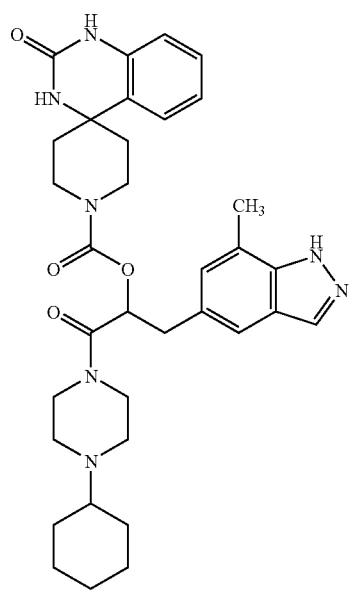
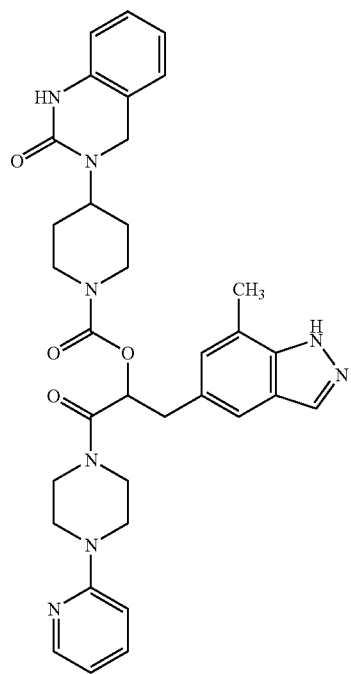
92
-continued
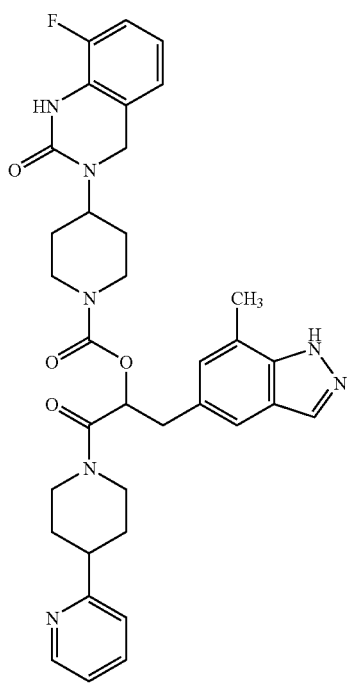
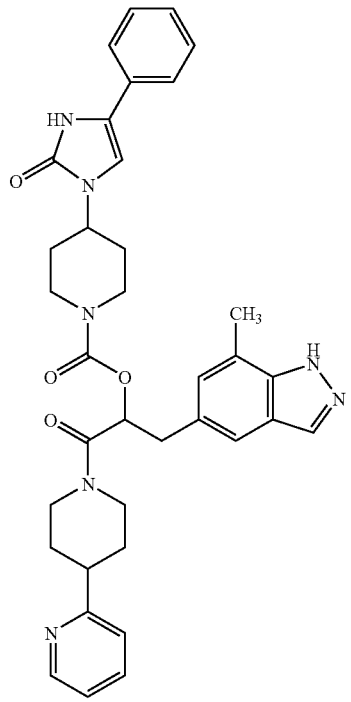

-continued
93
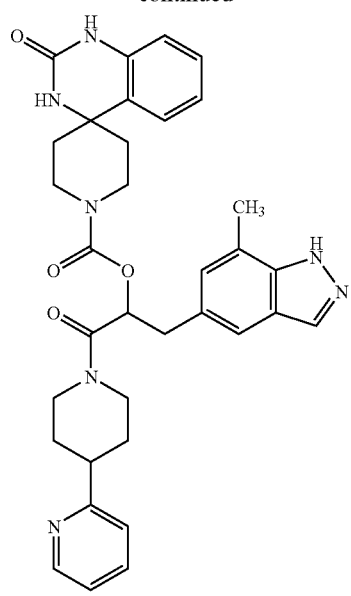
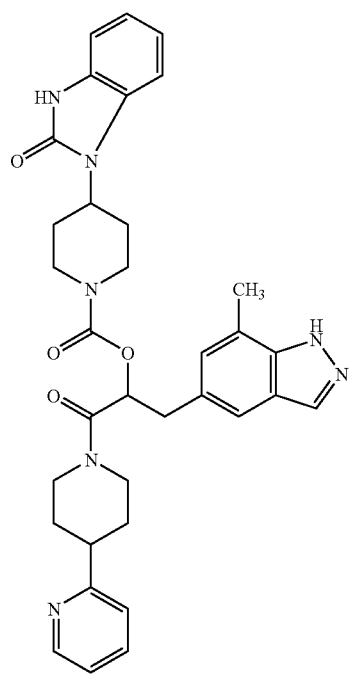
94
-continued
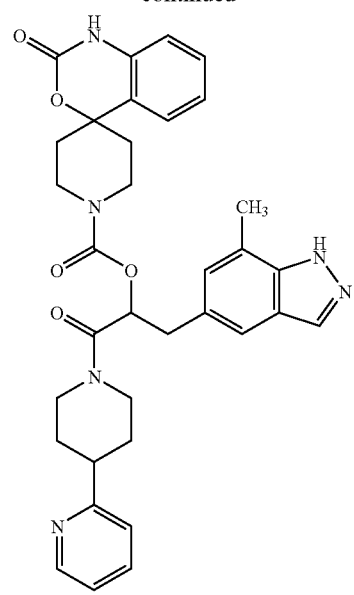
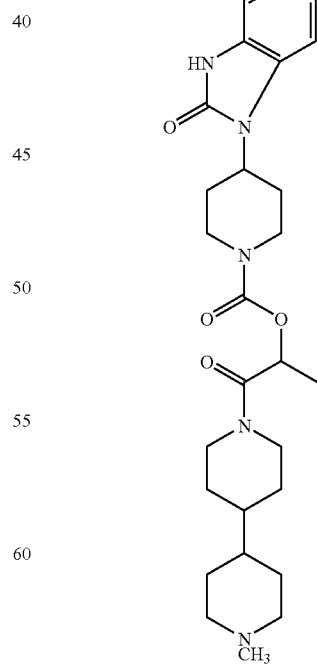

95
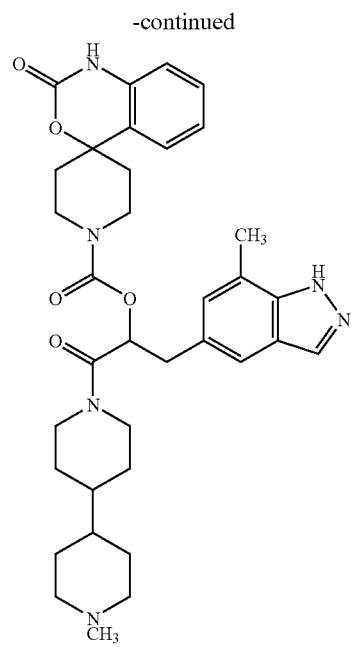
96
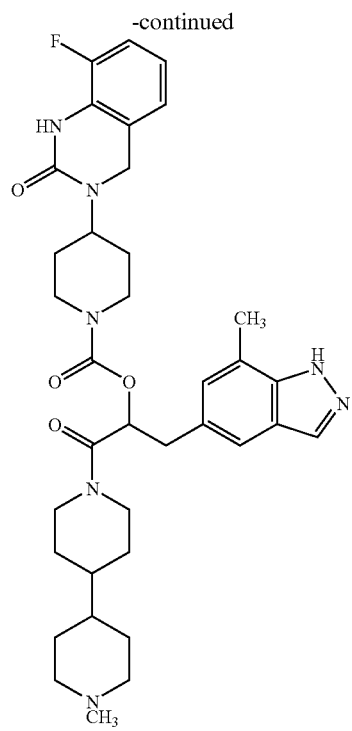
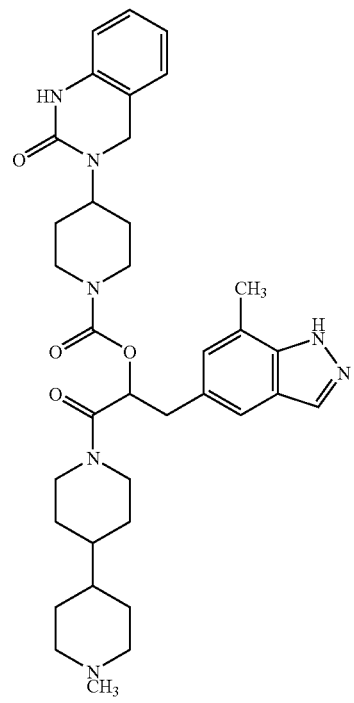
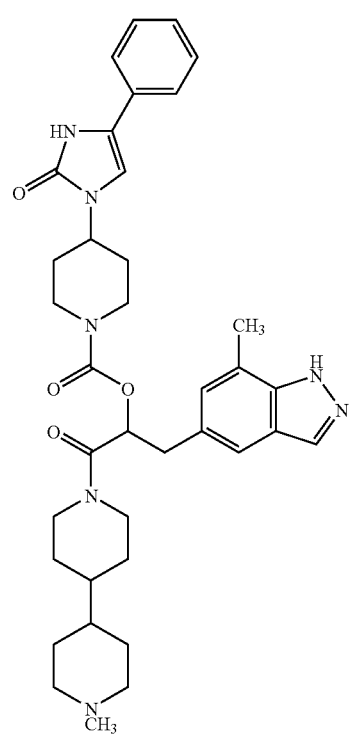

97
-continued
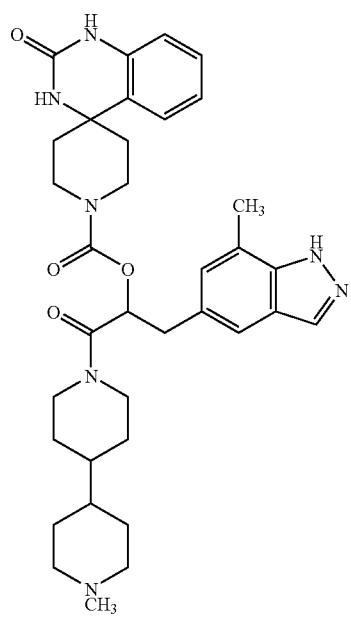
98
-continued
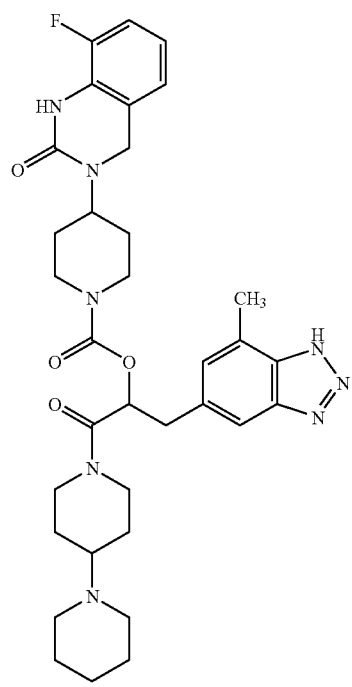
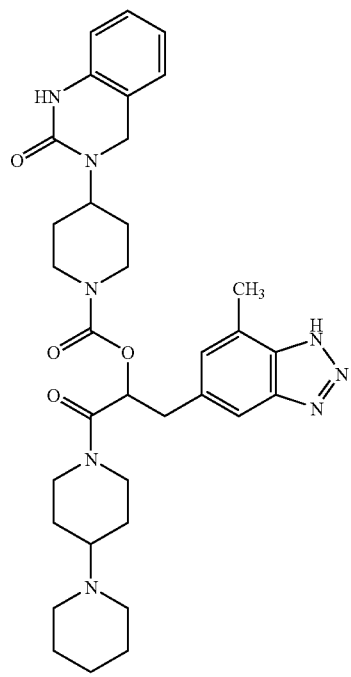

99
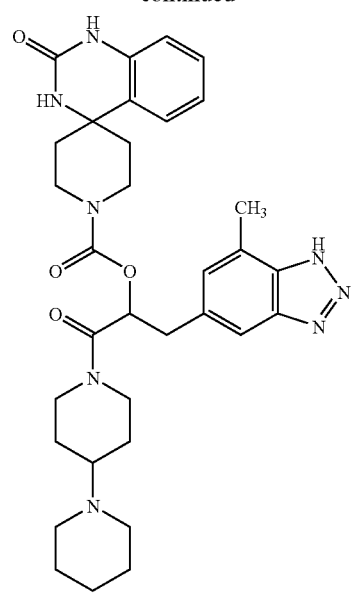
100
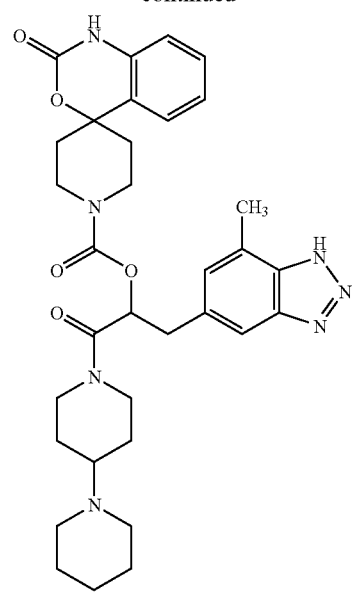
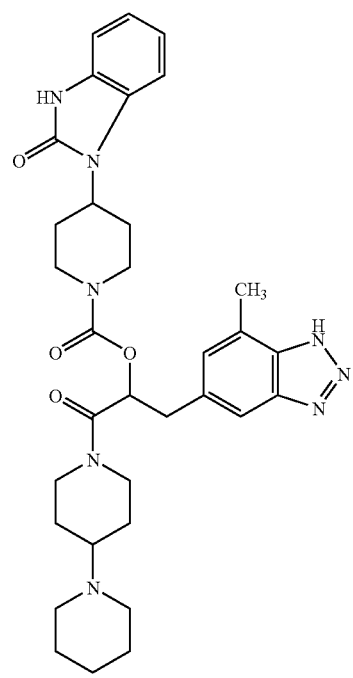
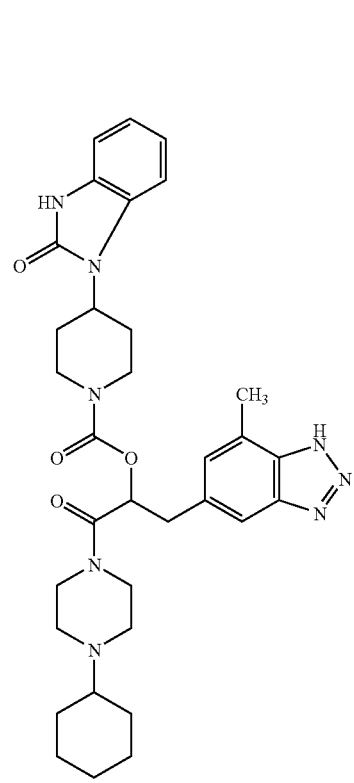

101
-continued
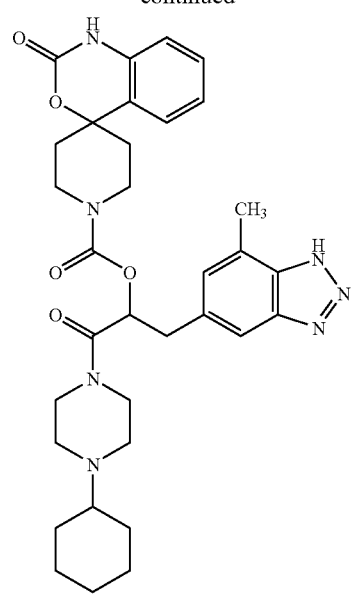
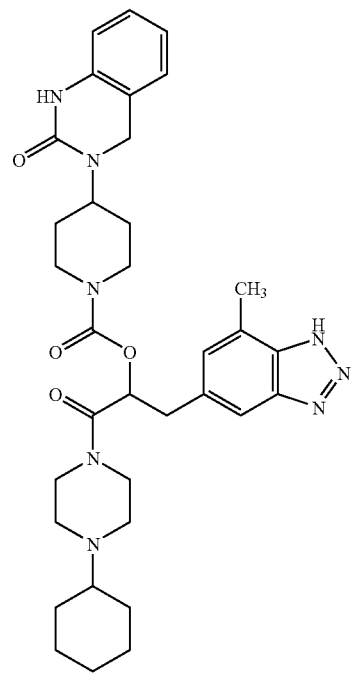
102
-continued
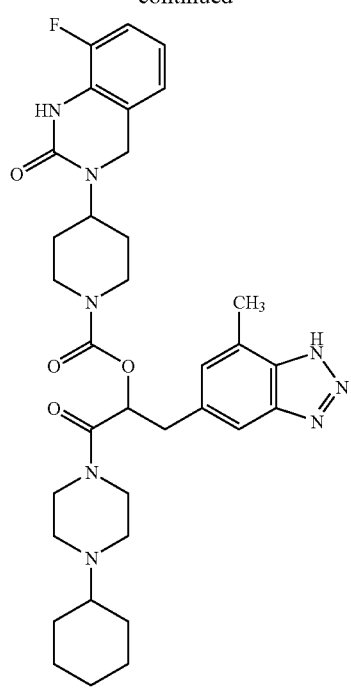
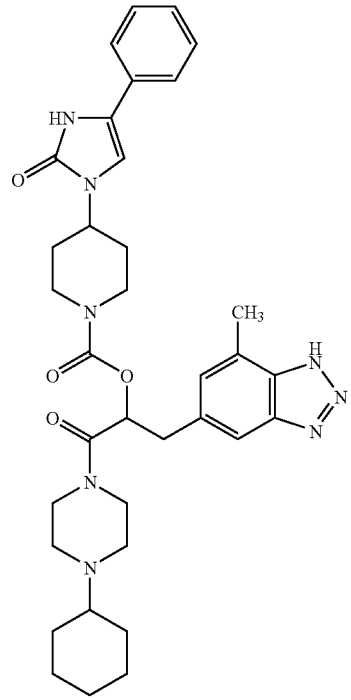

103
-continued
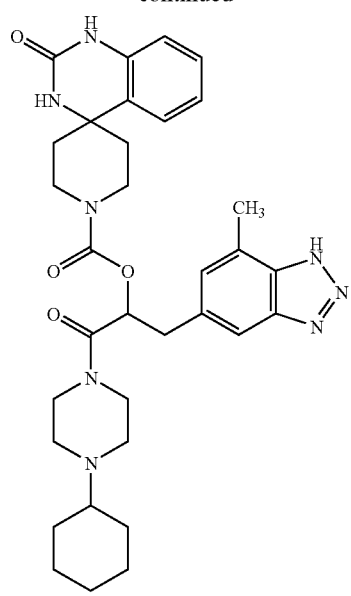
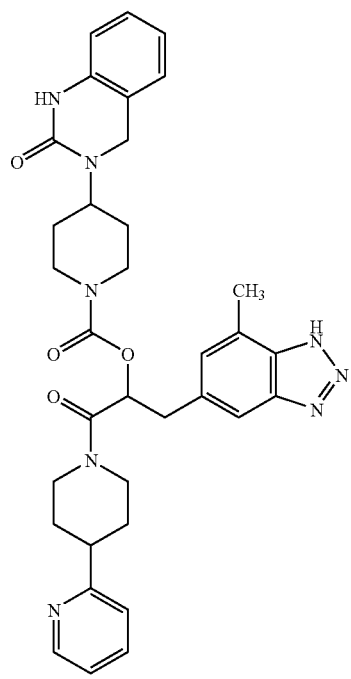
104
-continued
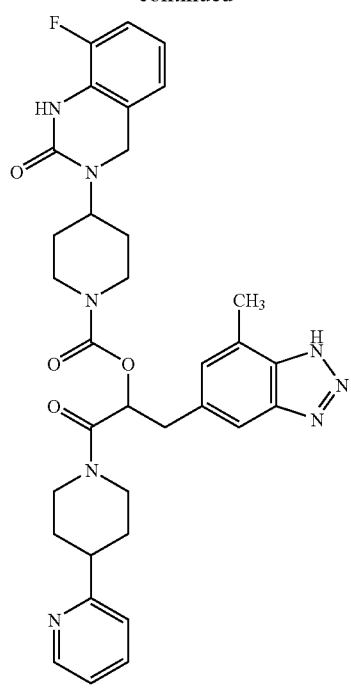
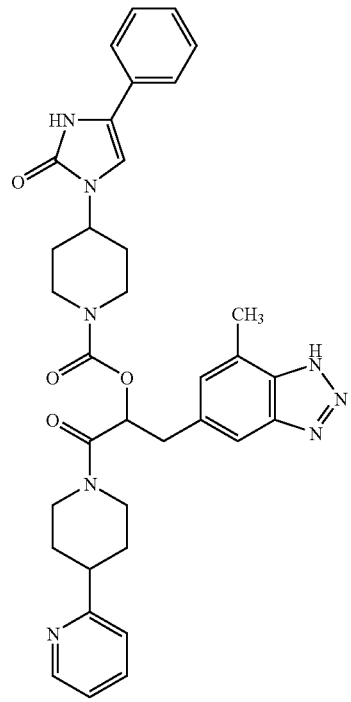

105
-continued
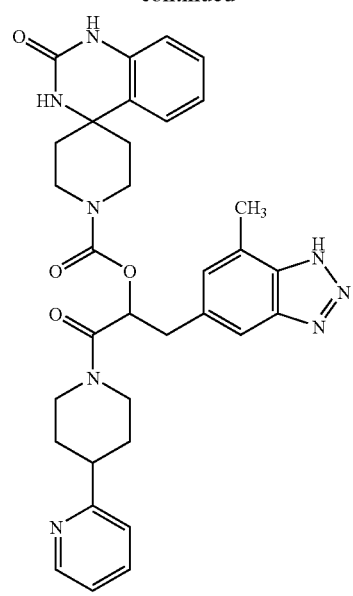
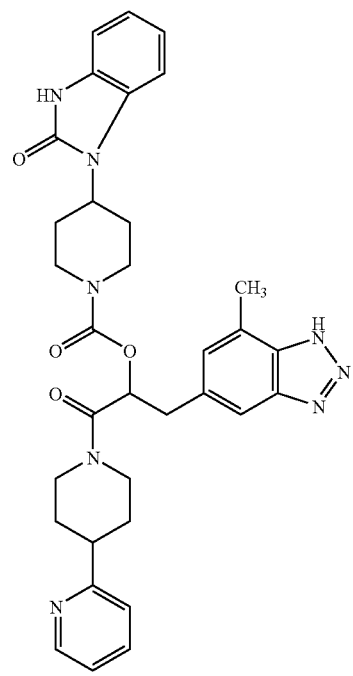
106
-continued
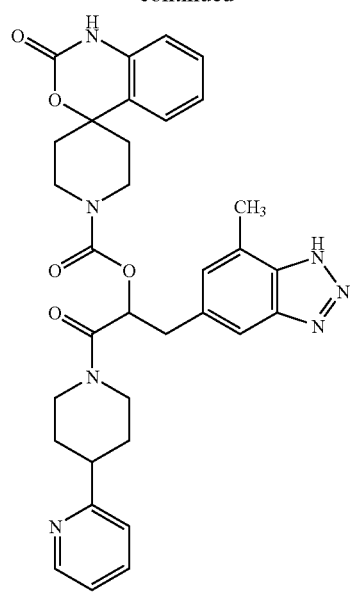
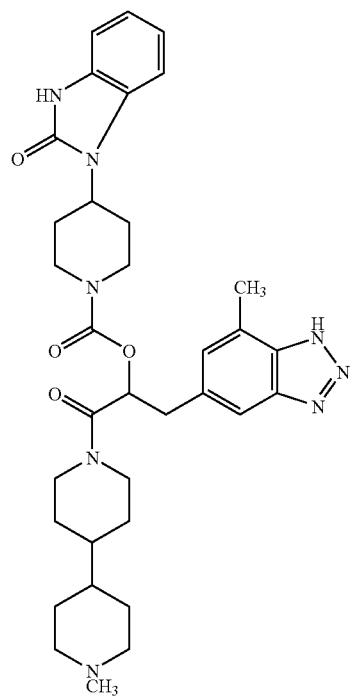

107
-continued
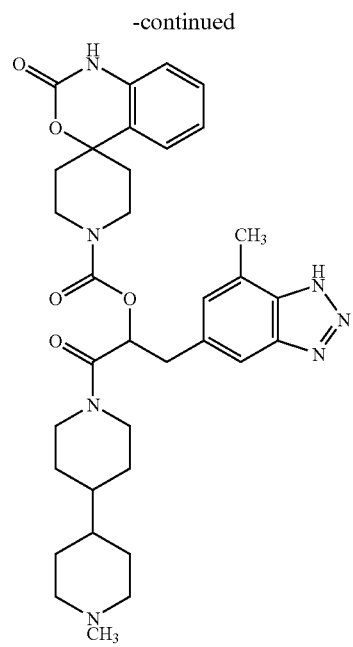
108
-continued
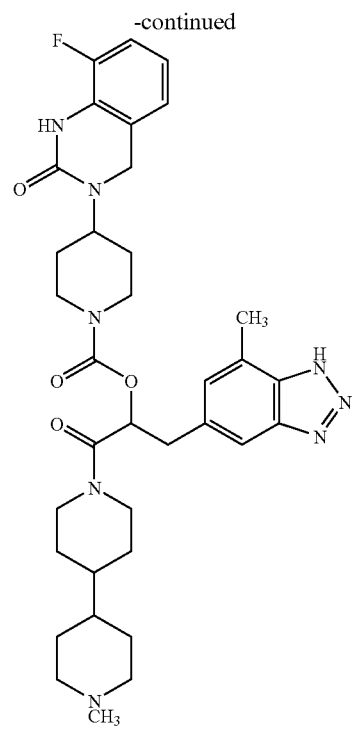
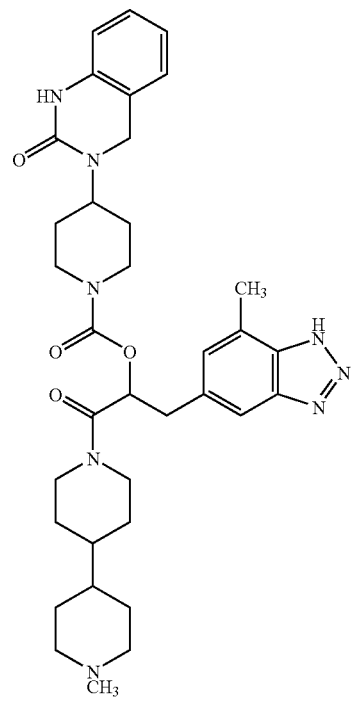
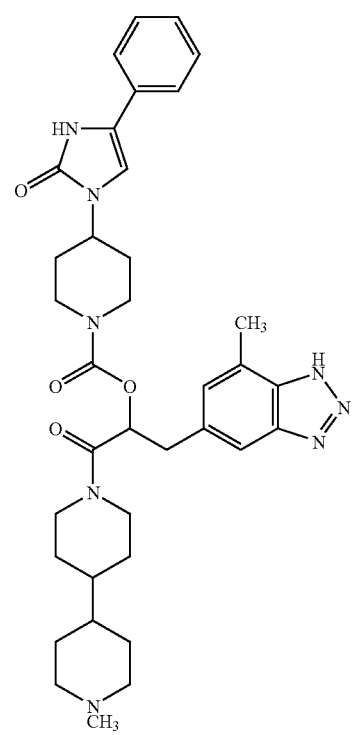

109
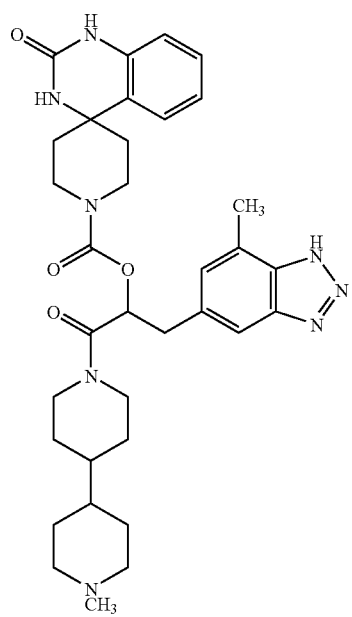
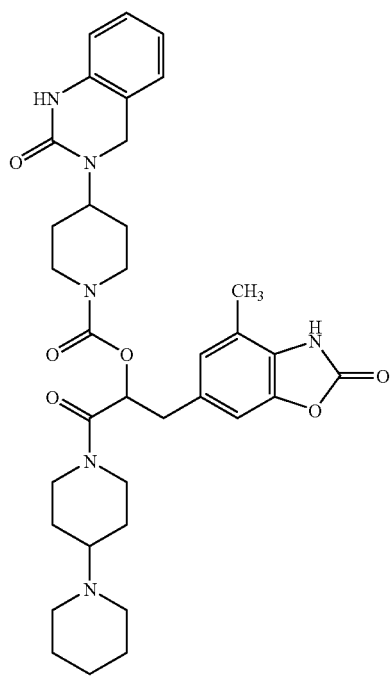
110
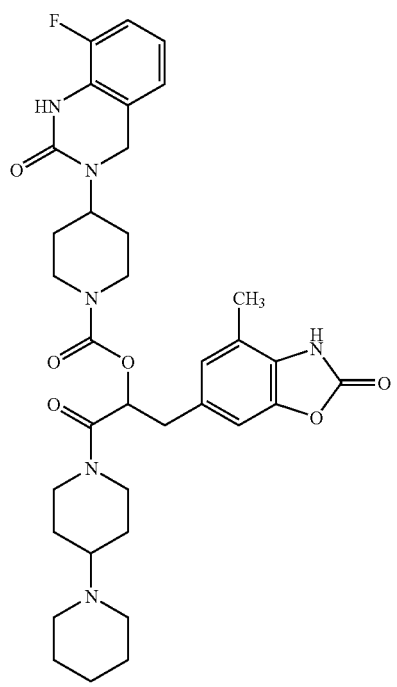
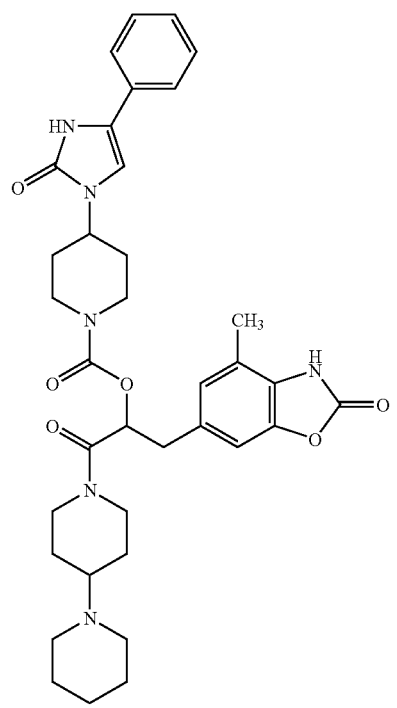

111
-continued
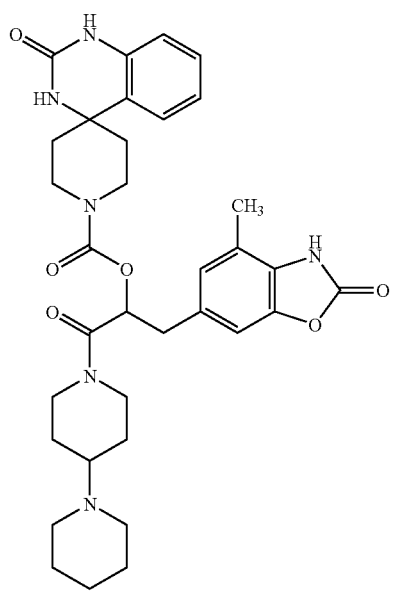
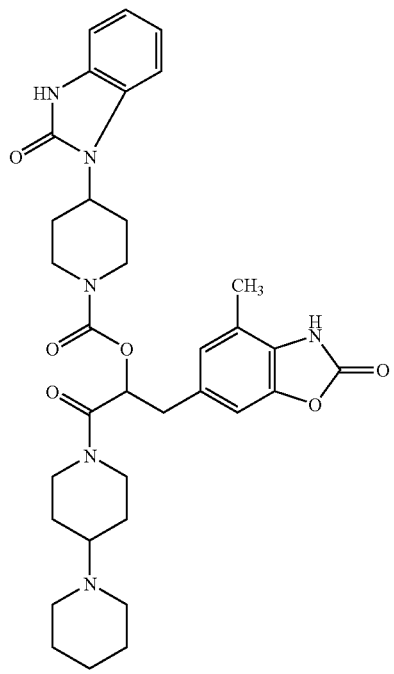
112
-continued
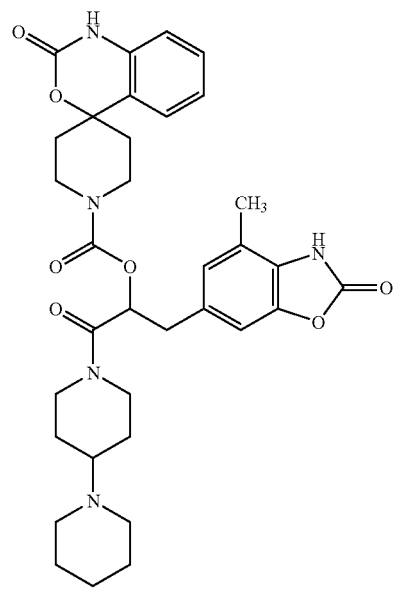
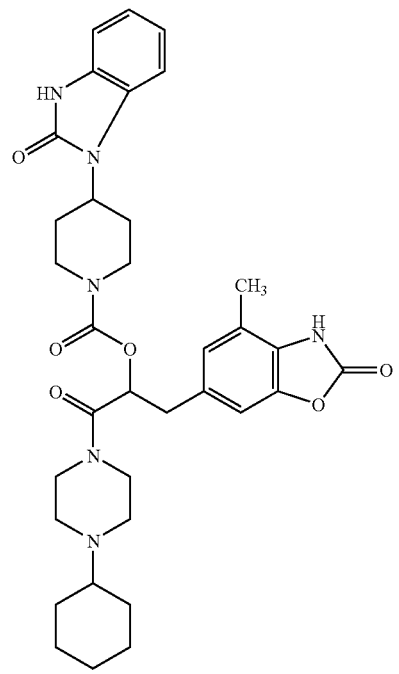

113
-continued
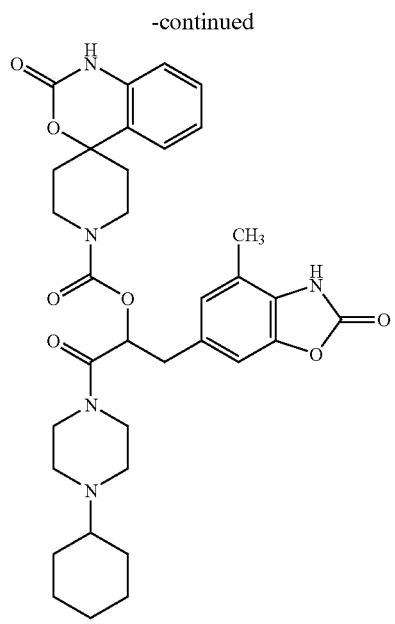
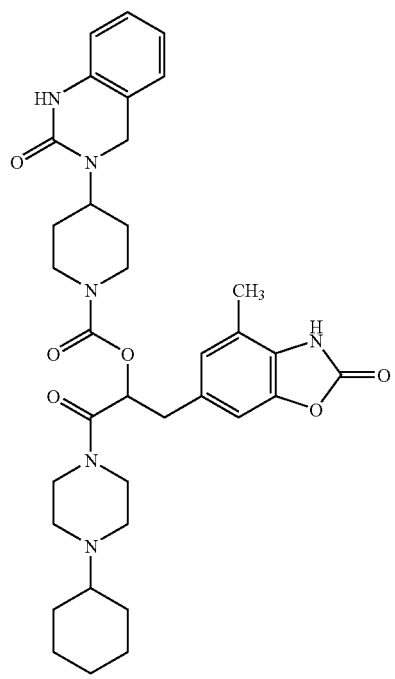
114
-continued
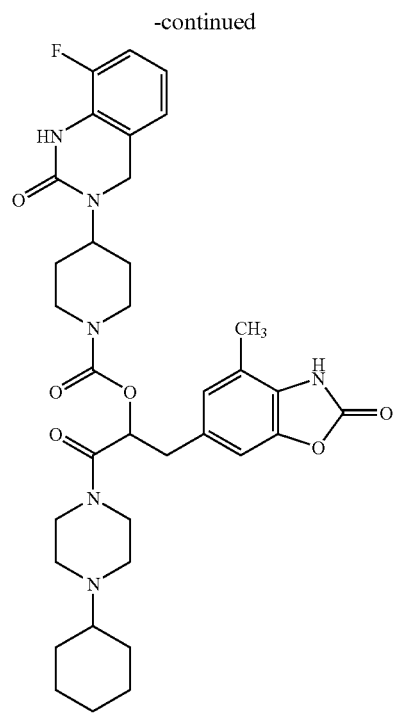
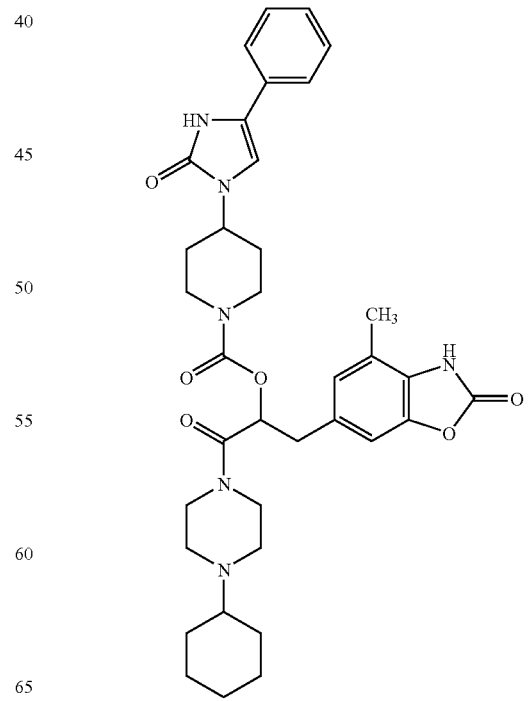

115
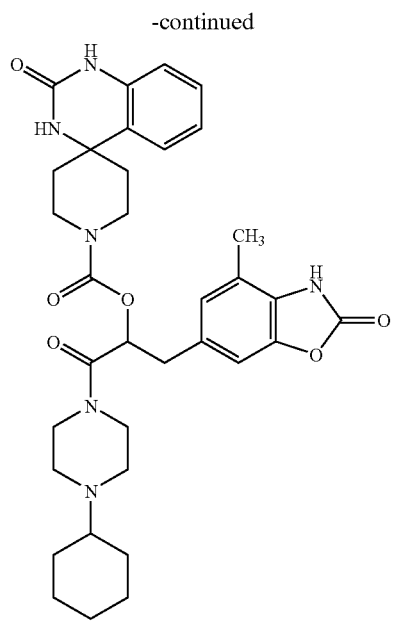
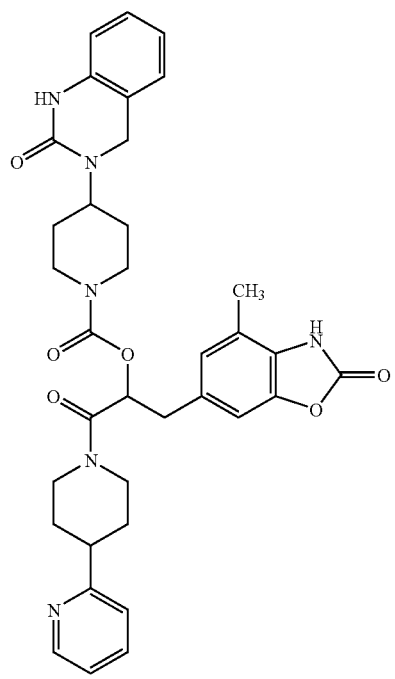
116
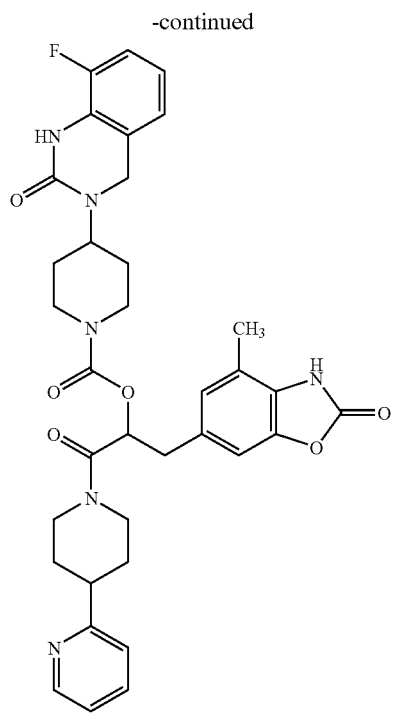
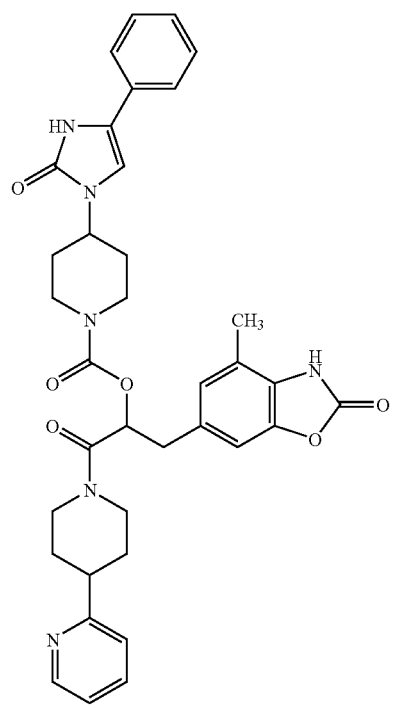

117
-continued
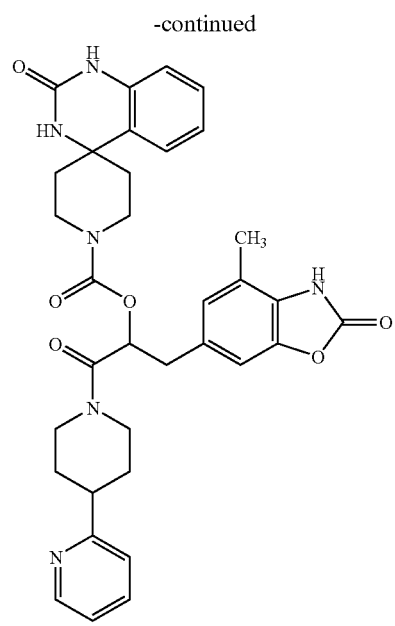
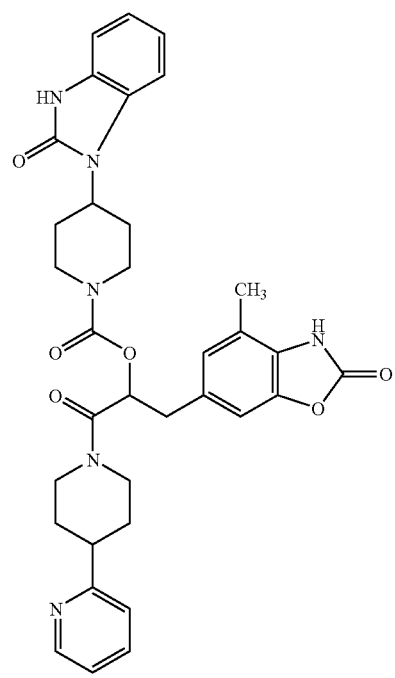
118
-continued
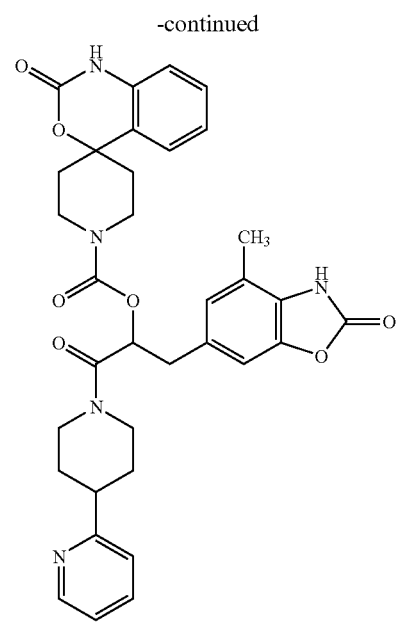
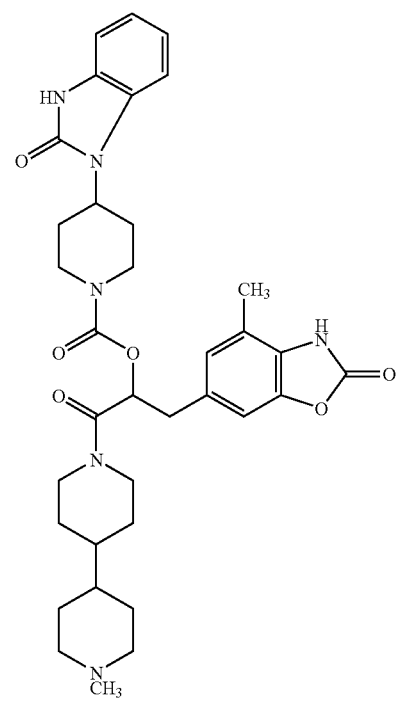

119
-continued
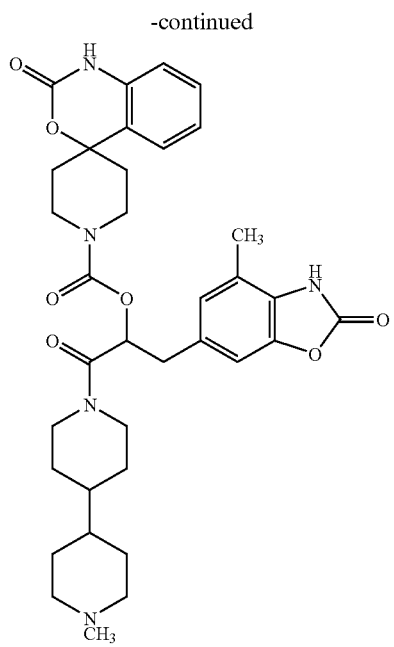
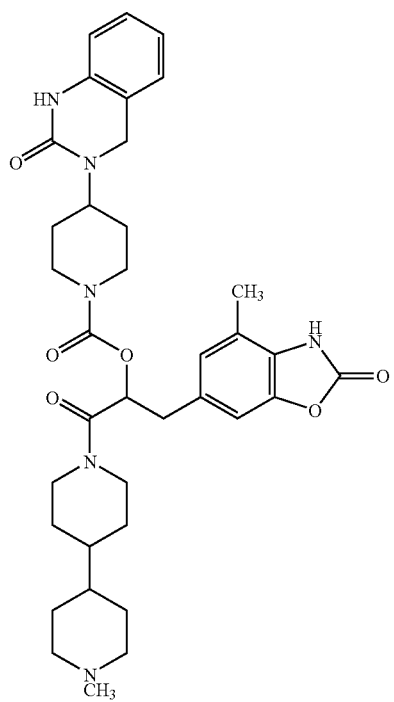
120
-continued
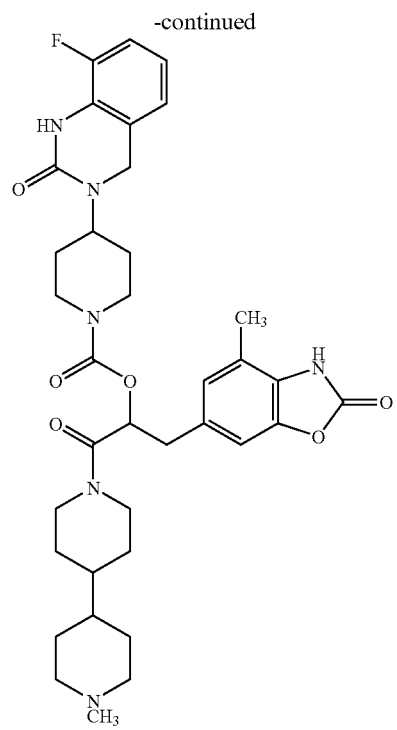
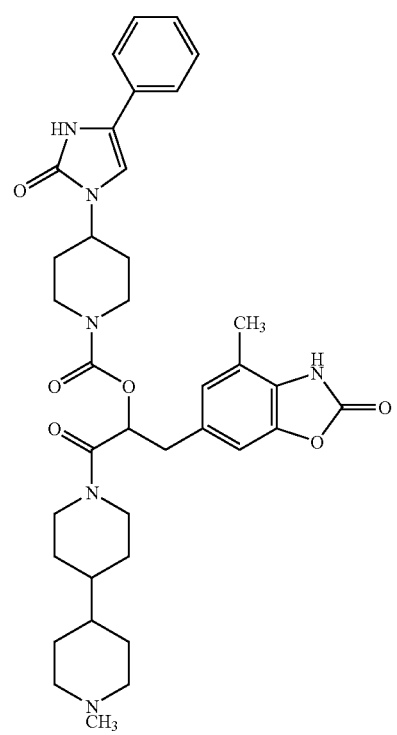

121
-continued
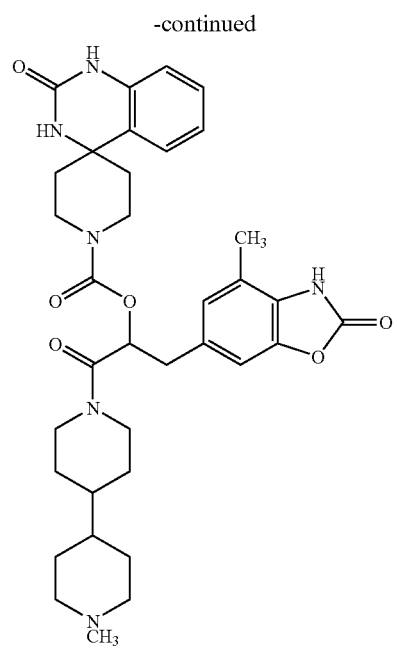
122
-continued
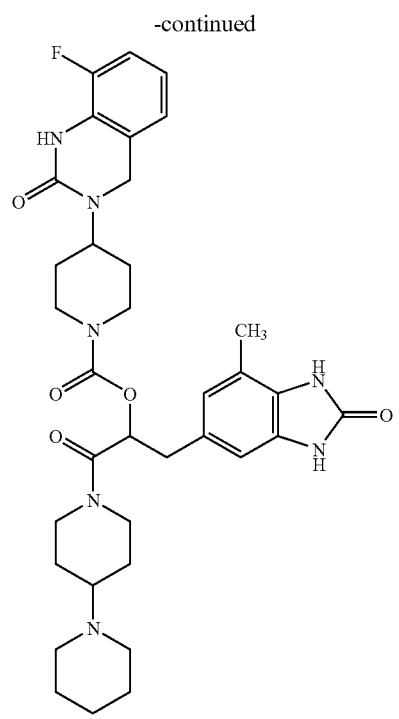
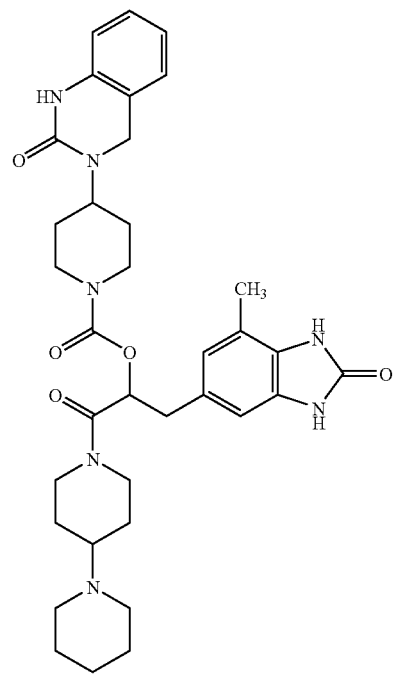
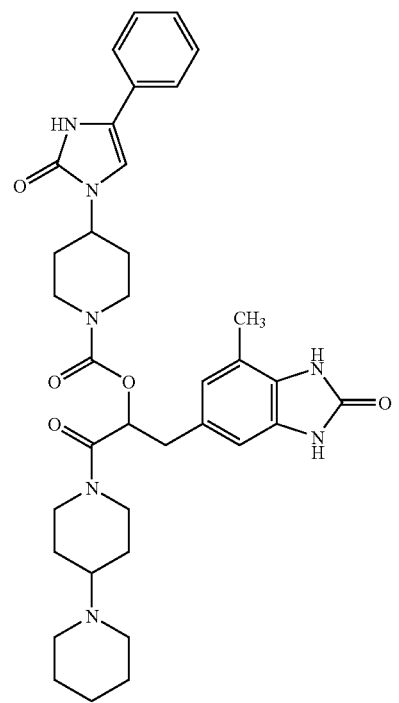

123
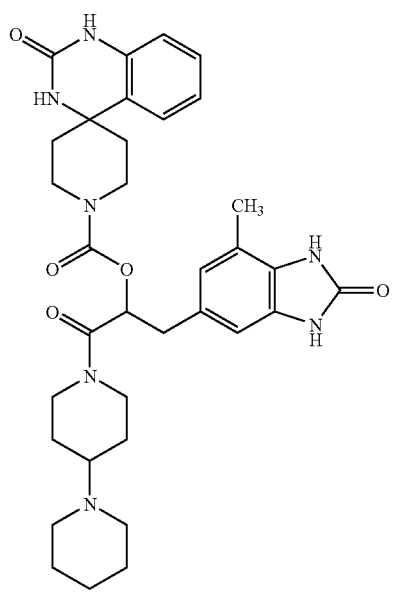
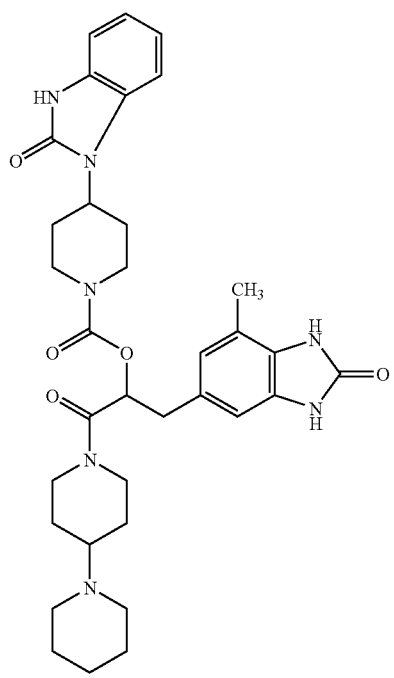
124
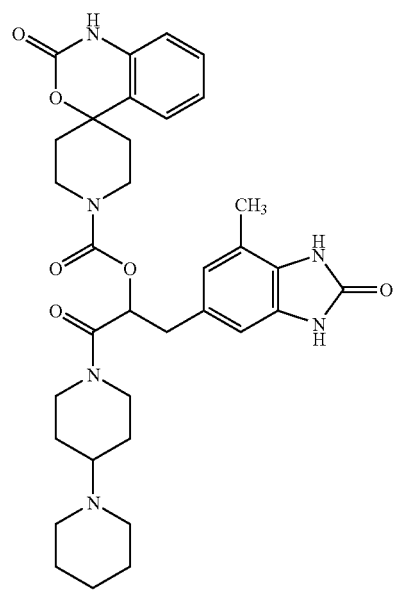
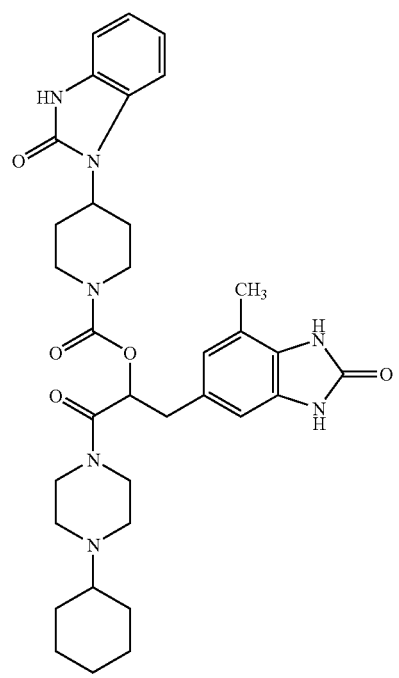

125
-continued
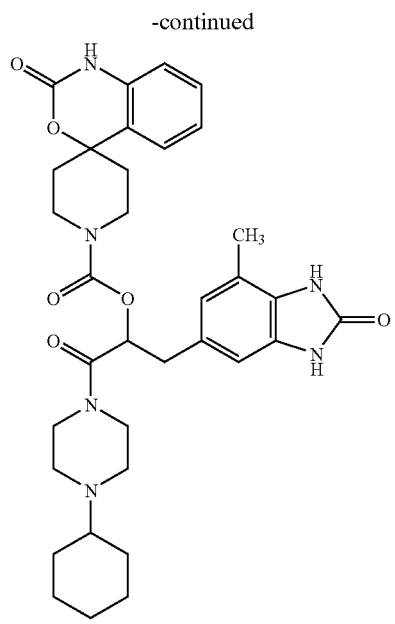
126
-continued
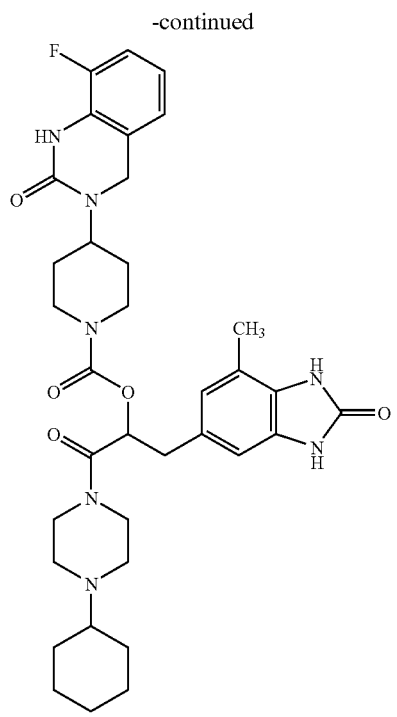
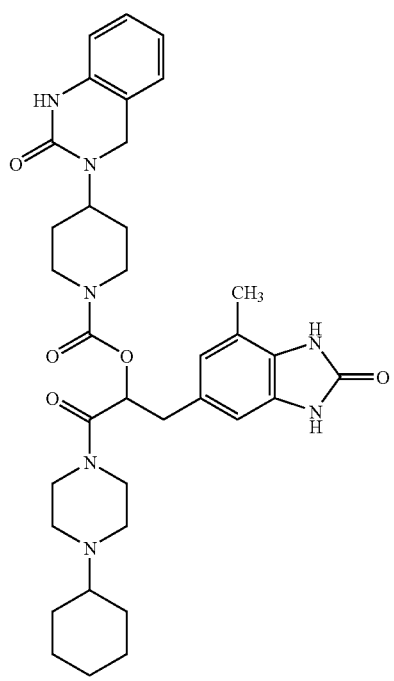
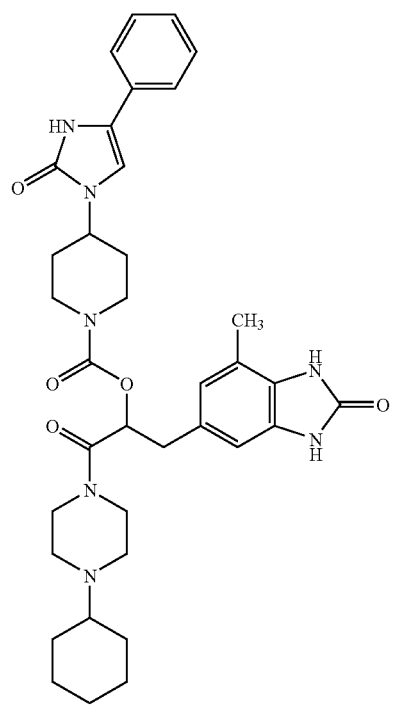

127
-continued
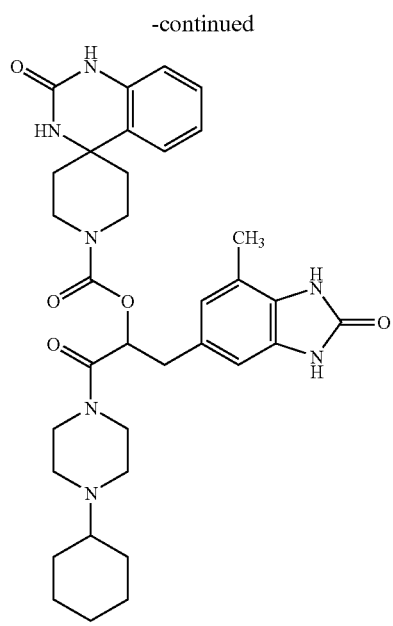
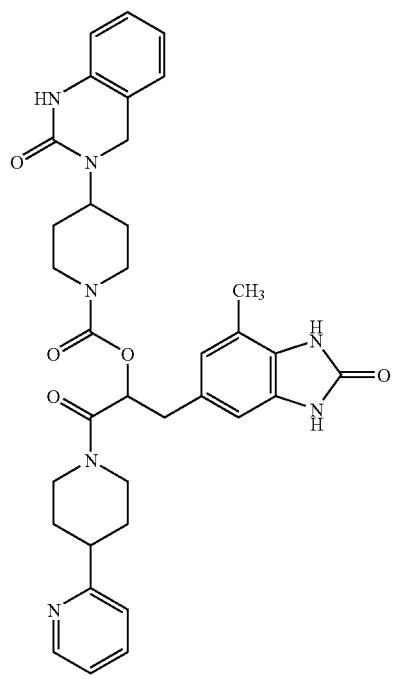
128
-continued
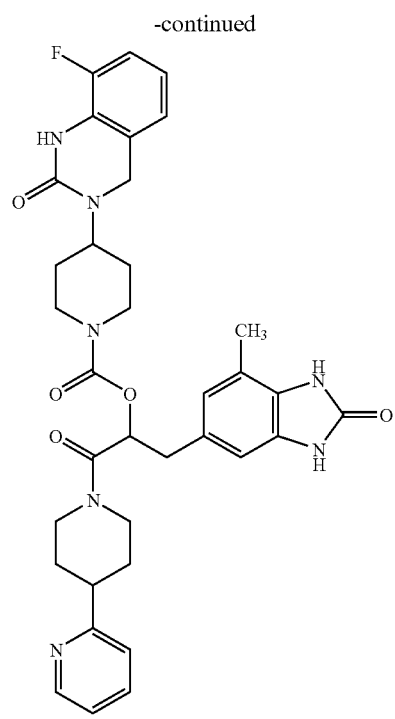
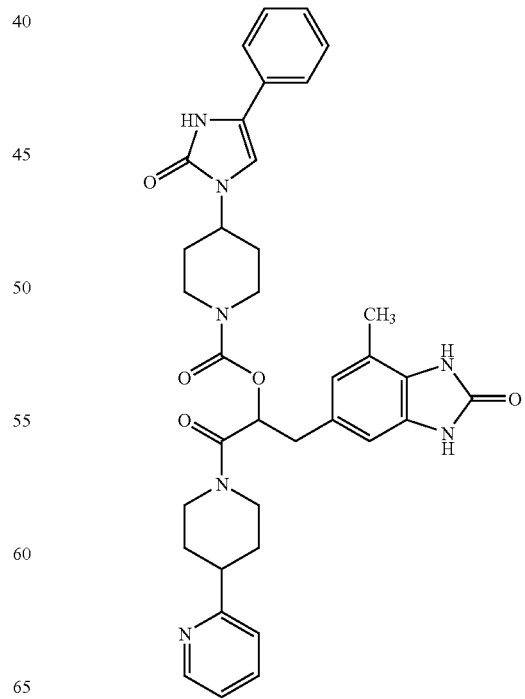

129
-continued
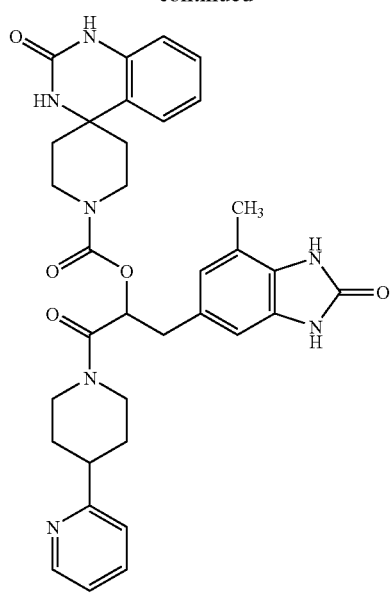
130
-continued
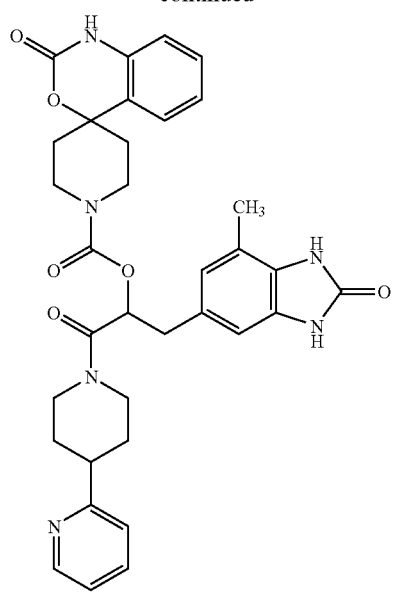
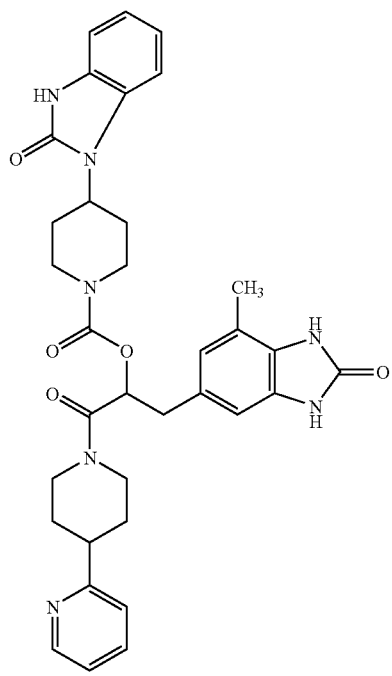

131
-continued
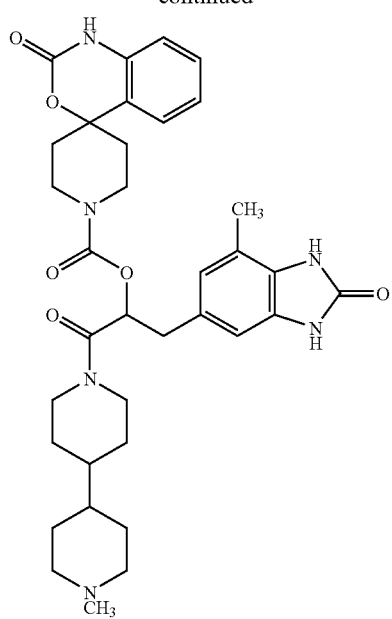
132
-continued
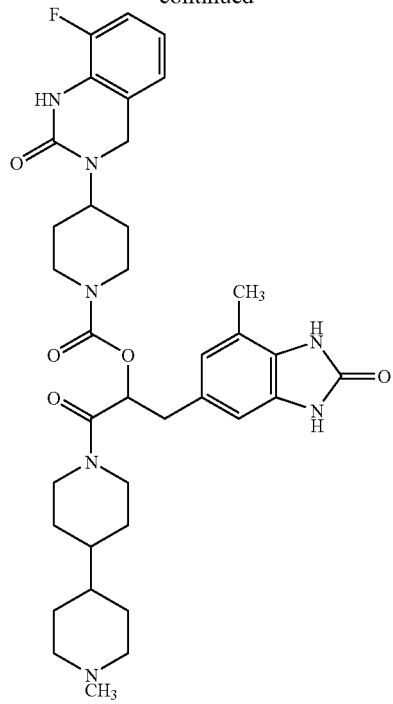

-continued

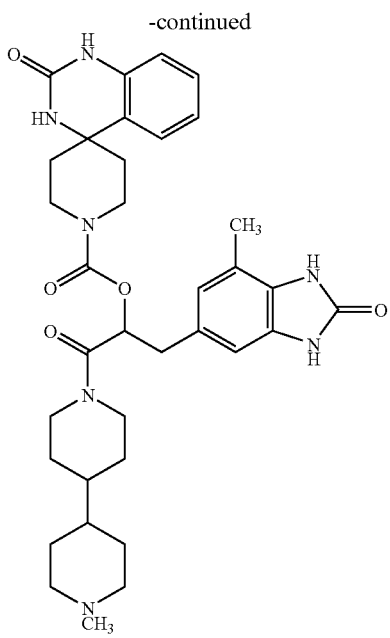

CGRP Binding Assay

Tissue Culture. SK—N-MC cells were grown at 37° C. in 5% $CO_2$ as a monolayer in medium consisting of MEM with Earle's salts and L-glutamine (Gibco) supplemented with 10% fetal bovine serum (Gibco).

Cell Pellets. The cells were rinsed twice with phosphate-buffered saline (155 mM NaCl, 3.3 mM $Na_2HPO_4$, 1.1 mM $KH_2PO_4$, pH 7.4), and incubated for 5-10 min. at 4° C. in hypotonic lysis buffer consisting of 10 mM Tris (pH 7.4) and 5 mM EDTA. The cells were transferred from plates to polypropylene tubes (16×100 mm) and homogenized using a polytron. Homogenates were centrifuged at 32,000×g for 30 min. The pellets were resuspended in cold hypotonic lysis buffer with 0.1% mammalian protease inhibitor cocktail (Sigma) and assayed for protein concentration. The SK—N-MC homogenate was then aliquoted and stored at −80° C. until needed.

Radioligand Binding Assay. The compounds of invention were solubilized and carried through serial dilutions using 100% DMSO. Aliquots from the compound serial dilutions were further diluted 25 fold into assay buffer (50 mM Tris-Cl pH 7.5, 5 mM $MgCl_2$, 0.005% Triton X-100) and transferred (volume 50 µl) into 96 well assay plates. [$^{125}$I]-CGRP (Amersham Biosciences) was diluted to 60 µM in assay buffer and a volume of 50 µl was added to each well. SK—N-MC pellets were thawed, diluted in assay buffer with fresh 0.1% mammalian protease inhibitor cocktail (Sigma), and homogenized again. SK—N-MC homogenate (5 µg/well) was added in a volume of 100 µl. The assay plates were then incubated at room temperature for 2 h. Assays were stopped by addition of excess cold wash buffer (20 mM Tris-Cl pH 7.5, 0.1% BSA) immediately followed by filtration over glass fiber filters (Whatman GF/B) previously soaked in 0.5% PEI. Non-specific binding was defined with 1 µM beta-CGRP. Protein bound radioactivity was determined using a gamma or scintillation counter. The $IC_{50}$ was defined as the concentration of a compound of invention required to displace 50% of radioligand binding.

Human CGRP receptor binding affinities for Examples 1-15 were each less than 1 nM.

What is claimed is:
1. A compound according to Formula (I)

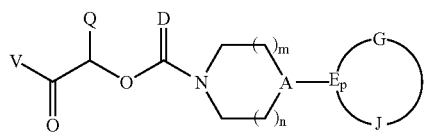

or a pharmaceutically acceptable salt thereof
wherein

V is —$N(R^1)(R^2)$ $R^1$ and $R^2$ are each independently $L^1$, wherein $L^1$ is selected from the group consisting of H, $C_{1-6}$alkyl, $C_{2-6}$alkenyl, $C_{2-6}$alkynyl, —$C_{1-6}$alkylene-amino($C_{1-3}$alkyl)$_2$, $C_{3-7}$cycloalkyl, phenyl, azetidinyl, adamantyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino and dioxolanyl; and $R^1$ and $R^2$ are each optionally and independently substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-3}$alkylamino, $C_{1-3}$dialkylamino, ($C_{1-3}$alkyl)$_{0-2}$ureido, phenyl and benzyl;

$R^1$ and $R^2$ optionally and independently contain 1 or 2 carbonyls wherein the carbon atom of said carbonyl is a member of the heterocycles comprising $R^1$ and $R^2$;

wherein $L^1$ is optionally and independently interrupted from the nitrogen to which it is attached by $L^2$, wherein $L^2$ is independently $C_{1-3}$alkylene or $C_{1-3}$alkylidene; or $R^1$ and $R^2$ together with the nitrogen to which they are attached form X, wherein X is azetidinyl, pyrrolyl, pyrrolinyl, pyrrolidinyl, imidazolinyl, imidazolidinyl, pyrazolinyl, pyrazolidinyl, azepinyl, diazepinyl, piperazinyl, piperidinyl, morpholino or thiomorpholino;

wherein X is optionally substituted with Y, wherein Y is dioxolanyl, $C_{1-9}$alkyl, $C_{2-9}$alkenyl, $C_{2-9}$alkynyl, $C_{1-4}$alkylamino, $C_{1-4}$ dialkylamino, $C_{1-4}$ alkoxy, $C_{3-7}$cycloalkyl, phenyl, azetidinyl, furanyl, thienyl, pyrrolyl, pyrrolinyl, pyrrolidinyl, pyrrolidinonyl, imidazolyl, imidazolinyl, imidazolidinyl, imidazolidinonyl, pyrazolyl, pyrazolinyl, pyrazolidinyl, azepinyl, diazepinyl, pyridyl, pyrimidinyl, dihydrobenzimidazolonyl, piperazinyl, piperidinyl, morpholino, benzothiazolyl, benzisothiazolyl or thiomorpholino;

and wherein X and Y are
optionally interrupted with Z, wherein Z is —NHC(O)O—, —NHC(O)NH—, NC(O)$NH_2$, —NH—, —$C_{1-3}$alkylene-, —$C_{1-3}$alkylene-, —$C_{1-3}$alkenylene-NHC(O)O—$C_{1-3}$alkylene-;
and
optionally and independently substituted with 1 or 2 of the same or different substituents selected from the group consisting of halo, $C_{1-4}$alkyl, amino, $C_{1-3}$alkylamino, —$C_{1-6}$alkylene-amino $(C_{1-3}$alkyl$)_2$, $(C_{1-3}$alkyl$)_{0-2}$ureido, phenyl and benzyl;

X and Y optionally and independently contain 1 or 2 carbonyls wherein the carbon atom of said carbonyl is a member of the heterocycles comprising X and Y;

provided that if X is substituted with Y, and if X and Y are not interrupted with Z, then X and Y optionally share one carbon atom and together form a spirocyclic moiety;

Q is Q' or Q";
wherein
Q' is $(S^y)_s R^3$; and
Q" is $NH(S^y)_s R^3$, $NHC(O)(S^y)_s R^3$, $NHC(O)O(S^y)_s R^3$, $NHC(O)NH(S^y)_s R^3$, $O(S^y)_s R^3$, $(S^y)_s NHR^3$, $(S^y)_s NHC(O)R^3$, $(S^y)_s NHC(O)OR^3$, $(S^y)_s NHC(O)NHR^3$ or $(S^y)_s OR^3$;
wherein $S^y$ is $C_{1-3}$alkylene or $C_{1-3}$alkylidene and s is 0 or 1;

$R^3$ is $R^{3a}$ or $R^{3b}$
wherein
$R^{3a}$ is indazolyl
wherein $R^{3a}$ is optionally substituted with 1 to 3 of the same or different substituents selected from the group consisting of benzyl, phenyl, —O-phenyl, —O—$C_{1-3}$alkylenephenyl, —$C_{1-3}$alkylene-OC(O)-phenyl, cyano, amino, nitro, halo, $C_{1-6}$alkyl, $C_{1-3}$mono-bi-tri-haloalkyl, $C_{1-3}$mono-bi-tri-haloalkyloxy, $(C_{1-3}$alkyl$)_{1-2}$amine, —$OR^{3'}$, —$C(O)R^{3'}$, —$C(O)O$—$R^{3'}$, —$O$—$C(O)R^{3'}$, —$N(R^{3'})_2$, —$C(O)N(R^{3'})_2$, —$N(R^{3'})C(O)(R^{3'})_2$, —$N(R^{3'})C(O)N(R^{3'})_2$, —$N(R^{3'})C(O)OR^{3'}$, —$O$—$C(O)N(R^{3'})_2$, —$N(R^{3'})SO_2 R^{3'}$, —$SO_2 N(R^{3'})_2$ and —$SO_2 R^{3'}$;
$R^{3'}$ is H or —$C_{1-6}$alkyl;
$R^{3b}$ is $R^{3a}$ but is not 1H-indazol-3-yl, or 1-methyl-1H-indazol-3-yl; optionally substituted in the carbon skeleton with mono-, di- or trisubstituted by fluorine, chlorine or bromine atoms or by branched or unbranched alkyl groups, $C_{3-8}$-cycloalkyl groups, phenylalkyl groups, alkenyl, alkoxy, phenyl, phenylalkoxy, trifluoromethyl, alkoxycarbonylalkyl, carboxyalkyl, alkoxycarbonyl, carboxy, dialkylaminoalkyl, dialkylaminoalkoxy, hydroxy, nitro, amino, acetylamino, propionylamino, benzoyl, benzoylamino, benzoylmethylamino, methylsulphonyloxy, aminocarbonyl, alkylaminocarbonyl, dialkylaminocarbonyl, alkanoyl, cyano, tetrazolyl, phenyl, pyridinyl, thiazolyl, furyl, trifluoromethoxy, trifluoromethylthio, trifluoromethylsulphinyl- or trifluoromethylsulphonyl groups;
wherein said substituents may be the same or different and the above-mentioned benzoyl, benzoylamino- and benzoylmethylamino groups may in turn additionally be substituted in the phenyl moiety by a fluorine, chlorine or bromine atom, or by an alkyl, trifluoromethyl, amino or acetylamino group;

D is O, NCN or $NSO_2 C_{1-3}$alkyl;
A is C, CH or COH;
m and n are independently 0, 1 or 2;
provided that
if m and n are 0, then A is not N;
if m is 2, then n is not 2; or
if n is 2, then m is not 2;

E is N, CH or C;
p is 1 and G, J and E together form $A^x$ or $A^y$;
$A^x$ is a fused heterocycle having two fused rings with 5 to 7 members in each of said rings, said heterocycle containing one to four of the same or different heteroatoms selected from the group consisting of O, N and S; and
optionally containing 1 or 2 carbonyls wherein the carbon atom of said carbonyl is a member of said fused heterocycle;
$A^y$ is a 4 to 6 membered heterocycle containing one to three heteroatoms selected from the group consisting of O, N and S; and
optionally containing 1 to 2 carbonyls, wherein the carbon atom of said carbonyl is a member of said 4 to 6 membered heterocycle;
wherein $A^x$ and $A^y$ are optionally substituted with $C_{1-4}$alkyl, $C_{1-4}$alkoxy, $C_{1-4}$haloalkyl, cyano, $C_{3-7}$cycloalkyl, phenyl, halophenyl, halo, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl or morpholino;
and further provided that
if Q is Q", then $R^3$ is $R^{3a}$; and
if Q is Q', then
$R^3$ is $R^{3b}$.

2. A compound according to claim 1 wherein Q is Q' and $R^3$ is $R^{3b}$.

3. A compound according to claim 1 wherein Q is Q' and Q' is $(S^y)_s R^3$, $S^y$ is $C_{1-3}$alkylene and s is 1.

4. A compound according to claim 1 wherein Q is Q' and Q' is $(S^y)_s R^3$, $S^y$ is methylene and s is 1.

5. A compound according to claim 1 wherein V is —$N(R^1)(R^2)$ and wherein
$R^1$ and $R^2$ together with the nitrogen to which they are attached form X,
wherein X is piperidinyl, piperazinyl or morpholino;
wherein X is substituted with Y, wherein Y is dioxolanyl, phenyl, pyridyl, piperazinyl, piperidinyl or $C_{1-4}$alkyl;
and wherein X and Y optionally share one carbon atom and together form a spirocyclic moiety.

6. A compound according to claim 1 wherein V is —$N(R^1)(R^2)$ and wherein
$R^1$ and $R^2$ together with the nitrogen to which they are attached form X,
wherein X is piperidinyl, piperazinyl or morpholino;
wherein X is substituted with Y, wherein Y is dioxolanyl, phenyl, pyridyl, piperazinyl, piperidinyl or $C_1$-4-alkyl.

7. A compound according to claim 1 wherein X and Y are not interrupted with Z.

8. A compound according to claim 1 wherein $R^3$ is $R^{3a}$ and $R^{3a}$ is indazolyl optionally substituted with 1 to 3 of the same or different substituents selected from the group consisting of benzyl, phenyl, —O-phenyl, —O—$C_{1-3}$alkylenephenyl, —$C_{1-3}$alkylene-OC(O)-phenyl, cyano, amino, nitro, halo, $C_{1-6}$alkyl, $C_{1-3}$mono-bi-tri-haloalkyl, $C_{1-3}$mono-bi-tri-haloalkyloxy, $(C_{1-3}$alkyl$)_{1-2}$-amine, —$OR^{3'}$, —$C(O)R^{3'}$, —$C(O)O$—$R^{3'}$, —$O$—$C(O)R^{3'}$, —$N(R^{3'})_2$, —$C(O)N(R^{3'})_2$, —$N(R^{3'})C(O)(R^{3'})_2$, —$N(R^{3'})C(O)N(R^{3'})_2$, —$N(R^{3'})C(O)OR^{3'}$, —$O$—$C(O)N(R^{3'})_2$, —$N(R^{3'})SO_2 R^{3'}$, —$SO_2 N(R^{3'})_2$ and —$SO_2 R^{3'}$;
and $R^{3'}$ is H or —$C_{1-6}$alkyl.

9. A compound according to claim 1 wherein $R^3$ is $R^{3b}$ and $R^{3b}$ is 1H-indazol-5-yl optionally substituted in the carbon skeleton with mono-, di- or trisubstituted by fluorine, chlorine or bromine atoms or by branched or unbranched alkyl groups, C$_{3-8}$-cycloalkyl groups, phenylalkyl groups, alkenyl, alkoxy, phenyl, phenylalkoxy, trifluoromethyl, alkoxycarbonylalkyl, carboxyalkyl, alkoxycarbonyl, carboxy, dialkylaminoalkyl, dialkylaminoalkoxy, hydroxy, nitro, amino, acetylamino, propionylamino, benzoyl, benzoylamino, benzoylmethylamino, methylsulphonyloxy, aminocarbonyl, alkylaminocarbonyl, dialkylaminocarbonyl, alkanoyl, cyano, tetrazolyl, phenyl, pyridinyl, thiazolyl, furyl, trifluoromethoxy, trifluoromethylthio, trifluoromethylsulphinyl- or trifluoromethylsulphonyl groups;

wherein said substituents may be the same or different and the above-mentioned benzoyl, benzoylamino- and benzoylmethylamino groups may in turn additionally be substituted in the phenyl moiety by a fluorine, chlorine or bromine atom, or by an alkyl, trifluoromethyl, amino or acetylamino group.

10. A compound according to claim 1 wherein m and n are each 1.

11. A compound according to claim 1 wherein D is O.

12. A compound of claim 1 selected from the group consisting of

3(7-Methyl-1H-indazol-5-yl)-1-oxo-1-(4-(piperidin-1-yl)piperidin-1-yl)propan-2-yl 4-(1,2-dihydro-2-oxo-quinazolin-3(4H)-yl)piperidine-1-carboxylate;

(R)-3-(7-Methyl-1H-indazol-5-yl)-1-oxo-1-(4-(piperidin-1-yl)piperidin-1-yl)propan-2-yl 4-(2-oxo-1,2-dihydroquinazolin-3(4H)-yl)piperidine-1-carboxylate;

(R)-3-(7-Methyl-1H-indazol-5-yl)-1-oxo-1-(4-(piperidin-1-yl)piperidin-1-yl)propan-2-yl 4-(8-fluoro-2-oxo-1,2-dihydroquinazolin-3(4H)-yl)piperidine-1-carboxylate;

(R)-3(7-Methyl-1H-indazol-5-yl)-1-oxo-1-(4-(piperidin-1-yl)piperidin-1-yl)propan-2-yl 4-(2-oxo-1,2-dihydroquinolin-3-yl)piperidine-1-carboxylate;

(R)-3(7-Methyl-1H-indazol-5-yl)-1-oxo-1-(4-(piperidin-1-yl)piperidin-1-yl)propan-2-yl 4-(2-oxo-4-phenyl-2,3-dihydroimidazol-1-yl)piperidine-1-carboxylate;

(R)-3(7-Methyl-1H-indazol-5-yl)-1-oxo-1-(4-(piperidin-1-yl)piperidin-1-yl)propan-2-yl 4-hydroxy-4-(2-oxo-1,2-dihydroquinolin-3-yl)piperidine-1-carboxylate;

(R)-3-(7-Methyl-1H-indazol-5-yl)-1-oxo-1-(4-(piperidin-1-yl)piperidin-1-yl)propan-2-yl 4-(7-fluoro-2-oxo-1,2-dihydroquinazolin-3(4H)-yl)piperidine-1-carboxylate;

(R)-1-(4-(5,6-Dihydropyridin-1(2H)-yl)piperidin-1-yl)-3-(7-methyl-1H-indazol-5-yl)-1-oxopropan-2-yl 4-(2-oxo-1,2-dihydroquinolin-3-yl)piperidine-1-carboxylate;

(R)-3-(7-Methyl-1H-indazol-5-yl)-1-oxo-1-(piperidin-1-yl)propan-2-yl 4-(2-oxo-1,2-dihydroquinolin-3-yl)piperidine-1-carboxylate;

(R)-1-(4-Cyclohexylpiperazin-1-yl)-3-(7-methyl-1H-indazol-5-yl)-1-oxopropan-2-yl 4-(2-oxo-1,2-dihydroquinolin-3-yl)piperidine-1-carboxylate;

(R)-1-(4-(4-Fluorophenyl)piperazin-1-yl)-3-(7-methyl-1H-indazol-5-yl)-1-oxopropan-2-yl 4-(2-oxo-1,2-dihydroquinolin-3-yl)piperidine-1-carboxylate;

(R)-3-(7-Methyl-1H-indazol-5-yl)-1-oxo-1-(4-(pyridin-4-yl)piperazin-1-yl)propan-2-yl 4-(2-oxo-1,2-dihydroquinolin-3-yl)piperidine-1-carboxylate;

(±)-3-(7-Methyl-1H-indazol-5-yl)-1-oxo-1-(4-(piperidin-1-yl)piperidin-1-yl)propan-2-yl 4-(2-oxo-1,2-dihydroquinolin-3-yl)piperidine-1-carboxylate; and (R)-3-(7-Methyl-1H-indazol-5-yl)-1-oxo-1-(4-(piperidin-1-yl)piperidin-1-yl)propan-2-yl 4-(8-fluoro-2-oxo-1,2-dihydroquinolin-3-yl)piperidine-1-carboxylate;

or a pharmaceutically acceptable salt thereof.

13. A pharmaceutical composition comprising a compound according to claim 1.

14. A method of treating migraine comprising administration to a mammal in need thereof an effective anti-migraine amount of a pharmaceutical composition according to claim 13.

* * * * *

UNITED STATES PATENT AND TRADEMARK OFFICE
CERTIFICATE OF CORRECTION

PATENT NO.         : 7,772,244 B2                                       Page 1 of 1
APPLICATION NO.    : 11/091429
DATED              : August 10, 2010
INVENTOR(S)        : Andrew P. Degnan et al.

It is certified that error appears in the above-identified patent and that said Letters Patent is hereby corrected as shown below:

In the Claims:

Claim 1:

Column 134, line 51, change "$C_{1-4}$ dialkylamino" to -- $C_{1-4}$dialkylamino --.

Claim 6:

Column 136, line 51, change "$C_1$-4-alkyl" to -- $C_{1-4}$alkyl --.

Claim 12:

Column 137, line 24, change "3(7" to -- 3-(7 --.

Column 137, line 27, change "(R)-3(7" to -- (R)-3-(7 --.

Column 137, line 33, change "(R)-3(7" to -- (R)-3-(7 --.

Column 137, line 36, change "(R)-3(7" to -- (R)-3-(7 --.

Column 138, line 1, change "(R)-3(7" to -- (R)-3-(7 --.

Signed and Sealed this
Twenty-second Day of November, 2011

David J. Kappos
*Director of the United States Patent and Trademark Office*